US007741438B2

(12) United States Patent
Steele et al.

(10) Patent No.: US 7,741,438 B2

(45) Date of Patent: Jun. 22, 2010

(54) METHODS AND COMPOSITIONS INVOLVING ENDOPEPTIDASES PEPO2 AND PEPO3

(75) Inventors: James L. Steele, Middleton, WI (US); Jeffrey R. Broadbent, Smithfield, UT (US); Vidya R. Sridhar, Portland, OR (US)

(73) Assignees: Wisconsin Alumni Research Foundation, Madison, WI (US); Utah State University, Logan, UT (US)

(*) Notice: Subject to any disclaimer, the term of this patent is extended or adjusted under 35 U.S.C. 154(b) by 904 days.

(21) Appl. No.: 10/873,427

(22) Filed: Jun. 21, 2004

(65) Prior Publication Data

US 2005/0281914 A1 Dec. 22, 2005

Related U.S. Application Data

(60) Provisional application No. 60/480,536, filed on Jun. 20, 2003.

(51) Int. Cl.
*C07K 14/00* (2006.01)

(52) U.S. Cl. ....................... 530/350; 530/300; 435/7.1; 435/220

(58) Field of Classification Search ....................... None
See application file for complete search history.

(56) References Cited

U.S. PATENT DOCUMENTS 4,001,133 A 1/1977 Sorgenfrei et al. .......... 252/156
4,017,410 A 4/1977 Sorgenfrei et al. .......... 252/156
4,063,893 A 12/1977 Stoulil et al. .............. 23/230 R
4,739,906 A 4/1988 LoTurco ..................... 222/153
5,020,917 A 6/1991 Homan ....................... 366/161
5,106,631 A 4/1992 Turner et al. ................... 426/2
5,234,268 A 8/1993 Homan ....................... 366/161
5,356,639 A 10/1994 Jameson et al. ............... 426/40
5,387,422 A 2/1995 Handel et al. .................. 426/2
5,395,631 A 3/1995 Sweeney ..................... 426/42
5,429,829 A 7/1995 Ernster, Sr. .................. 426/36
5,462,755 A 10/1995 Mehnert ...................... 426/36
5,469,880 A 11/1995 Zimmerly ................... 137/240
5,505,979 A 4/1996 Sevenich .................... 426/582
5,547,691 A 8/1996 Kjaer et al. ................... 426/36
5,554,398 A 9/1996 Chen et al. .................... 426/36
5,593,598 A 1/1997 McGinness et al. ......... 210/748
5,635,228 A 6/1997 Sponholtz .................... 426/36
5,643,621 A 7/1997 Mehnert ...................... 426/36
5,688,542 A 11/1997 Tortosa ....................... 426/36
5,776,351 A 7/1998 McGinness et al. ......... 210/748
5,853,786 A 12/1998 Anbarci et al. .............. 426/582
5,888,966 A 3/1999 Larsen et al. .................. 514/2
5,948,459 A 9/1999 Telford ....................... 426/512
5,988,052 A 11/1999 Abler .......................... 99/494
6,020,324 A 2/2000 Jamas et al. .................. 514/54
6,026,740 A 2/2000 Abler .......................... 99/494
6,066,610 A 5/2000 Sramek ...................... 510/284
6,103,277 A 8/2000 Leufstedt et al. ............... 426/8
6,120,809 A 9/2000 Rhodes ........................ 426/36
6,127,142 A 10/2000 Harboe et al. ............. 435/68.1
6,139,889 A 10/2000 Guinee et al. ............... 426/231
6,140,078 A 10/2000 Sanders et al. ............. 435/69.1
6,183,804 B1 2/2001 Moran et al. ................ 426/582
6,242,036 B1 6/2001 Han et al. ................... 426/582
6,258,390 B1 7/2001 Budtz .......................... 426/36
6,270,823 B1 8/2001 Jolkin ........................ 426/478
6,297,042 B1 10/2001 Hicks ...................... 435/252.1
6,299,896 B1 10/2001 Cooper et al. ............... 424/441
6,335,040 B1 1/2002 Hoier et al. ................... 426/34
6,399,121 B1 6/2002 Nielsen ....................... 426/37
6,401,604 B1 6/2002 Rose et al. .................... 99/455
6,410,076 B1 6/2002 Van Der Meulen ......... 426/582
6,413,568 B1 7/2002 Rietveld ..................... 426/582
6,416,797 B1 7/2002 Han et al. ..................... 426/36
6,443,379 B2 9/2002 Lassmann .................. 242/178
6,455,092 B1 9/2002 Begueria .................... 426/582
6,458,394 B1 10/2002 Talbott ........................ 426/36
6,465,033 B2 10/2002 Menninga et al. ........... 426/512
6,468,570 B1 10/2002 Haddad et al. .............. 426/231
6,475,290 B2 11/2002 Jones ........................... 134/2
6,475,538 B2 11/2002 Thakar et al. ................. 426/43
6,485,762 B1 11/2002 Rizvi et al. ................... 426/34
6,548,089 B2 4/2003 Hoier et al. ................... 426/34
6,551,635 B2 4/2003 Nielsen ....................... 426/37
6,558,716 B1 5/2003 Smith et al. ................... 426/36
6,572,901 B2 6/2003 Han et al. ..................... 426/36
6,686,324 B2 2/2004 Ramirez et al. ............. 510/218

OTHER PUBLICATIONS

Seffernick et al. (J. Bacteriology, vol. 183, pp. 2405-2410, 2001).*
Wells, Biochemistry, vol. 29, pp. 8509-8517, 1990.*
Guo et al. (PNAS, vol. 101, No. 25, pp. 9205-9210, 2004.*
Bartels et al., "Accelerated ripening of Gouda cheese. II. Effect of freeze-shocked *Lactobacillus helveticus* on proteolysis and flavor development," *Milchwissenschaft*, 42(3):139-144, 1987.
Bartels et al., "Accelerated ripening of Gouda cheese. I. Effect of heat-shocked thermophilic lactobacilli and streptococci on proteolysis and flavor development,"*Milchwissenschaft*, 42(2):83-88, 1987.
Broadbent et al, "Contribution of *Lactococcus lactis* cell envelope proteinase sepcificity to peptide accumulation and bitterness in reduced-fat cheddar cheese," *Appl. Environ. Microbiol.*, 68(4):1778-1785, 2002.

(Continued)

*Primary Examiner*—Hope A Robinson
(74) *Attorney, Agent, or Firm*—Fulbright & Jaworski L.L.P.

(57) ABSTRACT

The present invention concerns the methods and compositions involving endopeptidase enzymes, especially PepO2 and PepO3 from *L. helveticus*, and their use in reducing bitterness by cleaving bitter peptides. In particular embodiments of the invention, these methods and compositions apply to the cheesemaking process. The invention also concerns the use of PepO2 and/or PepO3 polypeptides in the treatment or prevention of celiac sprue or as a food additive.

6 Claims, 9 Drawing Sheets

OTHER PUBLICATIONS

Broadbent et al., "Peptide accumulation and bitterness in cheddar cheese made using single-strain *Lactococcus lactis* starters with distinct proteinase specificities," *J. Dairy Sci*., 81:327-337, 1998.
Chavagnat et al, "Purification, characterization, cloning and sequencing of the gene encoding oligopeptidase PepO from *Streptococcus therrnophilus* A," *FEMS Microbiol Lett*., 191:79-85, 2000.
Chen and Okayama, "High-efficiency transformation of mammalian cells by plasmid DNA," *Mol Cell Biol*., 7(8):2745-2752., 1987.
Chen and Steele, "Genetic characterization and physiological role of endopeptidase O from *Lactobacillus helveticus* CNRZ32," *Appl. Environ. Microbiol*., 64(9):3411-3415, 1998.
Chen et al., "Identification and characterization of Pep O2 from *Lactobacillus helveticus* CNRZ32, an enzyme involved in the hydrolysis of a β-casein derived bitter peptide," *J. Anim. Sci*., 78(Supp. 1):401, 2000.
Chen et al., "Identification and characterization of *Lactobacillus helveticus* PepO2, an endopeptidase with post-proline specificity," *Appl. Environ. Microbiol*., 69(2):1276-1282, 2003.
Christensen et al., "Hydrolysis of casein-derived peptides αs1-casein(fl-9) and β-casein(fl93-209) by *Lactobacillus helveticus* peptidase deletion mutants indicates the presence of a previously undetected endopeptidase," *Appl. Environ. Microbiol*., 69(2):1283-1286, 2003.
Christensen et al., "Peptidase and amino acid catabolism in lactic acid bacteria," *Antonie van Leeuwenhoek*, 76:217-246, 1999.
Christensen, "Peptidases of *Lactobacillus helveticus*: role in physiology and casein hydrolysis," In: *Peptidases of Lactobacillus helveticus: Role in Physiology and Casein Hydrolysis*, University of Wisconsin-Madison, 2000.
Christensson et al., "Cloning and expression of an oligopeptidase, PepO, with novel specificity from *Lactobacillus rhamnosus* HN001 (DR20),"*Appl. Environ. Microbiol*., 68(1):254-262, 2002.
Exterkate and Alting, "The role of starter peptidases in the initial proteolytic events leading to amino acids in Gouda cheese," *Int. Dairy J*., 5:15-28, 1995.
Fenster and Steele, "Characterization of an arylesterase from *Lactobacillus helveticus* CNRZ.32," *J. Appl. Microbiol*., 88(4):572-583, 2000.
Fenster et al., "Characterization of a thiol-dependent endopeptidase from *Lactobacillus helveticus* CNRZ32," *J. Bacteriol*., 179(8):2529-2533, 1997.
Froeliger et al., "*Streptococcus parasanguis* pepO encodes an endopeptidase with structure and activity similar to those of enzymes that modulate peptide receptor signaling in Eukaryotic cells," *Infect. Immun*., 67(10):5206-5214, 1999.
Gomez et al., "Debittering activity of peptidases from selected *lactobacilli* strains in model cheeses," *Milchwissenschaft*, 51:315-319, 1996.
Hassan et al., "Factors affecting capsule size and production by lactic acid bacteria used as dairy starter cultures," *Int. J. Food Microbiol*., 64(1-2):199-203, 2001.
Hellendoom et al., "Cloning and analysis of the pepV dipeptidase gene of *Lactococcus lactis* MG1363," *J. Bacteriol*, 179(11):3410-3415, 1999.
Kaminogawa et al., "Identification of low molecular weigh peptides in Gouda-type cheese and evidence for the formulation of these peptides from 23 N-terminal residues of αsl-casein by proteinases of *Streptococcus cremoris* H61," *J. Food Sci*., 51(5):1253-1264, 1986.
Khalid and Marth, "Purification and partial characterization of a prolyl-dipeptidyl aminopeptidase from *Lactobacillus helveticus* CNRZ 32," *Appl. Environ. Microbiol*., 56(2):381-388, 1990.
Khalid et al., "Peptide hydrolases of *Lactobacullus helveticus* and *Lactobacullus delbrueckii* ssp. *bulgaricus*," *J. Dairy Sci*., 74:29-45, 1991.
Kok and De Vos, In: *Genetics and Biotechnology of Lactic Acid Bacteria*, Glasson and de Vos (Eds.), Blackie Academic and Professional, Glasgow, 1994.
Kunji et al., "The proteolytic systems of lactic acid bacteria," *Antonie van Leeuwenhoek*, 70:187-221, 1996.
Lee et al., "Removal of bitterness from the bitter peptides extracted from cheddar cheese with peptidases from *Lactococcus lactis* ssp. *cremoris* SK 11[1]," *J. Dairy Sci*., 79:1521-1528, 1996.
Lemieux and Simard, "Bitter flavour in dairy products I. A review of the factors likely to influence its development, mainly in cheese manufacture," *Lait*., 71:599-636, 1991.
Madkor et al., "Ripening of cheddar cheese with added attenuated adjunct cultures of *Lactobacilli*," *J. Dairy Sci*., 83:1684-1691, 2000.
Mierau et al., "Cloning and sequencing of the gene for a *Lactococcal endopeptidase*, an enzyme with sequence similarity to mammalian enkephalinase," *J. Bacteriology*, 175(7):2087-2096, 1993.
Mulholland, "Proteolytic systems of dairy lactic acid bacteria," In: *Microbiology and Biochemistry of Cheese and Fermented Milk*, Law (Ed.), Blackie Academic and Professional, Glasgow, 1997.
Niven et al., "A study of the substrate specificity of aminopeptidase N. from *Lactococcus lactis* subsp. *cremoris* Wg2," Appl.. Environ. Microbiol., 44:100-105, 1995.
Nowakowski et al., "Cloning of peptidase genes from *Lactobacillus helveticus* CNRZ 32," *Appl. Microbiol. Biotechnol*,, 39:204-210, 1993.
Pederson et al., "Genetic characterization of a cell envelope-associated proteinase from *Lactobacillus helveticus* CNRZ32," *J. Bacteriology*, 181(15):4592-4597, 1999.
Pritchard and Coolbear, "The physiology and biochemistry of the proteolytic system in lactic acid bacteria," *FEMS Microbiol. Rev*., 12:179-206, 1993.
Schuppan et al., "Gluten and the gut-lessons for immune regulation," *Science*, 297:2218-2220, 2002.
Shan et al, "Structural basis for glutin intolerance in celiac sprue," *Science*, 297:2275-2279, 2002.
Tan et al., "Degradation and debittering of a tryptic digest from β-casein by aminopeptidase N from *Lactococcus lactis* subsp. *cremoris* WG2," *Appl. Environ. Microbiol*., 59(5):1430-1436, 1993.
Tynkkynen etal., "Genetic and biochemical characterization of the oligopeptide transport system of *Lactococcus lactis*," *J. Bacteriology*, 175(23):7523-7532, 1993.
Vader et al, "Specificity of tissue transglutaminase explains cereal toxicity in celiac disease," *J. Exp. Med*., 195(5):643-649, 2002.

* cited by examiner

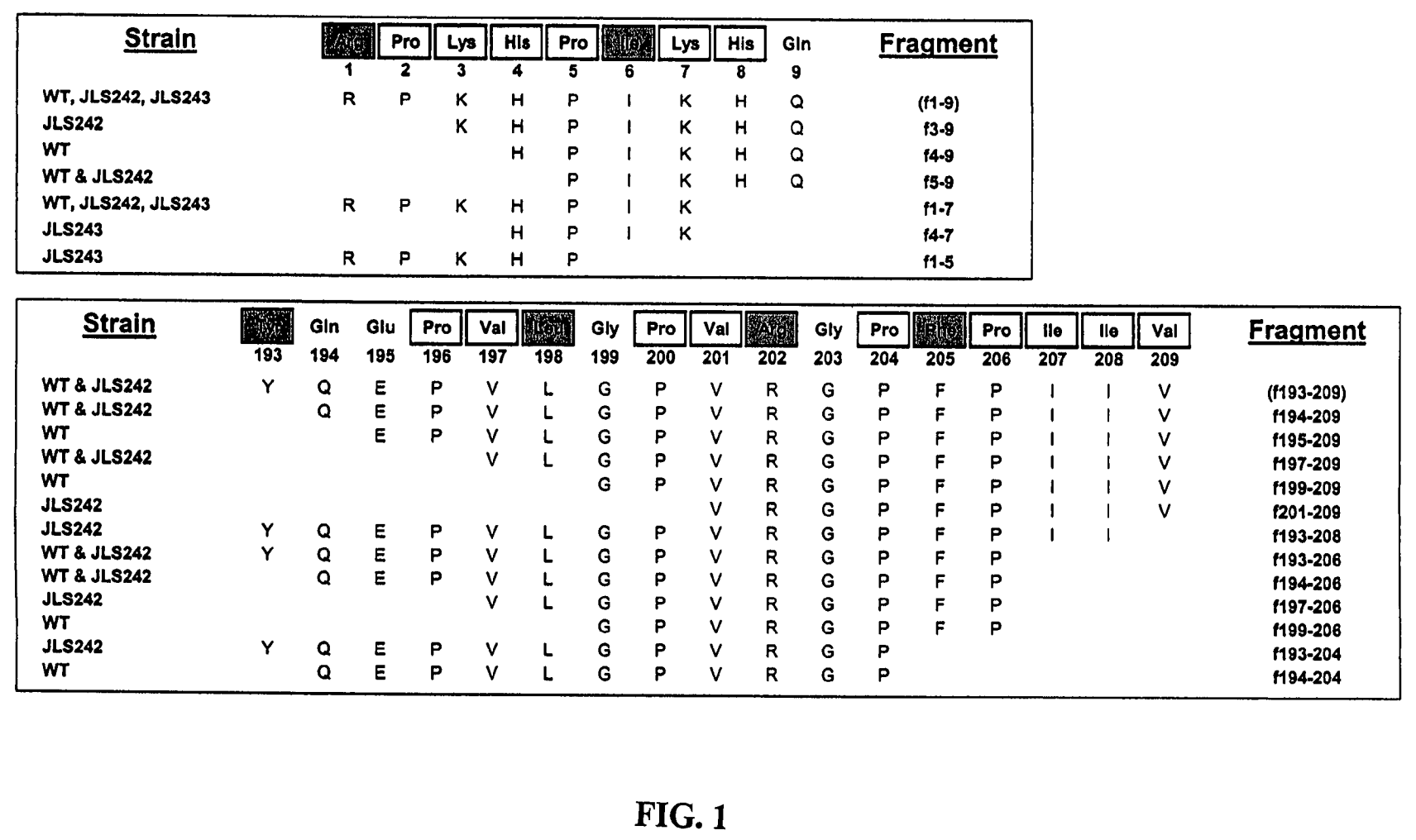

| Strain | Arg 1 | Pro 2 | Lys 3 | His 4 | Pro 5 | Ile 6 | Lys 7 | His 8 | Gln 9 | Fragment |
|---|---|---|---|---|---|---|---|---|---|---|
| WT, JLS242, JLS243 | R | P | K | H | P | I | K | H | Q | (f1-9) |
| JLS242 | | | K | H | P | I | K | H | Q | f3-9 |
| WT | | | | H | P | I | K | H | Q | f4-9 |
| WT & JLS242 | | | | | P | I | K | H | Q | f5-9 |
| WT, JLS242, JLS243 | R | P | K | H | P | I | K | | | f1-7 |
| JLS243 | | | | H | P | I | K | | | f4-7 |
| JLS243 | R | P | K | H | P | | | | | f1-5 |

| Strain | Tyr 193 | Gln 194 | Glu 195 | Pro 196 | Val 197 | Leu 198 | Gly 199 | Pro 200 | Val 201 | Arg 202 | Gly 203 | Pro 204 | Phe 205 | Pro 206 | Ile 207 | Ile 208 | Val 209 | Fragment |
|---|---|---|---|---|---|---|---|---|---|---|---|---|---|---|---|---|---|---|
| WT & JLS242 | Y | Q | E | P | V | L | G | P | V | R | G | P | F | P | I | I | V | (f193-209) |
| WT & JLS242 | | Q | E | P | V | L | G | P | V | R | G | P | F | P | I | I | V | f194-209 |
| WT | | | E | P | V | L | G | P | V | R | G | P | F | P | I | I | V | f195-209 |
| WT & JLS242 | | | | | V | L | G | P | V | R | G | P | F | P | I | I | V | f197-209 |
| WT | | | | | | | G | P | V | R | G | P | F | P | I | I | V | f199-209 |
| JLS242 | | | | | | | | | V | R | G | P | F | P | I | I | V | f201-209 |
| JLS242 | Y | Q | E | P | V | L | G | P | V | R | G | P | F | P | I | I | | f193-208 |
| WT & JLS242 | Y | Q | E | P | V | L | G | P | V | R | G | P | F | P | | | | f193-206 |
| WT & JLS242 | | Q | E | P | V | L | G | P | V | R | G | P | F | P | | | | f194-206 |
| JLS242 | | | | | V | L | G | P | V | R | G | P | F | P | | | | f197-206 |
| WT | | | | | | | G | P | V | R | G | P | F | P | | | | f199-206 |
| JLS242 | Y | Q | E | P | V | L | G | P | V | R | G | P | | | | | | f193-204 |
| WT | | Q | E | P | V | L | G | P | V | R | G | P | | | | | | f194-204 |

FIG. 1

SEQUENCE LISTING

```
<160> NUMBER OF SEQ ID NOS: 51

<210> SEQ ID NO 1
<211> LENGTH: 2395
<212> TYPE: DNA
<213> ORGANISM: Lactobacillus helveticus
<220> FEATURE:
<221> NAME/KEY: CDS
<222> LOCATION: (353)..(2293)

<400> SEQUENCE: 1

tctagaggat ctaagacagt cattgagccc ttaggaccaa cttgtgggtt gccgtcagca      60

tcaacagttg ctaagtaaac taagttattc ttgaaaagat ttacttgttc ttcagtaagc     120

ttgttagtat ttaatttctt catagataat acatcccttc tgttttatca atacactata     180

agtatacatc aatttaatag caggtgttag agatgtgctt acatccttat ttttatttaa     240

caaaatgctt ttattactat aaataagcaa aattaaataa gcaaaattaa attttcattt     300

tattttaaaa aatgctatga tttaaccaac taaaaaacaa aggagaaaac at atg aat     358
                                                          Met Asn
                                                            1

tta gca aaa atc cgc ggc ggt gct ggt gat atc acc aag ccc gat cta       406
Leu Ala Lys Ile Arg Gly Gly Ala Gly Asp Ile Thr Lys Pro Asp Leu
        5                   10                  15

aat gcc cgc att caa gat aac tta tac tta gcc gtt aac tct gac tgg       454
Asn Ala Arg Ile Gln Asp Asn Leu Tyr Leu Ala Val Asn Ser Asp Trp
    20                  25                  30

att tct aaa gcc aag atc cct gcc gat cgt cca tta atc agt agt ttc       502
Ile Ser Lys Ala Lys Ile Pro Ala Asp Arg Pro Leu Ile Ser Ser Phe
 35                  40                  45                  50

agt gaa att gat tta aaa atc gaa aaa gaa ttg atg aac gac tta gct       550
Ser Glu Ile Asp Leu Lys Ile Glu Lys Glu Leu Met Asn Asp Leu Ala
                55                  60                  65

gat ttt gct tct ggt aaa aaa gct ttg cct gat att cct aac ttt gac       598
Asp Phe Ala Ser Gly Lys Lys Ala Leu Pro Asp Ile Pro Asn Phe Asp
```

-continued

```
                70                  75                  80

aag gca atc gaa gtt tat aaa tta gct aaa gat ttc gcc aaa aga gat      646
Lys Ala Ile Glu Val Tyr Lys Leu Ala Lys Asp Phe Ala Lys Arg Asp
            85                  90                  95

gcc gat ggc ttt caa cct gct caa gct gat ctt gaa act tta ata aac      694
Ala Asp Gly Phe Gln Pro Ala Gln Ala Asp Leu Glu Thr Leu Ile Asn
        100                 105                 110

tta aaa gat gtc gat gac gtc aag caa aat cta gca aaa tta tta ttg      742
Leu Lys Asp Val Asp Asp Val Lys Gln Asn Leu Ala Lys Leu Leu Leu
115                 120                 125                 130

cgc ttt agc ttt cca ttt tta ttc gaa gtt gaa cct gat cgt aag aat      790
Arg Phe Ser Phe Pro Phe Leu Phe Glu Val Glu Pro Asp Arg Lys Asn
                135                 140                 145

acg aag acc aat tct ctt tcc ttt gac cgc aac tca ttg atc ttg cct      838
Thr Lys Thr Asn Ser Leu Ser Phe Asp Arg Asn Ser Leu Ile Leu Pro
            150                 155                 160

gac act act agt tac caa tca cct tct gct aag caa ttg ctc gat gtt      886
Asp Thr Thr Ser Tyr Gln Ser Pro Ser Ala Lys Gln Leu Leu Asp Val
        165                 170                 175

tgg caa aag caa acc gaa aac ttg tta aag atg gct ggt gtt gaa gaa      934
Trp Gln Lys Gln Thr Glu Asn Leu Leu Lys Met Ala Gly Val Glu Glu
    180                 185                 190

gct gct gct aag aaa tac gcc act gat gcg att gca ctc gat gct aaa      982
Ala Ala Ala Lys Lys Tyr Ala Thr Asp Ala Ile Ala Leu Asp Ala Lys
195                 200                 205                 210

atc gtt aag gtt gca aaa tca gcc gaa gaa cgt gcc gat gat gta gct     1030
Ile Val Lys Val Ala Lys Ser Ala Glu Glu Arg Ala Asp Asp Val Ala
                215                 220                 225

ctt tac aac cca atc aag act aac gaa ttt gaa gaa aag act agc tct     1078
Leu Tyr Asn Pro Ile Lys Thr Asn Glu Phe Glu Glu Lys Thr Ser Ser
            230                 235                 240

ttg aac ttg ggt cag ttg ctt gag cag ctc ttt gaa aag aag cca aat     1126
Leu Asn Leu Gly Gln Leu Leu Glu Gln Leu Phe Glu Lys Lys Pro Asn
        245                 250                 255

tac gtt gta gta agt gaa cca aaa ttc ttg gac cac ttc aat gaa tta     1174
Tyr Val Val Val Ser Glu Pro Lys Phe Leu Asp His Phe Asn Glu Leu
    260                 265                 270

ttt aat caa gag agc ttc gat gaa ctt aaa ggt tgg tta atc tct atc     1222
Phe Asn Gln Glu Ser Phe Asp Glu Leu Lys Gly Trp Leu Ile Ser Ile
275                 280                 285                 290

ttc att aat aaa gct gcc gcg ttt tta tca gaa gaa ttc cgt caa gct     1270
Phe Ile Asn Lys Ala Ala Ala Phe Leu Ser Glu Glu Phe Arg Gln Ala
                295                 300                 305

gcc ttc cca ttt aag caa gct act tat ggt caa aaa gaa ttg cct agt     1318
Ala Phe Pro Phe Lys Gln Ala Thr Tyr Gly Gln Lys Glu Leu Pro Ser
            310                 315                 320

caa gaa aag gaa gct tac tac aaa gct aat aat tta ttt gat gat gta     1366
Gln Glu Lys Glu Ala Tyr Tyr Lys Ala Asn Asn Leu Phe Asp Asp Val
        325                 330                 335

atc ggc gtt tat tat ggt cgc act tac ttc ggc gaa gat gcc aag gcc     1414
Ile Gly Val Tyr Tyr Gly Arg Thr Tyr Phe Gly Glu Asp Ala Lys Ala
    340                 345                 350

gac gtt gaa gat atg att cat cgc atg atc gat gtc tac gaa caa cga     1462
Asp Val Glu Asp Met Ile His Arg Met Ile Asp Val Tyr Glu Gln Arg
355                 360                 365                 370

ata acc aat aat gaa tgg ctc tca cct gct act aag gaa aag gca att     1510
Ile Thr Asn Asn Glu Trp Leu Ser Pro Ala Thr Lys Glu Lys Ala Ile
                375                 380                 385

act aag ttg cgc gcc ttg gtt tta aag att ggt tat cct aat aaa atc     1558
```

-continued

```
Thr Lys Leu Arg Ala Leu Val Leu Lys Ile Gly Tyr Pro Asn Lys Ile
            390                 395                 400

gat cac gtt tac gat tta ttc caa gtt act cca gca aat gaa ggt ggc     1606
Asp His Val Tyr Asp Leu Phe Gln Val Thr Pro Ala Asn Glu Gly Gly
        405                 410                 415

aac ctc tac agt aat caa gca aat att cgt gaa gtc agc tta aag cat     1654
Asn Leu Tyr Ser Asn Gln Ala Asn Ile Arg Glu Val Ser Leu Lys His
    420                 425                 430

aat ttc gat aaa ctg tac aag cca gtt gac cgc agc gaa tgg tac atg     1702
Asn Phe Asp Lys Leu Tyr Lys Pro Val Asp Arg Ser Glu Trp Tyr Met
435                 440                 445                 450

cca gga aac ttg atc aat gct tgt tac gat cca cag aga aac gat att     1750
Pro Gly Asn Leu Ile Asn Ala Cys Tyr Asp Pro Gln Arg Asn Asp Ile
                455                 460                 465

acc ttc cct gcc gct atc ttg gaa gca cct ttc tac gac atc aat gct     1798
Thr Phe Pro Ala Ala Ile Leu Glu Ala Pro Phe Tyr Asp Ile Asn Ala
            470                 475                 480

tct cgt gct act aac tat ggc ggt att ggt gtg gta atc gcc cac gaa     1846
Ser Arg Ala Thr Asn Tyr Gly Gly Ile Gly Val Val Ile Ala His Glu
        485                 490                 495

att tct cac gca ttc gac aac aac ggt gcc aaa tac gat gaa ttc ggc     1894
Ile Ser His Ala Phe Asp Asn Asn Gly Ala Lys Tyr Asp Glu Phe Gly
    500                 505                 510

aac atg aag aat tgg tgg acc aag gaa gac ttt gcg gaa ttt gaa aag     1942
Asn Met Lys Asn Trp Trp Thr Lys Glu Asp Phe Ala Glu Phe Glu Lys
515                 520                 525                 530

cgt act caa gct gaa atc gac ttg ttc gat ggc att aag tat ggt cct     1990
Arg Thr Gln Ala Glu Ile Asp Leu Phe Asp Gly Ile Lys Tyr Gly Pro
                535                 540                 545

gta act ctt aat ggt aaa caa atc gtt agt gaa aac atc gcc gac caa     2038
Val Thr Leu Asn Gly Lys Gln Ile Val Ser Glu Asn Ile Ala Asp Gln
            550                 555                 560

ggt ggt tta act gca ggt att gaa gct aat aag aat gaa cat ggc gac     2086
Gly Gly Leu Thr Ala Gly Ile Glu Ala Asn Lys Asn Glu His Gly Asp
        565                 570                 575

atg aaa gaa cta ttc gaa aac tat gct cgc att tgg gca agt aaa gaa     2134
Met Lys Glu Leu Phe Glu Asn Tyr Ala Arg Ile Trp Ala Ser Lys Glu
    580                 585                 590

tct cct gaa atc att aag aca att gcc gca ttc gat gtt cac gct cca     2182
Ser Pro Glu Ile Ile Lys Thr Ile Ala Ala Phe Asp Val His Ala Pro
595                 600                 605                 610

ggt cct gta aga gtt aac gtt caa gtg caa tgc caa cct gaa ttt tac     2230
Gly Pro Val Arg Val Asn Val Gln Val Gln Cys Gln Pro Glu Phe Tyr
                615                 620                 625

aaa gcc ttc aat gtt caa gaa gga gat ggc atg tgg ctt gac cct gct     2278
Lys Ala Phe Asn Val Gln Glu Gly Asp Gly Met Trp Leu Asp Pro Ala
            630                 635                 640

aag cgc gta gtc att tggtaaatct ttaatcaata aatctaaaat cctattaaat     2333
Lys Arg Val Val Ile
        645

cttggtatta accttgaatt aataggattt tttgcttcat taagcatcgc tatttcctag   2393

gt                                                                  2395


<210> SEQ ID NO 2
<211> LENGTH: 647
<212> TYPE: PRT
<213> ORGANISM: Lactobacillus helveticus

<400> SEQUENCE: 2
```

-continued

```
Met Asn Leu Ala Lys Ile Arg Gly Gly Ala Gly Asp Ile Thr Lys Pro
  1               5                  10                  15

Asp Leu Asn Ala Arg Ile Gln Asp Asn Leu Tyr Leu Ala Val Asn Ser
            20                  25                  30

Asp Trp Ile Ser Lys Ala Lys Ile Pro Ala Asp Arg Pro Leu Ile Ser
        35                  40                  45

Ser Phe Ser Glu Ile Asp Leu Lys Ile Glu Lys Glu Leu Met Asn Asp
    50                  55                  60

Leu Ala Asp Phe Ala Ser Gly Lys Lys Ala Leu Pro Asp Ile Pro Asn
 65                  70                  75                  80

Phe Asp Lys Ala Ile Glu Val Tyr Lys Leu Ala Lys Asp Phe Ala Lys
                 85                  90                  95

Arg Asp Ala Asp Gly Phe Gln Pro Ala Gln Ala Asp Leu Glu Thr Leu
            100                 105                 110

Ile Asn Leu Lys Asp Val Asp Asp Val Lys Gln Asn Leu Ala Lys Leu
        115                 120                 125

Leu Leu Arg Phe Ser Phe Pro Phe Leu Phe Glu Val Glu Pro Asp Arg
    130                 135                 140

Lys Asn Thr Lys Thr Asn Ser Leu Ser Phe Asp Arg Asn Ser Leu Ile
145                 150                 155                 160

Leu Pro Asp Thr Thr Ser Tyr Gln Ser Pro Ser Ala Lys Gln Leu Leu
                165                 170                 175

Asp Val Trp Gln Lys Gln Thr Glu Asn Leu Leu Lys Met Ala Gly Val
            180                 185                 190

Glu Glu Ala Ala Ala Lys Lys Tyr Ala Thr Asp Ala Ile Ala Leu Asp
        195                 200                 205

Ala Lys Ile Val Lys Val Ala Lys Ser Ala Glu Glu Arg Ala Asp Asp
    210                 215                 220

Val Ala Leu Tyr Asn Pro Ile Lys Thr Asn Glu Phe Glu Glu Lys Thr
225                 230                 235                 240

Ser Ser Leu Asn Leu Gly Gln Leu Leu Glu Gln Leu Phe Glu Lys Lys
                245                 250                 255

Pro Asn Tyr Val Val Val Ser Glu Pro Lys Phe Leu Asp His Phe Asn
            260                 265                 270

Glu Leu Phe Asn Gln Glu Ser Phe Asp Glu Leu Lys Gly Trp Leu Ile
        275                 280                 285

Ser Ile Phe Ile Asn Lys Ala Ala Ala Phe Leu Ser Glu Glu Phe Arg
    290                 295                 300

Gln Ala Ala Phe Pro Phe Lys Gln Ala Thr Tyr Gly Gln Lys Glu Leu
305                 310                 315                 320

Pro Ser Gln Glu Lys Glu Ala Tyr Tyr Lys Ala Asn Asn Leu Phe Asp
                325                 330                 335

Asp Val Ile Gly Val Tyr Tyr Gly Arg Thr Tyr Phe Gly Glu Asp Ala
            340                 345                 350

Lys Ala Asp Val Glu Asp Met Ile His Arg Met Ile Asp Val Tyr Glu
        355                 360                 365

Gln Arg Ile Thr Asn Asn Glu Trp Leu Ser Pro Ala Thr Lys Glu Lys
    370                 375                 380

Ala Ile Thr Lys Leu Arg Ala Leu Val Leu Lys Ile Gly Tyr Pro Asn
385                 390                 395                 400

Lys Ile Asp His Val Tyr Asp Leu Phe Gln Val Thr Pro Ala Asn Glu
                405                 410                 415

Gly Gly Asn Leu Tyr Ser Asn Gln Ala Asn Ile Arg Glu Val Ser Leu
```

-continued

```
            420                 425                 430

Lys His Asn Phe Asp Lys Leu Tyr Lys Pro Val Asp Arg Ser Glu Trp
        435                 440                 445

Tyr Met Pro Gly Asn Leu Ile Asn Ala Cys Tyr Asp Pro Gln Arg Asn
    450                 455                 460

Asp Ile Thr Phe Pro Ala Ala Ile Leu Glu Ala Pro Phe Tyr Asp Ile
465                 470                 475                 480

Asn Ala Ser Arg Ala Thr Asn Tyr Gly Gly Ile Gly Val Val Ile Ala
                485                 490                 495

His Glu Ile Ser His Ala Phe Asp Asn Asn Gly Ala Lys Tyr Asp Glu
            500                 505                 510

Phe Gly Asn Met Lys Asn Trp Trp Thr Lys Glu Asp Phe Ala Glu Phe
        515                 520                 525

Glu Lys Arg Thr Gln Ala Glu Ile Asp Leu Phe Asp Gly Ile Lys Tyr
    530                 535                 540

Gly Pro Val Thr Leu Asn Gly Lys Gln Ile Val Ser Glu Asn Ile Ala
545                 550                 555                 560

Asp Gln Gly Gly Leu Thr Ala Gly Ile Glu Ala Asn Lys Asn Glu His
                565                 570                 575

Gly Asp Met Lys Glu Leu Phe Glu Asn Tyr Ala Arg Ile Trp Ala Ser
            580                 585                 590

Lys Glu Ser Pro Glu Ile Ile Lys Thr Ile Ala Ala Phe Asp Val His
        595                 600                 605

Ala Pro Gly Pro Val Arg Val Asn Val Gln Val Gln Cys Gln Pro Glu
    610                 615                 620

Phe Tyr Lys Ala Phe Asn Val Gln Glu Gly Asp Gly Met Trp Leu Asp
625                 630                 635                 640

Pro Ala Lys Arg Val Val Ile
                645


<210> SEQ ID NO 3
<211> LENGTH: 2760
<212> TYPE: DNA
<213> ORGANISM: Lactobacillus helveticus
<220> FEATURE:
<221> NAME/KEY: CDS
<222> LOCATION: (425)..(2353)

<400> SEQUENCE: 3

cactgtcttt cattacatta gtctttgcca aagatttcgc tcactttgca ctatcaatgt     60

ttattttgac tttgggtgaa tctaccgcct ttccagctat tccagcctac gtgaatgatt    120

tatcacctaa aacaagtaag ggtaaatatc aaggagcaac gatggctgcc agcggtattg    180

gccgtgcctt tggcccgcta tttggtggtc tagtaattga tcaagcaggc tatattcctt    240

tcttctgggt agctgcgatt gtaattgcct tgatgatcgt catgatgatt ccaatttatt    300

taaagttagc caaaaagctt actttgtata agtaaaaaag cagactatat taaatcaaaa    360

tgatatactt agaatgattt aatattaatt tgataataag ggggatttct ctttgaataa    420

taaa atg act gta cgc ggc ggt gct ggc gac att act gaa gcc gat tta     469
     Met Thr Val Arg Gly Gly Ala Gly Asp Ile Thr Glu Ala Asp Leu
       1               5                  10                  15

tca gct cgt cca caa gat aat tta tac tta gcc gtt aac tca gaa tgg     517
Ser Ala Arg Pro Gln Asp Asn Leu Tyr Leu Ala Val Asn Ser Glu Trp
                20                  25                  30

tta aag aat gcc aag att cca tca gat cgt tcc aga act agt agt ttt     565
Leu Lys Asn Ala Lys Ile Pro Ser Asp Arg Ser Arg Thr Ser Ser Phe
```

-continued

```
             35                  40                  45

gat ggt att gac tta aac att gaa aaa gaa ttg atg caa gac ttt gca      613
Asp Gly Ile Asp Leu Asn Ile Glu Lys Glu Leu Met Gln Asp Phe Ala
        50                  55                  60

gat ttc gca gat ggc aaa aaa gat ttg cca gat gta cct aac ttt gaa      661
Asp Phe Ala Asp Gly Lys Lys Asp Leu Pro Asp Val Pro Asn Phe Glu
    65                  70                  75

aag gca gta gca ctt tac aag atc gct aaa gat ttt gat aga aga aat      709
Lys Ala Val Ala Leu Tyr Lys Ile Ala Lys Asp Phe Asp Arg Arg Asn
 80                  85                  90                  95

gcg gat ggc gca gat cca att caa gca gat tta cat gaa atc tta ggc      757
Ala Asp Gly Ala Asp Pro Ile Gln Ala Asp Leu His Glu Ile Leu Gly
                100                 105                 110

ttg cgc aac ttc gcc gac ttt act ttg aag gct gcc gac ttc ttc aag      805
Leu Arg Asn Phe Ala Asp Phe Thr Leu Lys Ala Ala Asp Phe Phe Lys
            115                 120                 125

aat ggt ttt cct atg cca ttt gat ttt tca gtt gaa gca gat atg aag      853
Asn Gly Phe Pro Met Pro Phe Asp Phe Ser Val Glu Ala Asp Met Lys
        130                 135                 140

aat act aag att cat tca ctt caa ttt ggt ggt cca ggc aca ttc ttg      901
Asn Thr Lys Ile His Ser Leu Gln Phe Gly Gly Pro Gly Thr Phe Leu
    145                 150                 155

cca gat act act act tac aag act ccc gct gct gaa aag ctt ttg gct      949
Pro Asp Thr Thr Thr Tyr Lys Thr Pro Ala Ala Glu Lys Leu Leu Ala
160                 165                 170                 175

gtt ttg aag gag caa tca atc aac ttg tta aca atg agc ggc att agc      997
Val Leu Lys Glu Gln Ser Ile Asn Leu Leu Thr Met Ser Gly Ile Ser
                180                 185                 190

aag tct gaa gct gaa gac tat gct gaa aag gct ctg gca tat gat gct     1045
Lys Ser Glu Ala Glu Asp Tyr Ala Glu Lys Ala Leu Ala Tyr Asp Ala
            195                 200                 205

aag att gcc aag gta gtt aag tct gcc gaa gaa tgg gct gac tat cct     1093
Lys Ile Ala Lys Val Val Lys Ser Ala Glu Glu Trp Ala Asp Tyr Pro
        210                 215                 220

gct aca tat aat cca att tct cgt gat gat ttt gcc gat aag ttc aag     1141
Ala Thr Tyr Asn Pro Ile Ser Arg Asp Asp Phe Ala Asp Lys Phe Lys
    225                 230                 235

tca ttc aag atg gat tac ttc tta ggt gaa ctt ttt gct aag aag cca     1189
Ser Phe Lys Met Asp Tyr Phe Leu Gly Glu Leu Phe Ala Lys Lys Pro
240                 245                 250                 255

gaa aga gta att aat act gaa cca cgt tac tta gat tac gct gaa gaa     1237
Glu Arg Val Ile Asn Thr Glu Pro Arg Tyr Leu Asp Tyr Ala Glu Glu
                260                 265                 270

ctc ttg aat gaa gat gtt ttt gca gaa att aag gct tgg atg cta gtt     1285
Leu Leu Asn Glu Asp Val Phe Ala Glu Ile Lys Ala Trp Met Leu Val
            275                 280                 285

aag ttc gtc aat ggc gta gct agt tca ttg tca caa gaa ttt cgt gaa     1333
Lys Phe Val Asn Gly Val Ala Ser Ser Leu Ser Gln Glu Phe Arg Glu
        290                 295                 300

gct gcc ttt cca ttt agc caa gct ttg tct ggt caa cct gaa ctt cca     1381
Ala Ala Phe Pro Phe Ser Gln Ala Leu Ser Gly Gln Pro Glu Leu Pro
    305                 310                 315

agc ggt gtt aag caa gca tat cac att gct aac agc gac ttt agc gaa     1429
Ser Gly Val Lys Gln Ala Tyr His Ile Ala Asn Ser Asp Phe Ser Glu
320                 325                 330                 335

gta gtt ggt gtt tac tat ggt caa aca tac ttt ggt gca gaa gct aag     1477
Val Val Gly Val Tyr Tyr Gly Gln Thr Tyr Phe Gly Ala Glu Ala Lys
                340                 345                 350

gct gat gtg act gac atg att cat aag atg ctt gac gtt tat gaa aag     1525
```

-continued

```
Ala Asp Val Thr Asp Met Ile His Lys Met Leu Asp Val Tyr Glu Lys
            355                 360                 365

aga atc cgt gaa aat tca tgg ctt tca caa gca act aag gat aag gca      1573
Arg Ile Arg Glu Asn Ser Trp Leu Ser Gln Ala Thr Lys Asp Lys Ala
        370                 375                 380

att gtt aag ttg cgt gct ttg atc ttg aag att ggt tac cca gat aag      1621
Ile Val Lys Leu Arg Ala Leu Ile Leu Lys Ile Gly Tyr Pro Asp Lys
    385                 390                 395

att gaa gaa atc tat gat cgt tta act gtt gat cca gaa gct agt ctt      1669
Ile Glu Glu Ile Tyr Asp Arg Leu Thr Val Asp Pro Glu Ala Ser Leu
400                 405                 410                 415

tat gct aat gaa gct caa ttt ggc aga gaa caa att aag tac aat ttg      1717
Tyr Ala Asn Glu Ala Gln Phe Gly Arg Glu Gln Ile Lys Tyr Asn Leu
                420                 425                 430

gaa aag tta gat caa gat gtt gac cgc agc gta tgg ctt atg cca ggt      1765
Glu Lys Leu Asp Gln Asp Val Asp Arg Ser Val Trp Leu Met Pro Gly
            435                 440                 445

aac ctc gtt aac gca tgt tac gat cct caa aga aac gat ttg act ttc      1813
Asn Leu Val Asn Ala Cys Tyr Asp Pro Gln Arg Asn Asp Leu Thr Phe
        450                 455                 460

cca gct gct att ttg caa aag cct ttc tac gac ttg aag caa tca cgt      1861
Pro Ala Ala Ile Leu Gln Lys Pro Phe Tyr Asp Leu Lys Gln Ser Arg
    465                 470                 475

agc ttg aac tac ggt ggt atc ggt gtt gta att gcc cac gaa att tct      1909
Ser Leu Asn Tyr Gly Gly Ile Gly Val Val Ile Ala His Glu Ile Ser
480                 485                 490                 495

cac gcc ttt gac aac aac ggt gct caa ttt gat gaa ttc ggt aat atg      1957
His Ala Phe Asp Asn Asn Gly Ala Gln Phe Asp Glu Phe Gly Asn Met
                500                 505                 510

aag aat tgg tgg act gaa aag gac ttc gct gaa ttt aag aag cgg act      2005
Lys Asn Trp Trp Thr Glu Lys Asp Phe Ala Glu Phe Lys Lys Arg Thr
            515                 520                 525

caa gct gaa atc gac ttg ttt gac ggt att aag tac ggc cct gta act      2053
Gln Ala Glu Ile Asp Leu Phe Asp Gly Ile Lys Tyr Gly Pro Val Thr
        530                 535                 540

ctt aac ggt aaa caa atc gta tcc gaa aat att gcc gat caa ggt ggt      2101
Leu Asn Gly Lys Gln Ile Val Ser Glu Asn Ile Ala Asp Gln Gly Gly
    545                 550                 555

tta aca gcc gct gtt gaa gcc aac aag ggc gaa gat ggc aac atg aag      2149
Leu Thr Ala Ala Val Glu Ala Asn Lys Gly Glu Asp Gly Asn Met Lys
560                 565                 570                 575

gaa tta ttt gaa aac ttt gct cgt gtc tgg gca acc aag caa ttg cca      2197
Glu Leu Phe Glu Asn Phe Ala Arg Val Trp Ala Thr Lys Gln Leu Pro
                580                 585                 590

gag agt att aag acg caa gta tca gtt gat gtt cac gca cca ggt cca      2245
Glu Ser Ile Lys Thr Gln Val Ser Val Asp Val His Ala Pro Gly Pro
            595                 600                 605

gaa cgt gcc aat gtt caa tca caa tgc caa gaa gaa ttt tac aag gca      2293
Glu Arg Ala Asn Val Gln Ser Gln Cys Gln Glu Glu Phe Tyr Lys Ala
        610                 615                 620

ttt gat gta act gaa cat gat ggc atg tgg ctc gat cct gaa aaa cgt      2341
Phe Asp Val Thr Glu His Asp Gly Met Trp Leu Asp Pro Glu Lys Arg
    625                 630                 635

gtt gta att tgg taataatcaa taaaataacc ttgctcagca aggttatttt          2393
Val Val Ile Trp
640

tttgccattt tagctaattt gttattttta aatgctaaag agtagttttt ttgcattgac    2453

tcctataatg aagatgacta cagtgcttgc tactacactg tggcctttat aacttatacc    2513
```

-continued

```
catataaatt tatgcactaa aaaaggctcc catttgggag cttttttag ttgttatttt   2573

aactattttg tttttgcatg ggaataatct ttaggcttaa tcctcttgat gtaagatgga   2633

tttggtttac ctaaaattaa tggtacacgc tcaatgacgg tatctgcata ttccaagccg   2693

aaccatgaag cagggttaga agacaggttt tgtaaacgaa cacgagcttc aactaaccac   2753

ttctcgt                                                             2760


<210> SEQ ID NO 4
<211> LENGTH: 643
<212> TYPE: PRT
<213> ORGANISM: Lactobacillus helveticus

<400> SEQUENCE: 4

Met Thr Val Arg Gly Gly Ala Gly Asp Ile Thr Glu Ala Asp Leu Ser
  1               5                  10                  15

Ala Arg Pro Gln Asp Asn Leu Tyr Leu Ala Val Asn Ser Glu Trp Leu
            20                  25                  30

Lys Asn Ala Lys Ile Pro Ser Asp Arg Ser Arg Thr Ser Ser Phe Asp
        35                  40                  45

Gly Ile Asp Leu Asn Ile Glu Lys Glu Leu Met Gln Asp Phe Ala Asp
    50                  55                  60

Phe Ala Asp Gly Lys Lys Asp Leu Pro Asp Val Pro Asn Phe Glu Lys
 65                  70                  75                  80

Ala Val Ala Leu Tyr Lys Ile Ala Lys Asp Phe Asp Arg Arg Asn Ala
                 85                  90                  95

Asp Gly Ala Asp Pro Ile Gln Ala Asp Leu His Glu Ile Leu Gly Leu
            100                 105                 110

Arg Asn Phe Ala Asp Phe Thr Leu Lys Ala Ala Asp Phe Phe Lys Asn
        115                 120                 125

Gly Phe Pro Met Pro Phe Asp Phe Ser Val Glu Ala Asp Met Lys Asn
    130                 135                 140

Thr Lys Ile His Ser Leu Gln Phe Gly Gly Pro Gly Thr Phe Leu Pro
145                 150                 155                 160

Asp Thr Thr Thr Tyr Lys Thr Pro Ala Ala Glu Lys Leu Leu Ala Val
                165                 170                 175

Leu Lys Glu Gln Ser Ile Asn Leu Leu Thr Met Ser Gly Ile Ser Lys
            180                 185                 190

Ser Glu Ala Glu Asp Tyr Ala Glu Lys Ala Leu Ala Tyr Asp Ala Lys
        195                 200                 205

Ile Ala Lys Val Val Lys Ser Ala Glu Glu Trp Ala Asp Tyr Pro Ala
    210                 215                 220

Thr Tyr Asn Pro Ile Ser Arg Asp Asp Phe Ala Asp Lys Phe Lys Ser
225                 230                 235                 240

Phe Lys Met Asp Tyr Phe Leu Gly Glu Leu Phe Ala Lys Lys Pro Glu
                245                 250                 255

Arg Val Ile Asn Thr Glu Pro Arg Tyr Leu Asp Tyr Ala Glu Glu Leu
            260                 265                 270

Leu Asn Glu Asp Val Phe Ala Glu Ile Lys Ala Trp Met Leu Val Lys
        275                 280                 285

Phe Val Asn Gly Val Ala Ser Ser Leu Ser Gln Glu Phe Arg Glu Ala
    290                 295                 300

Ala Phe Pro Phe Ser Gln Ala Leu Ser Gly Gln Pro Glu Leu Pro Ser
305                 310                 315                 320

Gly Val Lys Gln Ala Tyr His Ile Ala Asn Ser Asp Phe Ser Glu Val
```

-continued

```
                325                 330                 335

Val Gly Val Tyr Tyr Gly Gln Thr Tyr Phe Gly Ala Glu Ala Lys Ala
            340                 345                 350

Asp Val Thr Asp Met Ile His Lys Met Leu Asp Val Tyr Glu Lys Arg
        355                 360                 365

Ile Arg Glu Asn Ser Trp Leu Ser Gln Ala Thr Lys Asp Lys Ala Ile
    370                 375                 380

Val Lys Leu Arg Ala Leu Ile Leu Lys Ile Gly Tyr Pro Asp Lys Ile
385                 390                 395                 400

Glu Glu Ile Tyr Asp Arg Leu Thr Val Asp Pro Glu Ala Ser Leu Tyr
                405                 410                 415

Ala Asn Glu Ala Gln Phe Gly Arg Glu Gln Ile Lys Tyr Asn Leu Glu
            420                 425                 430

Lys Leu Asp Gln Asp Val Asp Arg Ser Val Trp Leu Met Pro Gly Asn
        435                 440                 445

Leu Val Asn Ala Cys Tyr Asp Pro Gln Arg Asn Asp Leu Thr Phe Pro
    450                 455                 460

Ala Ala Ile Leu Gln Lys Pro Phe Tyr Asp Leu Lys Gln Ser Arg Ser
465                 470                 475                 480

Leu Asn Tyr Gly Gly Ile Gly Val Val Ile Ala His Glu Ile Ser His
                485                 490                 495

Ala Phe Asp Asn Asn Gly Ala Gln Phe Asp Glu Phe Gly Asn Met Lys
            500                 505                 510

Asn Trp Trp Thr Glu Lys Asp Phe Ala Glu Phe Lys Lys Arg Thr Gln
        515                 520                 525

Ala Glu Ile Asp Leu Phe Asp Gly Ile Lys Tyr Gly Pro Val Thr Leu
    530                 535                 540

Asn Gly Lys Gln Ile Val Ser Glu Asn Ile Ala Asp Gln Gly Gly Leu
545                 550                 555                 560

Thr Ala Ala Val Glu Ala Asn Lys Gly Glu Asp Gly Asn Met Lys Glu
                565                 570                 575

Leu Phe Glu Asn Phe Ala Arg Val Trp Ala Thr Lys Gln Leu Pro Glu
            580                 585                 590

Ser Ile Lys Thr Gln Val Ser Val Asp Val His Ala Pro Gly Pro Glu
        595                 600                 605

Arg Ala Asn Val Gln Ser Gln Cys Gln Glu Glu Phe Tyr Lys Ala Phe
    610                 615                 620

Asp Val Thr Glu His Asp Gly Met Trp Leu Asp Pro Glu Lys Arg Val
625                 630                 635                 640

Val Ile Trp


<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Arg Pro Lys His Pro Ile Lys His Gln
  1               5


<210> SEQ ID NO 6
<211> LENGTH: 7
<212> TYPE: PRT
```

<213> ORGANISM: Artificial Sequence
<220> FEATURE:
<223> OTHER INFORMATION: Description of Artificial Sequence: Synthetic
Peptide

<400> SEQUENCE: 6

Lys His Pro Ile Lys His Gln
1 5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 7

His Pro Ile Lys His Gln
1 5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 8

Pro Ile Lys His Gln
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 9

Arg Pro Lys His Pro Ile Lys
1 5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 10

His Pro Ile Lys
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 11

Arg Pro Lys His Pro
1 5

```
<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 12

Tyr Gln Glu Pro Val Leu Gly Pro Val Arg Gly Pro Phe Pro Ile Ile
  1               5                  10                  15

Val


<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 13

Gln Glu Pro Val Leu Gly Pro Val Arg Gly Pro Phe Pro Ile Ile Val
  1               5                  10                  15


<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 14

Glu Pro Val Leu Gly Pro Val Arg Gly Pro Phe Pro Ile Ile Val
  1               5                  10                  15


<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 15

Val Leu Gly Pro Val Arg Gly Pro Phe Pro Ile Ile Val
  1               5                  10


<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 16

Gly Pro Val Arg Gly Pro Phe Pro Ile Ile Val
  1               5                  10


<210> SEQ ID NO 17
<211> LENGTH: 9
<212> TYPE: PRT
<213> ORGANISM: Artificial Sequence
<220> FEATURE:
```

```
<223> OTHER INFORMATION: Description of Artificial Sequence:  Synthetic
      Peptide

<400> SEQUENCE: 17

Val Arg Gly Pro Phe Pro Ile Ile Val
  1               5


<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Tyr Gln Glu Pro Val Leu Gly Pro Val Arg Gly Pro Phe Pro Ile Ile
  1               5                  10                  15


<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 19

Tyr Gln Glu Pro Val Leu Gly Pro Val Arg Gly Pro Phe Pro
  1               5                  10


<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 20

Gln Glu Pro Val Leu Gly Pro Val Arg Gly Pro Phe Pro
  1               5                  10


<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 21

Val Leu Gly Pro Val Arg Gly Pro Phe Pro
  1               5                  10


<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 22

Gly Pro Val Arg Gly Pro Phe Pro
  1               5
```

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 23

Tyr Gln Glu Pro Val Leu Gly Pro Val Arg Gly Pro
1 5 10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 24

Gln Glu Pro Val Leu Gly Pro Val Arg Gly Pro
1 5 10

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic Primer

<400> SEQUENCE: 25
gatgcgattg cactcg 16

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic Primer

<400> SEQUENCE: 26
gatagcggca gggaag 16

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic Primer

<400> SEQUENCE: 27
gttttcggtt tgcttttg 18

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic Primer

<400> SEQUENCE: 28
cggcatctct tttggc 16

```
<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 29

ggacgatcgg caggg                                                    15


<210> SEQ ID NO 30
<211> LENGTH: 2580
<212> TYPE: DNA
<213> ORGANISM: Lactobacillus helveticus
<220> FEATURE:
<221> NAME/KEY: CDS
<222> LOCATION: (295)..(2091)

<400> SEQUENCE: 30

atgcttaagg gagttcggag catacagctt ataccaagaa cgacaaatat tgtttaaacg     60

agtaaaacta acttgtaaat gatgagaaaa actcttaagc ttaagatagt tcaatctagt    120

cagactcttt tctattatta ctatttacaa gtcgagtcta acaagattgg actttttatt    180

taactaaaac gatttaacta gcaccacgcg tattattaat aataacttat tttttgtgtt    240

tcattgtaca ttgaattatg atgtatacaa aatgtaatta atggaggaaa attt atg      297
                                                            Met
                                                              1

gcg att cca aca aga agc gaa gtc cca gaa gat ttg aag tgg gat tta      345
Ala Ile Pro Thr Arg Ser Glu Val Pro Glu Asp Leu Lys Trp Asp Leu
              5                  10                  15

acc cgc atc ttt aaa aca gac caa gac tgg gaa aat gcc ttt gac aag      393
Thr Arg Ile Phe Lys Thr Asp Gln Asp Trp Glu Asn Ala Phe Asp Lys
         20                  25                  30

gca aaa gat gac gtg gct aag cta agt gaa tta aag gga agc ttg gct      441
Ala Lys Asp Asp Val Ala Lys Leu Ser Glu Leu Lys Gly Ser Leu Ala
     35                  40                  45

aaa tca ggc aaa gat ttg tat gaa ggc ttg acc aag att ttg gca gtt      489
Lys Ser Gly Lys Asp Leu Tyr Glu Gly Leu Thr Lys Ile Leu Ala Val
 50                  55                  60                  65

aaa cgt gat gta gaa aat att tac gtt tat gcc act atg tct agc gat      537
Lys Arg Asp Val Glu Asn Ile Tyr Val Tyr Ala Thr Met Ser Ser Asp
                 70                  75                  80

gtt gat act tct aac tca cat tat ttg ggc tac gtt agc cgc gtg caa      585
Val Asp Thr Ser Asn Ser His Tyr Leu Gly Tyr Val Ser Arg Val Gln
             85                  90                  95

agc ttg tcc aat caa ttt gaa gca aca acc agt ttt att aat cct gaa      633
Ser Leu Ser Asn Gln Phe Glu Ala Thr Thr Ser Phe Ile Asn Pro Glu
        100                 105                 110

att ttg agt atc cct gcc gaa aag ttt gaa caa ttc aaa aaa gac gag      681
Ile Leu Ser Ile Pro Ala Glu Lys Phe Glu Gln Phe Lys Lys Asp Glu
    115                 120                 125

cca aga tta gct gat tac gcc cac tat ttg gaa atg atc act aac aag      729
Pro Arg Leu Ala Asp Tyr Ala His Tyr Leu Glu Met Ile Thr Asn Lys
130                 135                 140                 145

cgt cct cat act ttg cca gca gaa gaa gaa aaa att atc gct gac gca      777
Arg Pro His Thr Leu Pro Ala Glu Glu Glu Lys Ile Ile Ala Asp Ala
                150                 155                 160

ggg gat gct atg agc gtg tca gag aat acc ttt aac gtt tta acc aac      825
Gly Asp Ala Met Ser Val Ser Glu Asn Thr Phe Asn Val Leu Thr Asn
            165                 170                 175
```

-continued

```
tct gac atg gaa tat ggt tat gtg caa gat gaa gac ggc aac atg gag      873
Ser Asp Met Glu Tyr Gly Tyr Val Gln Asp Glu Asp Gly Asn Met Glu
        180                 185                 190

caa tta tcc aat ggc ttg tat tca tta ttg att cag tcc caa aat cgt      921
Gln Leu Ser Asn Gly Leu Tyr Ser Leu Leu Ile Gln Ser Gln Asn Arg
    195                 200                 205

gac gtg cgt aaa ggt gct ttt aat act ctc tat gcc agc tat ggt caa      969
Asp Val Arg Lys Gly Ala Phe Asn Thr Leu Tyr Ala Ser Tyr Gly Gln
210                 215                 220                 225

ttc caa aac tcg ctt gcc tct act ctc tcc ggc gtt gtg aaa aaa cat     1017
Phe Gln Asn Ser Leu Ala Ser Thr Leu Ser Gly Val Val Lys Lys His
                230                 235                 240

aac tac aac gca cgc atg cac aag tat gat tca gct cgt gaa gcc gca     1065
Asn Tyr Asn Ala Arg Met His Lys Tyr Asp Ser Ala Arg Glu Ala Ala
            245                 250                 255

tta gct gat aac ggc gta cct gtt gaa gtt tac gac aca tta att aaa     1113
Leu Ala Asp Asn Gly Val Pro Val Glu Val Tyr Asp Thr Leu Ile Lys
        260                 265                 270

gaa gtt gat tca cac ctt gac ttg ctt cac cgt tat gtc gca ttg cgc     1161
Glu Val Asp Ser His Leu Asp Leu Leu His Arg Tyr Val Ala Leu Arg
    275                 280                 285

aag aaa att tta ggt ctt aaa gac tta caa atg tgg gac atg tac gtg     1209
Lys Lys Ile Leu Gly Leu Lys Asp Leu Gln Met Trp Asp Met Tyr Val
290                 295                 300                 305

ccg cta act ggt aag cct gct ttg tct tac aac ttt gaa gag gct aaa     1257
Pro Leu Thr Gly Lys Pro Ala Leu Ser Tyr Asn Phe Glu Glu Ala Lys
                310                 315                 320

aag gta gct aaa gaa gcc atg aag cca ctt ggc gaa gac tac tta aag     1305
Lys Val Ala Lys Glu Ala Met Lys Pro Leu Gly Glu Asp Tyr Leu Lys
            325                 330                 335

cat gtt gat tat att ttt aac aac cgt gtg att gat cct gtt gaa tct     1353
His Val Asp Tyr Ile Phe Asn Asn Arg Val Ile Asp Pro Val Glu Ser
        340                 345                 350

aag ggc aag gtt act ggt gct tac tct ggt ggt gct tac gat acc gat     1401
Lys Gly Lys Val Thr Gly Ala Tyr Ser Gly Gly Ala Tyr Asp Thr Asp
    355                 360                 365

cca tat gaa ctt ttg aac tgg gaa gac aat atc gat tca ctc tat act     1449
Pro Tyr Glu Leu Leu Asn Trp Glu Asp Asn Ile Asp Ser Leu Tyr Thr
370                 375                 380                 385

tta gtt cat gaa act gga cac tca gtt cac tct tgg tac acc cgc cac     1497
Leu Val His Glu Thr Gly His Ser Val His Ser Trp Tyr Thr Arg His
                390                 395                 400

agt cag cct tat atc tat ggt aat tac cca atc ttc gtg gct gaa att     1545
Ser Gln Pro Tyr Ile Tyr Gly Asn Tyr Pro Ile Phe Val Ala Glu Ile
            405                 410                 415

gct tca acc act aat gaa aat att ttg act gaa tat ttc ttg gac cat     1593
Ala Ser Thr Thr Asn Glu Asn Ile Leu Thr Glu Tyr Phe Leu Asp His
        420                 425                 430

atc act gat cct aag acg cgc gca ttc atc ttg aac cac tac ctt gat     1641
Ile Thr Asp Pro Lys Thr Arg Ala Phe Ile Leu Asn His Tyr Leu Asp
    435                 440                 445

tca ttc aag ggt aca ttg ttc cgc caa act caa ttt gcg gta ttt gaa     1689
Ser Phe Lys Gly Thr Leu Phe Arg Gln Thr Gln Phe Ala Val Phe Glu
450                 455                 460                 465

caa ttt atc cac gaa gca gat gct aag ggc gaa cca ttg act gcc gat     1737
Gln Phe Ile His Glu Ala Asp Ala Lys Gly Glu Pro Leu Thr Ala Asp
                470                 475                 480

att ttg gat gat gtt tat ggt caa att aac cag cat tac tac ggc gac     1785
Ile Leu Asp Asp Val Tyr Gly Gln Ile Asn Gln His Tyr Tyr Gly Asp
```

-continued

```
            485                 490                 495

agt gtt gaa cct ggt ggc gat att gcg ctt gaa tgg tca cga att ccg      1833
Ser Val Glu Pro Gly Gly Asp Ile Ala Leu Glu Trp Ser Arg Ile Pro
        500                 505                 510

cac ttc tac tac aac ttc tac gtt tat caa tat gcg act gga ttt gcg      1881
His Phe Tyr Tyr Asn Phe Tyr Val Tyr Gln Tyr Ala Thr Gly Phe Ala
    515                 520                 525

gct gca acg gct ttg gct aac aag gtt gtg cat ggt agt cag gct gat      1929
Ala Ala Thr Ala Leu Ala Asn Lys Val Val His Gly Ser Gln Ala Asp
530                 535                 540                 545

agg gat gca tac ctg ggc tac ctt aag tca ggt tct agt gac tat cct      1977
Arg Asp Ala Tyr Leu Gly Tyr Leu Lys Ser Gly Ser Ser Asp Tyr Pro
                550                 555                 560

act gag atc atg aag cgt gcc ggc gtt gac atg act aag ccc gat tat      2025
Thr Glu Ile Met Lys Arg Ala Gly Val Asp Met Thr Lys Pro Asp Tyr
            565                 570                 575

ttg aaa gat gct ttc aag act ttt gaa aag aga ttg aac gaa ttc gag      2073
Leu Lys Asp Ala Phe Lys Thr Phe Glu Lys Arg Leu Asn Glu Phe Glu
        580                 585                 590

agt ttg att ggt aag taa ttcatgcagg cttattctcc agattatatt            2121
Ser Leu Ile Gly Lys
    595

agagatgctt tagtccgttt tgcctagcac tcaaatgcaa tttaaggtaa ttcattatcg   2181

ctcgggcaaa cggaagccat tgttttatac gacagagtaa cttttgtgaa taataaaggc   2241

gttaagctac gtgatattta cgaagccagt aatcaaaaag atgcattcta tctaatgctc   2301

aatatggcta acaataatgc ggaattaacc attgataata ttttgaaatt acaataattt   2361

gaattaacta aaaataccat tagtactgca ggtaaattca aacaaaatga aaatatgatc   2421

ttaggtgctg atttccaaac ttcttccgta gctgagactc ctattgctgt caaacaatgg   2481

gcagaaaata ccaattatcg tctagaaaac agtcaaacta aagatgaatt cctccaaaat   2541

ctgatggctg cacatattaa ttttgaacga attcatccc                          2580


<210> SEQ ID NO 31
<211> LENGTH: 598
<212> TYPE: PRT
<213> ORGANISM: Lactobacillus helveticus

<400> SEQUENCE: 31

Met Ala Ile Pro Thr Arg Ser Glu Val Pro Glu Asp Leu Lys Trp Asp
  1               5                  10                  15

Leu Thr Arg Ile Phe Lys Thr Asp Gln Asp Trp Glu Asn Ala Phe Asp
            20                  25                  30

Lys Ala Lys Asp Asp Val Ala Lys Leu Ser Glu Leu Lys Gly Ser Leu
        35                  40                  45

Ala Lys Ser Gly Lys Asp Leu Tyr Glu Gly Leu Thr Lys Ile Leu Ala
     50                  55                  60

Val Lys Arg Asp Val Glu Asn Ile Tyr Val Tyr Ala Thr Met Ser Ser
 65                  70                  75                  80

Asp Val Asp Thr Ser Asn Ser His Tyr Leu Gly Tyr Val Ser Arg Val
                85                  90                  95

Gln Ser Leu Ser Asn Gln Phe Glu Ala Thr Thr Ser Phe Ile Asn Pro
            100                 105                 110

Glu Ile Leu Ser Ile Pro Ala Glu Lys Phe Glu Gln Phe Lys Lys Asp
        115                 120                 125

Glu Pro Arg Leu Ala Asp Tyr Ala His Tyr Leu Glu Met Ile Thr Asn
```

-continued

```
    130                 135                 140

Lys Arg Pro His Thr Leu Pro Ala Glu Glu Glu Lys Ile Ile Ala Asp
145                 150                 155                 160

Ala Gly Asp Ala Met Ser Val Ser Glu Asn Thr Phe Asn Val Leu Thr
                165                 170                 175

Asn Ser Asp Met Glu Tyr Gly Tyr Val Gln Asp Glu Asp Gly Asn Met
            180                 185                 190

Glu Gln Leu Ser Asn Gly Leu Tyr Ser Leu Leu Ile Gln Ser Gln Asn
        195                 200                 205

Arg Asp Val Arg Lys Gly Ala Phe Asn Thr Leu Tyr Ala Ser Tyr Gly
    210                 215                 220

Gln Phe Gln Asn Ser Leu Ala Ser Thr Leu Ser Gly Val Val Lys Lys
225                 230                 235                 240

His Asn Tyr Asn Ala Arg Met His Lys Tyr Asp Ser Ala Arg Glu Ala
                245                 250                 255

Ala Leu Ala Asp Asn Gly Val Pro Val Glu Val Tyr Asp Thr Leu Ile
            260                 265                 270

Lys Glu Val Asp Ser His Leu Asp Leu Leu His Arg Tyr Val Ala Leu
        275                 280                 285

Arg Lys Lys Ile Leu Gly Leu Lys Asp Leu Gln Met Trp Asp Met Tyr
    290                 295                 300

Val Pro Leu Thr Gly Lys Pro Ala Leu Ser Tyr Asn Phe Glu Glu Ala
305                 310                 315                 320

Lys Lys Val Ala Lys Glu Ala Met Lys Pro Leu Gly Glu Asp Tyr Leu
                325                 330                 335

Lys His Val Asp Tyr Ile Phe Asn Asn Arg Val Ile Asp Pro Val Glu
            340                 345                 350

Ser Lys Gly Lys Val Thr Gly Ala Tyr Ser Gly Gly Ala Tyr Asp Thr
        355                 360                 365

Asp Pro Tyr Glu Leu Leu Asn Trp Glu Asp Asn Ile Asp Ser Leu Tyr
    370                 375                 380

Thr Leu Val His Glu Thr Gly His Ser Val His Ser Trp Tyr Thr Arg
385                 390                 395                 400

His Ser Gln Pro Tyr Ile Tyr Gly Asn Tyr Pro Ile Phe Val Ala Glu
                405                 410                 415

Ile Ala Ser Thr Thr Asn Glu Asn Ile Leu Thr Glu Tyr Phe Leu Asp
            420                 425                 430

His Ile Thr Asp Pro Lys Thr Arg Ala Phe Ile Leu Asn His Tyr Leu
        435                 440                 445

Asp Ser Phe Lys Gly Thr Leu Phe Arg Gln Thr Gln Phe Ala Val Phe
    450                 455                 460

Glu Gln Phe Ile His Glu Ala Asp Ala Lys Gly Glu Pro Leu Thr Ala
465                 470                 475                 480

Asp Ile Leu Asp Asp Val Tyr Gly Gln Ile Asn Gln His Tyr Tyr Gly
                485                 490                 495

Asp Ser Val Glu Pro Gly Gly Asp Ile Ala Leu Glu Trp Ser Arg Ile
            500                 505                 510

Pro His Phe Tyr Tyr Asn Phe Tyr Val Tyr Gln Tyr Ala Thr Gly Phe
        515                 520                 525

Ala Ala Ala Thr Ala Leu Ala Asn Lys Val Val His Gly Ser Gln Ala
    530                 535                 540

Asp Arg Asp Ala Tyr Leu Gly Tyr Leu Lys Ser Gly Ser Ser Asp Tyr
545                 550                 555                 560
```

-continued

```
Pro Thr Glu Ile Met Lys Arg Ala Gly Val Asp Met Thr Lys Pro Asp
                565                 570                 575

Tyr Leu Lys Asp Ala Phe Lys Thr Phe Glu Lys Arg Leu Asn Glu Phe
            580                 585                 590

Glu Ser Leu Ile Gly Lys
        595


<210> SEQ ID NO 32
<211> LENGTH: 2320
<212> TYPE: DNA
<213> ORGANISM: Lactobacillus helveticus
<220> FEATURE:
<221> NAME/KEY: CDS
<222> LOCATION: (504)..(1817)

<400> SEQUENCE: 32

gacaagatct ttgttgttgt aaaagacact aagaatcaaa aagttactgt ttataacaag      60

aacgctaaga aaaccagcaa aaaagttgct atgggttcaa cttacaccgc taaagcagtt     120

aagaaagttc acagcactaa gattgttaga attaacaaga gtcaatggtt gaacaccaag     180

gacgttgtaa aggactaata gagcaaggaa taaacttaga ttaacagttt taatgatctc     240

agactatttc tgttttcaaa ctcttggatt aggaaaatta aaggacaaag atattcgaaa     300

tgaatgtctt tgtctttttt gatacaataa agacgccgct ttagctcaat aggtagagca     360

ccgccgtggt aaggaggagg tccccagttc aaacctggga agcggctttg attgaagggc     420

taaacaagtc cttttttca tagctaaaat aatgctaaaa tgatggcact gaattgaatg     480

attttatcga gaaaggaaaa tct atg aaa cac gaa ctt aca atg gca gaa att     533
                           Met Lys His Glu Leu Thr Met Ala Glu Ile
                             1               5                  10

gcc aag ttt caa caa gaa tat aaa aaa gaa cca caa aat cga gta gca      581
Ala Lys Phe Gln Gln Glu Tyr Lys Lys Glu Pro Gln Asn Arg Val Ala
                15                  20                  25

gaa cta gca gtt gta aat aat ggc gtt caa aaa gct agt ttt aat act      629
Glu Leu Ala Val Val Asn Asn Gly Val Gln Lys Ala Ser Phe Asn Thr
            30                  35                  40

gaa gga atc aga aag ctt aac cgt act ttc tca att gaa att cct act      677
Glu Gly Ile Arg Lys Leu Asn Arg Thr Phe Ser Ile Glu Ile Pro Thr
        45                  50                  55

gat aat gta act gat caa aag caa tct gga cgc tgc tgg ttg ttt gcg      725
Asp Asn Val Thr Asp Gln Lys Gln Ser Gly Arg Cys Trp Leu Phe Ala
    60                  65                  70

gca tta aac act ttg cgt cat gga ttt gct aag aag tac aac acc aag      773
Ala Leu Asn Thr Leu Arg His Gly Phe Ala Lys Lys Tyr Asn Thr Lys
 75                 80                  85                  90

aat ttt act ttt tct caa aat tat ctc ttc ttc tgg gat aga gtg gaa      821
Asn Phe Thr Phe Ser Gln Asn Tyr Leu Phe Phe Trp Asp Arg Val Glu
                95                 100                 105

aga gca aat att ttc ttt gat aat atc tta aat act gca gat aaa ccg      869
Arg Ala Asn Ile Phe Phe Asp Asn Ile Leu Asn Thr Ala Asp Lys Pro
            110                 115                 120

ctt ggt gac aga acc gtt cac act tat atg cag ggc cct gac gct gat      917
Leu Gly Asp Arg Thr Val His Thr Tyr Met Gln Gly Pro Asp Ala Asp
        125                 130                 135

ggt ggt caa tgg gca atg gct gtg tca ttg atc cgc aag tat ggt tta      965
Gly Gly Gln Trp Ala Met Ala Val Ser Leu Ile Arg Lys Tyr Gly Leu
    140                 145                 150

gtg cca act tac gca caa gaa gaa agc ttt act gca aac aat acc gct     1013
Val Pro Thr Tyr Ala Gln Glu Glu Ser Phe Thr Ala Asn Asn Thr Ala
```

-continued

```
155                 160                 165                 170

gcc ttc aac cgt gca ttg aac atg aag ctg cgt gaa gat ggc tta att     1061
Ala Phe Asn Arg Ala Leu Asn Met Lys Leu Arg Glu Asp Gly Leu Ile
            175                 180                 185

ttg cgt aaa tta gct aag gaa aat aaa acc gat gaa att gaa aca aag     1109
Leu Arg Lys Leu Ala Lys Glu Asn Lys Thr Asp Glu Ile Glu Thr Lys
            190                 195                 200

cgt caa gaa ttc ttg agc gaa gtt tac cgc atg gct gtc att gcc ttt     1157
Arg Gln Glu Phe Leu Ser Glu Val Tyr Arg Met Ala Val Ile Ala Phe
        205                 210                 215

ggt gaa cct gtt caa aaa ttt gat ctt gaa ttc aag gat gac gat ggc     1205
Gly Glu Pro Val Gln Lys Phe Asp Leu Glu Phe Lys Asp Asp Asp Gly
    220                 225                 230

aag tac cac ttt gat ggt gat tta act cca ctt gat ttc ttc cat aat     1253
Lys Tyr His Phe Asp Gly Asp Leu Thr Pro Leu Asp Phe Phe His Asn
235                 240                 245                 250

tac ttt aca gat gat ctt gat gat tat att gtt ttg ttc aat gcg cca     1301
Tyr Phe Thr Asp Asp Leu Asp Asp Tyr Ile Val Leu Phe Asn Ala Pro
            255                 260                 265

gat cat gaa ttt gat aag ctt tat gct ttg cca ttt gag gat aat gtt     1349
Asp His Glu Phe Asp Lys Leu Tyr Ala Leu Pro Phe Glu Asp Asn Val
            270                 275                 280

gaa ggc ggc act cct gtc caa ttt ttg aat act gaa att gac aac tta     1397
Glu Gly Gly Thr Pro Val Gln Phe Leu Asn Thr Glu Ile Asp Asn Leu
        285                 290                 295

aaa gag gct gca att aag caa ctt gaa gct ggt gaa act atc tgg ttt     1445
Lys Glu Ala Ala Ile Lys Gln Leu Glu Ala Gly Glu Thr Ile Trp Phe
    300                 305                 310

ggc tgt gat gtt ggc aaa gac agt gat cgt caa aag ggt atc ttg tct     1493
Gly Cys Asp Val Gly Lys Asp Ser Asp Arg Gln Lys Gly Ile Leu Ser
315                 320                 325                 330

aaa ggc ctt tac caa act gat act att ttt aat att gaa acc aaa tta     1541
Lys Gly Leu Tyr Gln Thr Asp Thr Ile Phe Asn Ile Glu Thr Lys Leu
            335                 340                 345

tcc aag aag gaa cgc ttg caa act ggt gct tct ggt tca act cat gcc     1589
Ser Lys Lys Glu Arg Leu Gln Thr Gly Ala Ser Gly Ser Thr His Ala
            350                 355                 360

atg acg cta gtc ggt gtt gat gta gtt gat ggc aag ccg cgt caa tgg     1637
Met Thr Leu Val Gly Val Asp Val Val Asp Gly Lys Pro Arg Gln Trp
        365                 370                 375

aag att gaa aac tca tgg ggt gca aaa gtt ggt gaa aag ggc tac ttt     1685
Lys Ile Glu Asn Ser Trp Gly Ala Lys Val Gly Glu Lys Gly Tyr Phe
    380                 385                 390

gtc atg gat gat gac tgg ttc aac gaa tat ctc ttc aag gta gtt gtt     1733
Val Met Asp Asp Asp Trp Phe Asn Glu Tyr Leu Phe Lys Val Val Val
395                 400                 405                 410

aag aag caa tat gtt cca gat aaa tta gtt aaa atc tgg gaa ggc gaa     1781
Lys Lys Gln Tyr Val Pro Asp Lys Leu Val Lys Ile Trp Glu Gly Glu
            415                 420                 425

gca act cca gta gaa gca tgg gac tca atg gca taa tggatatcaa          1827
Ala Thr Pro Val Glu Ala Trp Asp Ser Met Ala
            430                 435

tgcagtaatt gaatttacca agaatcagct gaaagatgaa aagactggtc atgattttta   1887

tcatggtgaa cgcgtagctc atttagccag caagatgtat ctagctgatc acgagtcagc   1947

acatgaagat agccgtgagg tagcgattat taagactgct gcttatctgc atgatacgat   2007

tgatgaaaaa atctgtgctg attccgaaaa ggtggttaaa gaaatagatg aattattgcc   2067

tcaagttggc tttaacgacc tagaagtttg ggatattctt tataccattc agcatatgtc   2127
```

-continued

```
tttttcagca aatattgagc atcactatca tttgccatta tctgggcaat acgtgcaaga   2187

tgcagatcgc ttggagagtc ttggcgcaat tggaattgct cgtgctttta cctacggcgg   2247

aaagcatggc aacaagattc atgatcctga gattaaacct gagaagctag ttagtcatga   2307

tcaatatcgt aat                                                      2320


<210> SEQ ID NO 33
<211> LENGTH: 437
<212> TYPE: PRT
<213> ORGANISM: Lactobacillus helveticus

<400> SEQUENCE: 33

Met Lys His Glu Leu Thr Met Ala Glu Ile Ala Lys Phe Gln Gln Glu
  1               5                  10                  15

Tyr Lys Lys Glu Pro Gln Asn Arg Val Ala Glu Leu Ala Val Val Asn
             20                  25                  30

Asn Gly Val Gln Lys Ala Ser Phe Asn Thr Glu Gly Ile Arg Lys Leu
         35                  40                  45

Asn Arg Thr Phe Ser Ile Glu Ile Pro Thr Asp Asn Val Thr Asp Gln
     50                  55                  60

Lys Gln Ser Gly Arg Cys Trp Leu Phe Ala Ala Leu Asn Thr Leu Arg
 65                  70                  75                  80

His Gly Phe Ala Lys Lys Tyr Asn Thr Lys Asn Phe Thr Phe Ser Gln
                 85                  90                  95

Asn Tyr Leu Phe Phe Trp Asp Arg Val Glu Arg Ala Asn Ile Phe Phe
            100                 105                 110

Asp Asn Ile Leu Asn Thr Ala Asp Lys Pro Leu Gly Asp Arg Thr Val
        115                 120                 125

His Thr Tyr Met Gln Gly Pro Asp Ala Asp Gly Gly Gln Trp Ala Met
    130                 135                 140

Ala Val Ser Leu Ile Arg Lys Tyr Gly Leu Val Pro Thr Tyr Ala Gln
145                 150                 155                 160

Glu Glu Ser Phe Thr Ala Asn Asn Thr Ala Ala Phe Asn Arg Ala Leu
                165                 170                 175

Asn Met Lys Leu Arg Glu Asp Gly Leu Ile Leu Arg Lys Leu Ala Lys
            180                 185                 190

Glu Asn Lys Thr Asp Glu Ile Glu Thr Lys Arg Gln Glu Phe Leu Ser
        195                 200                 205

Glu Val Tyr Arg Met Ala Val Ile Ala Phe Gly Glu Pro Val Gln Lys
    210                 215                 220

Phe Asp Leu Glu Phe Lys Asp Asp Asp Gly Lys Tyr His Phe Asp Gly
225                 230                 235                 240

Asp Leu Thr Pro Leu Asp Phe Phe His Asn Tyr Phe Thr Asp Asp Leu
                245                 250                 255

Asp Asp Tyr Ile Val Leu Phe Asn Ala Pro Asp His Glu Phe Asp Lys
            260                 265                 270

Leu Tyr Ala Leu Pro Phe Glu Asp Asn Val Glu Gly Gly Thr Pro Val
        275                 280                 285

Gln Phe Leu Asn Thr Glu Ile Asp Asn Leu Lys Glu Ala Ala Ile Lys
    290                 295                 300

Gln Leu Glu Ala Gly Glu Thr Ile Trp Phe Gly Cys Asp Val Gly Lys
305                 310                 315                 320

Asp Ser Asp Arg Gln Lys Gly Ile Leu Ser Lys Gly Leu Tyr Gln Thr
                325                 330                 335
```

```
Asp Thr Ile Phe Asn Ile Glu Thr Lys Leu Ser Lys Lys Glu Arg Leu
            340                 345                 350

Gln Thr Gly Ala Ser Gly Ser Thr His Ala Met Thr Leu Val Gly Val
        355                 360                 365

Asp Val Val Asp Gly Lys Pro Arg Gln Trp Lys Ile Glu Asn Ser Trp
    370                 375                 380

Gly Ala Lys Val Gly Glu Lys Gly Tyr Phe Val Met Asp Asp Asp Trp
385                 390                 395                 400

Phe Asn Glu Tyr Leu Phe Lys Val Val Val Lys Lys Gln Tyr Val Pro
                405                 410                 415

Asp Lys Leu Val Lys Ile Trp Glu Gly Glu Ala Thr Pro Val Glu Ala
            420                 425                 430

Trp Asp Ser Met Ala
        435


<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:  Synthetic
      peptide
<220> FEATURE:
<221> NAME/KEY: MOD_RES
<222> LOCATION: (3)..(4)
<223> OTHER INFORMATION: x = any natural occurring amino acid

<400> SEQUENCE: 34

His Glu Xaa Xaa His
  1               5


<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 35

His Glu Ile Ser His
  1               5


<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 36

cgggatcctt ttgactttgg gtgaat                                          26


<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 37

cgggatccct taagggagtt cggag                                           25
```

```
<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 38

cgggatccta taacaagaac gctaagaa                                        28


<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 39

tcccccggga ttagattaag caag                                            24


<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 40

ggggtaccac gagaagtggt tagttga                                         27


<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 41

ggggtacctt ggaggaattc atctttag                                        28


<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 42

ggggtaccca gataatggca aatgata                                         27


<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 43

gctctagaga aattcgccct ggtc                                            24
```

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
ggggtaccga ctttgggtga atc 23

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cgggatccca ttttattatt caaagagaa 29

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
cgggatcccc aacaagaagc gaagtc 26

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gctggagctc gtcagctttt tgtatgg 27

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cgcggatcca atttagcaaa aatc 24

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
gctctagatc aattatataa ctgatac 27

-continued

```
<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 50

cgggatccga attaactgtg cagg                                             24


<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 51

gctctagaga aattcgccct ggtc                                             24
```

METHODS AND COMPOSITIONS INVOLVING ENDOPEPTIDASES PEPO2 AND PEPO3

BACKGROUND OF THE INVENTION

This application claims the benefit of priority to U.S. Provisional Patent Application Ser. No. 60/480,536 filed Jun. 20, 2003, which is hereby incorporated by reference in its entirety.

1. Field of the Invention

This invention was made with government support under grant number 99-CRHF-0-6055 awarded by the United States Department of Agriculture/CREES. The government has certain rights in the invention.

The present invention relates generally to the fields of microbiology and enzymology. More particularly, it concerns methods and compositions involving endopeptidase enzymes from bacteria that cleave peptides, particularly bitter peptides and peptides involved in gluten inflammation. In some embodiments, methods and compositions concern PepO2 and/or PepO3, and their use in reducing bitterness in foods, such as cheese, or treating or preventing celiac sprue.

2. Description of Related Art

*Lactobacillus helveticus* belongs to a group of organisms known as lactic acid bacteria (LAB), which are defined by the production of lactic acid as a major product of carbohydrate fermentation. *Lb. helveticus* has multiple amino acid (AA) auxotrophies and thus is dependent on transport of AA and/or transport and hydrolysis of exogenous peptides to satisfy these nutritional requirements. In AA defined media, *Lb. helveticus* CNRZ32 can grow without Ala, Asn, Cys, Gln, Gly, and Ser when they are absent individually (Christensen, 2000). The fermentation of *Bos taurus* milk is a common system to study the proteolytic system and physiology of *Lb. helveticus*, providing a relatively consistent environment and well characterized set of proteins as a starting point, as well as having adaptive significance for dairy related LAB. Since all of the identified peptidases of *L. helveticus* are believed to be intracellular, the acquisition of AA is also likely to be dependent on the activity of at least one extracellular proteinase capable of hydrolyzing caseins into transportable peptides (Kunji et al., 1996). Therefore, obtaining AA through the hydrolysis of caseins (the preferentially hydrolyzed milk proteins) requires a complex proteolytic system comprised of proteinase(s), endopeptidase(s), aminopeptidase(s), tripeptidase(s), dipeptidase(s), and peptide transport systems (Christensen et al., 1999; Kunji et al., 1996; Pritchard and Coolbear, 1993).

The proteolytic systems of dairy LAB have received extensive research attention due to their importance in the physiology of these organisms and cheese flavor development. Because LAB are fastidious microorganisms with multiple amino acid auxotrophies (Kok and De Vos, 1994), during growth in milk, LAB rely on their proteolytic systems to obtain essential amino acids from caseins (CNs), the most abundant proteins in milk (Christensen et al., 1999; Kunji et al., 1996). In many cheese varieties, enzymatic conversion of large, casein (CN)-derived peptides into small peptides and free amino acids by LAB has pronounced effects on cheese flavor development as well as cheese functional properties. Additionally, proteolytic enzymes from LAB produce flavor compounds and precursors that are essential for cheese flavor development (Christensen et al, 1999; Mulholland, 1997).

Proteolytic systems of LAB can be functionally divided into three components: (i) cell envelope-associated proteinases which hydrolyze caseins to oligopeptides; (ii) peptide transport systems, of which the oligopeptide transport system is of greatest importance in milk and cheese; (iii) and numerous intracellular peptidases (Christensen et al., 1999; Kunji et al., 1996). The intracellular peptidases of LAB consist of both endopeptidases and aminopeptidases. Endopeptidases, due to their ability to hydrolyze peptide bonds within a peptide, are of particular interest in targeting peptides for rapid hydrolysis. Both the peptides $\alpha_{S1}$-CN(f1-9) and β-CN(f193-209), as well as other related hydrophobic peptide derivatives, are known to accumulate and have been associated with bitter defects in ripened cheeses (Broadbent et al., 2002; Broadbent et al., 1998; Exterkate and Alting, 1995; Kaminogawa et al., 1986; Lee et al., 1996; Lemieux and Simard, 1991). The peptide β-CN(f193-209) is produced by the activity of chymosin on β-CN.

Interest in the proteolytic system of *L. helveticus* CNRZ32 is related to the organism's ability to reduce bitterness and accelerate cheese flavor development when used as an adjunct culture in Gouda cheese production (Bartels et al., 1987a; Bartels et al., 1987b). The ability of *Lb. helveticus* CNRZ32 to accelerate cheese ripening and reduce bitterness when used as an adjunct culture is well documented (Bartels et al., 1987a; Bartels et al., 1987b; Madkor et al., 2000). *Lb. helveticus* CNRZ32 has been demonstrated to efficiently hydrolyze casein, and comparison with the peptidolytic activities of *Lb. helveticus* ATCC 10797 and *Lactobacillus delbrueckii* ssp. *bulgaricus* ATCC 12278 demonstrated that *Lb. helveticus* CNRZ32 had higher general aminopeptidase and dipeptidase activities (Khalid et al., 1991).

The reduction of bitterness in cheese is believed to be the result of preferential hydrolysis of low molecular weight hydrophobic peptides known to cause bitterness, rather than lack of formation of bitter peptides from high molecular weight non-bitter casein derived peptides (Broadbent et al., 1998; Gomez et al., 1996; Lee et al., 1996; Lemieux and Simard, 1991). These bitter peptides contain the amino acid proline, which forms an imino, not amino bond, making these peptides more difficult to cleave. While numerous enzymes of the proteolytic system of *Lb. helveticus* have been identified (Christensen et al., 1999), the understanding of the specific enzymes responsible for this strain's ability to reduce of bitterness in cheese is incomplete. Thus, identification and characterization of these enzymes are needed.

Moreover, endopeptidases in other contexts have also been explored. A prolyl endopeptidase was used to reduce the antigencity of a peptide involved in celiac sprue, an inflammation of the small intestine (Shan et al. 2002; Vader et al., 2002). Celiac sprue involves gluten peptides that survive the digestion process and reach the small intestine because they contain proline (see Schuppan et al., 2002). The use of other prolyl endopeptidases could provide therapeutic benefits for patients with celiac sprue.

SUMMARY OF THE INVENTION

The present invention is based on the isolation and characterization of novel endopeptidases, PepO2 (also referred to as PEPO2) and PepO3 (also referred to as PEPO3), each of which has activity in hydrolyzing proline-containing peptides, such as those that contribute to bitter taste in food, for example, cheese and those involved in celiac sprue. These enzymes have post-proline specificity, which has significant advantages. The present invention also concerns the isolation and characterization of PepF and PepE2, other endopeptidases. Thus, the present invention is directed to compositions and methods concerning endopeptidases and their use in hydrolyzing proline-containing peptides. These uses include reducing bitterness in foods whose bitterness involves such peptides, and their use in the cheesemaking process. Moreover, these endopeptidases could be employed in other areas in which cleavage of proline-containing peptides provides a benefit. One such area is the treatment or prevention of inflammation, such as in celiac sprue.

Accordingly, compositions of the invention concern nucleic acids, proteinaceous compositions, food additives, vectors, and host cells that relate to PepO2, PepO3, PepF, PepN, and/or PepE2. In specific embodiments, it relates to PepO2 and PepO3 from LAB, particularly *Lactobacillus*, and more particularly, *Lactobacillus delbreuckii* (including subspecies *bulgaricus*), *Lactobacillus helveticus*, and *Lactobacillus casei*. In certain embodiments, compositions further comprise PepN, PepF, PepE, PepO and/or PepE2. Any embodiments discussed with respect to PepO2 may be applied with respect to PepO3, as well as to PepN, PepF, PepE, PepO and/or PepE2, and vice versa. Similarly, any embodiments discussed with respect to PepO3 may be applied with respect to PepO2, as well as PepN, PepF, PepE, PepO and/or PepE2, and vice versa.

The present invention involves isolated PepO2 polypeptides, which may be full-length, or less or more than full-length. A PepO2 polypeptide includes a polypeptide with an amino acid sequence that has, or that has at least 50, 55, 60, 65, 70, 75, 80, 85, 90, 95, or 100% homology to SEQ ID NO:2, and in some cases, has the activity of PepO2 from *L. helveticus* based on assays as described in the Examples.

A polypeptide has "homology" or is considered "homologous" to a second polypeptide if one of the following "homology criteria" is met: 1) at least 50% of the polypeptide has sequence identity at the same positions with the second polypeptide; 2) there is some sequence identity at the same positions with the second polypeptide and at the nonidentical residues, at least 50% of them are conservative differences, as described herein, with respect to the second polypeptide; or 3) at least 50% of the polypeptide has sequence identity with the second polypeptide, but with possible gaps of nonidentical residues between identical residues. If the term "homology" or "homologous" is qualified by a number, for example, "80% homology" or "80% homologous," then the homology criteria, with respect to 1), 2), and 3), is adjusted from "at least 50%" to "at least 80%." Thus it is contemplated that there may homology of at least 30%, 35%, 40%, 45%, 50%, 55%, 60%, 65%, 70%, 75%, 80%, 85%, 90%, 95%, or more between two proteinaceous molecules or portions of proteinaceous molecules. It is contemplated that a homologous polypeptide contains the functional activity of the cognate endopeptidase.

In some embodiments, an isolated PepO2 polypeptide comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, or 647 contiguous amino acids of SEQ ID NO:2, and ranges therein. It is specifically contemplated that an isolated PEPO2 polypeptide comprises the amino acid sequence of SEQ ID NO:2.

The present invention also relates to PepO3 polypeptides, which includes a polypeptide with an amino acid sequence that has, or that has at least 50, 55, 60, 65, 70, 75, 80, 85, 90, 95, or 100% homology to SEQ ID NO:4, and in some cases, has the activity of PepO3 from *Lb. helveticus* based on assays as described in the Examples. In some embodiments, an isolated PepO3 polypeptide comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, or 643 contiguous amino acids of SEQ ID NO:4, and ranges therein. It is specifically contemplated that an isolated PepO3 polypeptide comprises the amino acid sequence of SEQ ID NO:4.

The present invention also relates to PepF. In different embodiments of the invention, PepF polypeptides include a polypeptide with an amino acid sequence that has, or that has at least 50, 55, 60, 65, 70, 75, 80, 85, 90, 95, or 100% homology to SEQ ID NO:30, and in some cases, has the activity of PepF from *Lb. helveticus* based on assays as described in the Examples. In some embodiments, an isolated PepO3 polypeptide comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, or 598 contiguous amino acids of SEQ ID NO:30, and ranges therein. It is specifically contemplated that an isolated PepF polypeptide comprises the amino acid sequence of SEQ ID NO:30.

The present invention also relates to PepE2. In different embodiments of the invention, PepE2 polypeptides include a polypeptide with an amino acid sequence that has, or that has at least 50, 55, 60, 65, 70, 75, 80, 85, 90, 95, or 100% homology to SEQ ID NO:32, and in some cases, has the activity of PepE2 from *Lb. helveticus* based on assays as described in the Examples. In some embodiments, an isolated PepE2 polypeptide comprises at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, or 437 contiguous amino acids of SEQ ID NO:32, and ranges therein. It is specifically contemplated that an isolated PepE2 polypeptide comprises the amino acid sequence of SEQ ID NO:32.

In some embodiments, endopeptidases of the invention have activity with respect to one or more of SEQ ID NO:5-SEQ ID NO:32, which are peptide or polypeptide sequences.

The present invention also concerns isolated nucleic acid molecules. In certain embodiments of the invention, there are isolated PepO2 nucleic acid molecules or polynucleotides comprising a sequence encoding any of the polypeptide segments of SEQ ID NO:2 discussed above, or at least or at most of any of the recited segments. Similarly, isolated PepO3 nucleic acid molecules or polynucleotides comprise a sequence encoding any of the polypeptide segments of SEQ ID NO:4 discussed above, or at least or at most of any of the recited segments.

Nucleic acids of the invention also include, or include at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 11500, 1600, 1700, 1800, 1900, 2000, 2100, 2200, 2300, 2395, 2400, 2500, 2600, 2700, 2760 contiguous bases or nucleotides of SEQ ID NO:1, SEQ ID NO:3, SEQ ID NO:31 or SEQ ID NO:33, or any range therein. It is specifically contemplated that an isolated PepO2 nucleic acid comprises the sequence of SEQ ID NO:1. It is also contemplated that an isolated PepO3 nucleic acid comprises the sequence of SEQ ID NO:3. An isolated PepF nucleic acid comprises the sequence of SEQ ID NO:31 in some embodiments of the invention, while in others, an isolated PepE2 nucleic acid comprises the sequence of SEQ ID NO:33. It is further contemplated that PepO2 and PepO3 nucleic acid molecules have or have at least 30%, 35%, 40%, 45%, 50%, 55%, 60%, 65%, 70%, 75%, 80%, 85%, 90%, 95%, 96%, 97%, 98%, or 99% homology or identity with SEQ ID NO:1 and SEQ ID NO:3, respectively. The term "homology" discussed above can be applied in the context of nucleic acids. Alternatively, nucleic acids of the invention can also be defined by hybridization characteristics. In some embodiments, nucleic acids of the invention are able to hybridize to SEQ ID NO:1, SEQ ID NO:3, and/or SEQ ID NO:25-29. Hybridization can occur at high stringency conditions in some embodiments of the invention. Embodiments regarding Pep-encoding nucleotides such as PepO2 or PepO3 also apply to the nucleic acids encoding PepF (SEQ ID NO:31) and PepE2 (SEQ ID NO:33) polypeptides disclosed herein.

Furthermore, the present invention concerns compositions with one or more peptidases. In certain cases, a composition contains 1, 2, 3, 4, 5 or more different endopeptidases, including at least one endopeptidase with prolyl specificity. Any combination of PepO2, PepO3, PepF, PepO, PepE, PepE2, and PepN are contemplated, though compositions are not limited to only these proteins. These cocktails of endopeptidases can be used to hydrolyze one or more proline-containing peptides. Their application includes, but is not limited to, reduction of bitterness, decontamination measures, and treatment/prevention of celiac sprue. It is contemplated that such a cocktail contains isolated and active peptidase(s). "Active" means that the peptidase has the ability to hydrolyze a peptide. In certain cases, it may have a specific level or range of activities, as defined by endopeptidase units, which is described elsewhere.

The present invention also concerns vectors comprising nucleic acids of the invention, as described above and herein. These vectors can have such under the control of the promoter and/or have other components of vectors described herein. It is also contemplated that a single vector may encode for all or part of SEQ ID NO:2 and/or SEQ ID NO:4. Thus, a vector may include sequences encoding for one or more polypeptides. Vectors may include a pepO3 or a pepN promoter in embodiments of the invention.

Also included as part of the invention are host cells that have one or more exogenous nucleic acid sequences, particularly those described above and herein. In some embodiments, the cell has an exogenous nucleic acid sequence comprising all or part of a PepO2 or PepO3 nucleic acid sequence, such as SEQ ID NO:1 or SEQ ID NO:3. In further embodiments, the cell has an exogenous nucleic acid encoding all or part of a PepO2 polypeptide and/or PepO3 polypeptide, such as SEQ ID NO:2 and/or SEQ ID NO:4. It is contemplated that the host cell may be a eukaryotic or prokaryotic cell. In specific embodiments, the host cell is a prokaryotic cell, particularly a bacterial cell. The present invention may include the use of any cell used in the cheesemaking process, such as a starter culture or an adjunct culture. The invention contemplates a host cell that is a bacterial cell selected from the group consisting of *Lactococcus lactis, Streptococcus thermophilus, Lactobacillus delbreuckii, Lactobacillus helveticus* and *Lactobacillus casei*. Other host cells include yeast, fungi and other bacteria. In certain embodiments, a filamentous fungal cell is employed to produce polypeptides of the invention.

In addition to the compositions discussed above, the present invention concerns a food additive comprising all or part of a PepO2 and/or PepO3 polypeptide, or a nucleic acid encoding such polypeptides. A "food additive" refers to a composition that can be added to food or a food component for consumption by a mammal, such as a human. It is contemplated that the formulation of the food additive may be as a liquid, power, or solid. It can be used as a food additive during the food production process or to the ultimate end food product.

The PepO2, PepO3, PepF, and PepE2 polypeptides of the invention as well as PepN, PepE, and PepO polypeptides that can be used in aspects of the invention will have activity in many embodiments of the invention. Their activity can be expressed in terms of enzyme units. In certain embodiments of the invention, the activity of an endopeptidase of the invention is about, at least about, or at most about 1, 5, 10, 20, 30, 40, 50, 60, 70, 80, 90, 100, 110, 12, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 60000, 70000, 80000, 90000, 100,000 units or more, or any range derivable therein. One endopeptidase unit is defined as one nmole of substrate hydrolyzed (β-CN(f193-209)) per hour per mg of the protein at 37° C., as described, for example, in Examples 2 and 3.

The invention also concerns methods for producing cheese and for reducing bitterness in food products by cleaving peptides associated with a bitter taste. The invention takes advantage of the activity of PepO2 and/or PepO3 polypeptides in cleaving bitter peptides and thus, it is contemplated that these polypeptides, singly or together or with other endopeptidases, are provided at one or more points during the cheesemaking or other food making process.

In some embodiments, there are methods of producing cheese comprising: a) contacting a bacterial host cell of the invention with milk, whereby at least one milk product is produced; and, b) producing cheese from the milk product. Thus, in some embodiments, one or more endopeptidases are utilized in the cheesemaking process by providing the endopeptidase with the starter culture for the cheese or as some other bacterial cell used in the process. In certain embodiments, the endopeptidase is provided in an adjunct culture, which can be provided after the initial milk products are formed. The endopeptidase is provided with the starter culture or other host cell because it exogenously expresses the endopeptidase.

Alternatively, endopeptidases of the invention could be used in foodmaking and cheesemaking processes by adding all or part of the endopeptidase to one or more steps in the process. Therefore, in some embodiments, there are methods for producing cheese involving: a) fermenting a bacterial culture with milk, such that cheese curd is produced; b) contacting the culture or cheese curd with a PepO2 and/or PepO3 polypeptide; and, c) producing cheese from the product produced by fermentation. One or more endopeptidases could be added to any part of the cheesemaking process such as at the beginning, end or during the following: warming milk; pasteurizing or homogenizing milk; coagulating milk to produce curds and whey, typically through the exposure of milk to a coagulating agent such as acid or a coagulating enzyme—which is accomplished by adding a starter culture to milk; adjusting temperature of milk with starter culture; adding salt; introducing an additive to milk during curd formation, such as calcium chloride or an antimycotic agent; discarding whey; cutting or breaking curd; cooking curd; draining or dipping curd; knitting curds; salting curds; pressing curds; or, ripening or curing or aging cheese. It is further contemplated that they may be added at more than one step during the process or that they may be added to the ultimate end product. It is also contemplated that other additives to reduce bitterness can be introduced into the process. Any starter culture can be used in the context of the invention and this includes, but is not limited to, the following bacteria: *Lactococcus lactis, Streptococcus thermophilus, Lactobacillus delbreuckii, Lactobacillus helveticus* and *Lactobacillus casei*.

In further embodiments of the invention, methods include isolating a PepO2 and/or PepO3 polypeptide from a bacterial cell comprising an exogenous nucleic acid sequence encoding a PepO2 and/or PepO3 polypeptide(s). The isolated polypeptide can then be added to the cheesemaking or food-making process, or be supplied as a food additive composition. The polypeptide(s) can be introduced to the starter culture, to the curds, to the whey, or to some other component of the process. It is contemplated that at some point subsequent to the introduction of the endopeptidase polypeptide(s), the polypeptide will be under conditions that allow it to utilize or exhibit its endopeptidase activity. In some embodiments, other endopeptidases or other proteins are utilized in these processes. In certain cases, a PepN aminopeptidase is also employed, while in others PepE2, PepO, and/or PepF can be used as well.

Additional embodiments concern a formulation that alleviates or prevents celiac sprue. Compositions of the invention can be used to treat or prevent the inflammation underlying celiac sprue. Thus, methods of the invention include treating or preventing celiac sprue in a patient comprising: administering to the patient a pharmaceutically acceptable formulation comprising a PepO2 or PepO3 polypeptide, wherein the polypeptide has endopeptidase activity. It is contemplated that the patient may be diagnosed with celiac sprue, have symptoms of celiac sprue, and/or known to be at risk for celiac sprue. In some methods, the formulation comprises both PepO2 and PepO3 polypeptides. In certain embodiments, the formulation is ingested. Furthermore, it may or may not be ingested at the same time that gluten is ingested. Formulations may be taken separately from the gluten-containing foodstuff. Alternatively, it may be formulated with the foodstuff or sprinkled on the foodstuff as a powder or liquid. It will be understood that treatment includes reduction or elimination of inflammation, alleviation of symptoms, and/or inhibition of transglutaminase activity or binding.

Other applications include use of one or more endopeptidases of the invention in a composition that can be used to decontaminate surfaces, such as food preparation surfaces. Proline-containing proteinaceous compositions can lay on surfaces such that they get transferred to subjects who may exhibit an allergic reaction to them. Therefore, the present invention concerns compositions and methods for decontaminating an area to reduce or prevent an allergic response to a proline-containing protein. In some embodiments, there is a cleaning solution or other formulation comprising one or more isolated endopeptidases selected from the group comprising: PepO2, PepO3, PepF, and PepE2. One or more of the following endopeptidases can also be added: PepN, Pep 0, and PepE. The formulation may be a solution (concentrated or not) or it may be in a solid form, such as a powder.

Such cleaning solutions or formulations can be used to decontaminate a surface, container, or other area, particularly one involving food preparation or used to hold or carry food.

The invention also concerns methods of cleaning an area or surface comprising applying to the area or surface a composition comprising one or more isolated endopeptidases selected from the group comprising: PepO2, PepO3, PepF, and PepE2. In certain embodiments, the solution or formulation comprises a cocktail of endopeptidases. The solution may be sprayed onto the surface or wiped with a sponge or other cloth-like material that has the solution on it.

The invention further concerns methods of evaluating endopeptidase activity. Such methods of the invention concern an assay for endopeptidase activity under conditions that mimic the cheesemaking process, which allows for activity in this particular context to be evaluated. For example, it can be implemented to determine the debittering efficacy of one or more endopeptidases. The invention comprises methods for evaluating endopeptidase activity of an endopeptidase comprising: a) contacting a cheese serum containing a peptide substrate with the endopeptidase; b) measuring hydrolysis of the peptide substrate. It is contemplated that multiple and different peptide substrates may be included or added to the serum. Furthermore, a cheddar cheese our gouda serum is particularly contemplated for use with the method. Such a serum can be routinely prepared by one of skill in the art, including as described in Example 4 or in Morris et al, which is specifically incorporated by reference. In some embodiments, a buffer is added to the serum. The serum may be in a concentrated form such as 2×, 3×, 4×, 5×, 10×, 15×, 20×, or more. Moreover, the endopeptidase can be provided as an isolated endopeptidase or in a cell-free extract preparation. Endopeptidases include, but are not limited to, PepO2, PepO3, PepF, PepO, PepE, PepE2, and PepN, and any combination thereof.

It is specifically contemplated that any embodiments described in the Examples section are included as an embodiment of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

It is contemplated that any method or composition described herein can be implemented with respect to any other method or composition described herein.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Peptide sequences of $\alpha_{S1}$-CN(f1-9) and β-CN (f193-209) and fragments derived from hydrolysis with CFE's. The residues that are boxed are essential AA for *L. helveticus*. The shaded residues are essential AA that only occur once in the peptide and therefore must be liberated for growth of *Lb. helveticus* when the peptide is supplied as the sole source. The peptides correspond to unique values obtained for RP-HPLC fractions from mass spectrometry data. The strain column indicates from which CFE reaction(s) a given peptide was identified. The peptide profile obtained from hydrolysis of $\alpha_{S1}$-CN(f1-9) by CFE from WT is also representative of reactions with ΔpepC, ΔpepO, and ΔpepE strains. Similarly, the peptide profile obtained from hydrolysis of β-CN(f193-209) by CFE from WT is also representative of reactions with the ΔpepC, ΔpepO, ΔpepE, and ΔpepX strains. Sequences in chart are identified as follows: (f1-9) (SEQ ID NO:5); f3-9 (SEQ ID NO:6); f4-9 (SEQ ID NO:7); f5-9 (SEQ ID NO:8); f1-7 (SEQ ID NO:9); f4-7 (SEQ ID NO:10); f1-5 (SEQ ID NO:11); (f193-209) (SEQ ID NO:12); f194-209 (SEQ ID NO:13); f195-209 (SEQ ID NO:14); f197-209 (SEQ ID NO:15); f199-209 (SEQ ID NO:16); f201-209 (SEQ ID NO:17); f193-208 (SEQ ID NO:18); f193-206 (SEQ ID NO:19); f194-206 (SEQ ID NO:20); f197-206 (SEQ ID NO:21); f199-206 (SEQ ID NO:22); f193-204 (SEQ ID NO:23); f194-204 (SEQ ID NO:24).

FIG. 2A is a chromatogram from the hydrolysis of $\alpha_{s1}$*CN(f1-9) and FIG. 2B is a chromatogram from the hydrolysis of β-CN(f193-209). Hydrolysis reactions were conducted for 30 min. Major accumulated hydrolysis products are indicated.

DESCRIPTION OF ILLUSTRATIVE EMBODIMENTS

Figure 2A:
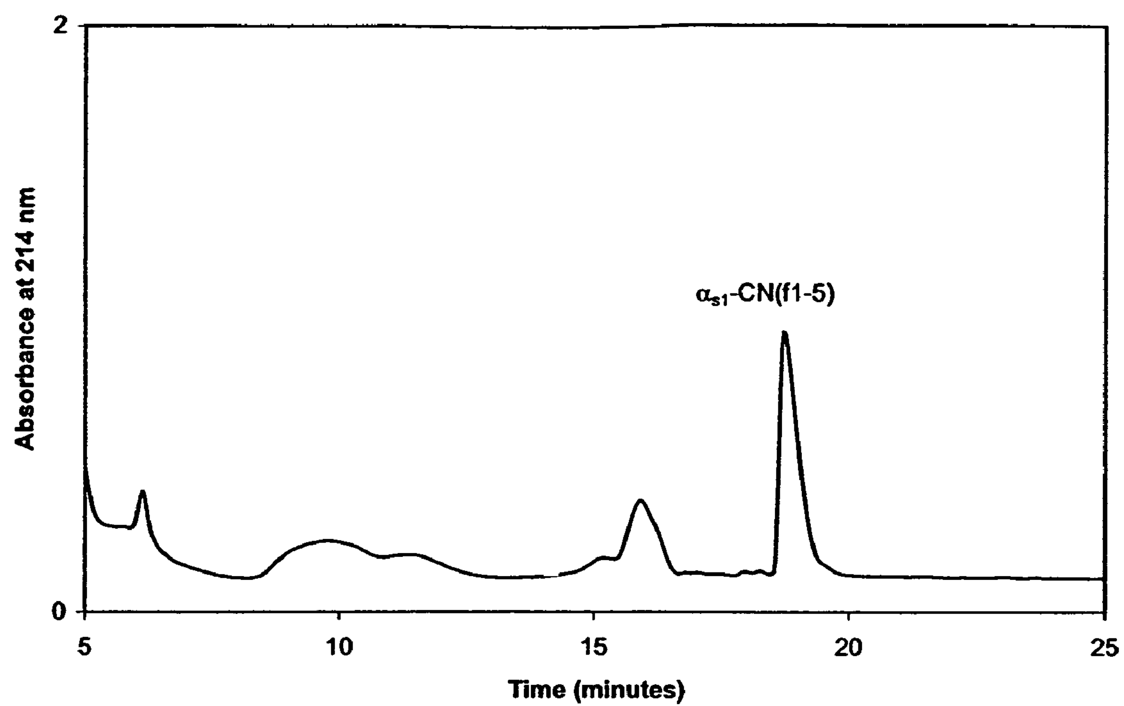
FIG. 2A-B. Chromatogram of peptides from hydrolysis of $\alpha_{s1}$-CN(f1-9) and β-CN(f193-209) by *Escherichia coli* DH5α (pSUW99).

The present invention concerns compositions and methods for producing cheese and/or reducing bitterness in food preparations in which endopeptidases are involved. More particularly, the invention concerns nucleic acids, proteinaceous compositions, food additives, expression constructs, host cells and other compositions described herein, which may be used in to reduce bitterness in a number of contexts, including cheese production.

I. Bacteria Cultures and Endopeptidases

Bitterness in cheese from the presence of bitter peptides is an ongoing and persistent problem. During the cheesemaking process, warm milk is exposed to a starter culture, which typically includes bacteria that produce lactic acid. The cultures contain a strain of bacteria capable of producing enzymes that break down proteins in milk, which provides flavor and helps the cheese ripen more quickly. In addition to the starter culture, cheesemakers sometimes add a bacteria culture to enhance cheese flavor (adjunct culture). Thus, adjunct cultures are also used in some cases.

Strains of bacteria used as starter cultures include, but are not limited to: *Lactococcus lactis, Streptococcus thermophilus, Lactobacillus delbreuckii* (including subspecies *bulgaricus*), *Lactobacillus helveticus*, and *Lactobacillus casei*. In some cases, the bacteria strain *Lactobacillus helveticus* is added to the starter culture to reduce bitterness and enhance flavor. A common adjunct culture is *Lactobacillus casei.*

These bacteria contain endopeptidases, which is an enzyme that cleaves an internal peptide bond (as opposed to a peptide bond on the end of a peptide or polypeptide) and is involved in the cheesemaking process.

In *Lactococcus lactis*, the best characterized LAB, endopeptidases that have been identified include PepO, PepO2, PepF1, and PepF2. All of these enzymes are metalloproteases and PepO, PepF1, and PepF2 are encoded in operons (Christensen et al., 1999; Kunji et al., 1996). The physiological role of these endopeptidases remains unclear; however, PepF appears to be important for protein turnover during nitrogen starvation (Nardi et al., 1999). To date, one metallo-endopeptidase, designated PepO (Chen and Steele, 1998), and a thiol-dependent endopeptidase, designated PepE (Fenster et al., 1997), have been characterized from *Lactobacillus helveticus.*

*L. helveticus* peptidases previously investigated include PepC, PepN, PepE, and PepO. They represent three different classes of enzymes. Broad specificity aminopeptidases (PepC and PepN) remove the N-terminal AA from a peptide (X↓Y-Z . . . ), with specificity dependent on the peptide length and terminal AA residues. X-prolyl dipeptidyl aminopeptidase (PepX) has specificity for removal of proline containing dipeptides (X-Pro↓Y . . . ) from the N-terminus of peptides. Endopeptidases (PepE and PepO) hydrolyze internal peptide bonds ( . . . U-V-W↓X-Y-Z . . . ) independent of the N-terminal AA residue, but potentially with specificity for one or both residues flanking the hydrolyzed peptide bond.

The endopeptidases PepO2 and PepO3 in bacteria, particularly those with comparable activity and sequence homology to PepO2 and PepO3 from *L. helveticus*, are specifically contemplated as part of the invention. The nucleic acid sequence (SEQ ID NO:1) and amino acid sequence (SEQ ID NO:2) for PepO2 in *Lactobacillus helveticus* CNRZ32 can be found at GenBank Accession number AF321529, which is specifically incorporated by reference. The nucleotide sequence of pepO3, pepF and pepE2 have been deposited in the GenBank database under accession numbers AY355128, AY365129 and AY365130, respectively, which are hereby incorporated by reference. Each of the accession number discussed in this application is specifically incorporated by reference.

A. Proteinaceous Compositions

In certain embodiments, the present invention concerns novel compositions comprising at least one proteinaceous molecule, such as an endopeptidase. In many embodiments, the proteinaceous molecule is all or part of a PepO2 or PepO3 polypeptide. Moreover, other proteinaceous molecules may be involved, for example, other enzymes that cleave peptides involved in bitterness or stabilizing enzymes or other polypeptides used in the cheesemaking process. Polypeptides used in methods of the invention may be produced by recombinant methods, or they may be naturally produced enzymes, either of which may or may not be subject to subsequent purification or isolation procedures.

As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may be at least, at most or may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 582, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater amino molecule residues, and any range derivable therein. It is specifically contemplated that such lengths of contiguous amino acids from SEQ ID NO:2 or SEQ ID NO:4 are part of the invention. Moreover, 5, 6, 7, 8, 9, 10, 11, 12, 13, 14, 15, 16, 17, 18, 19, 20 or more contiguous amino acids from proteinaceous compositions of the invention, including such lengths of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24 (collectively SEQ ID NOs:5-24), are contemplated as part of the invention.

In certain embodiments, an endopeptidase polypeptide contains at least the metallo-binding domain of the full-length polypeptide. Other regions of the enzyme can also be included.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (found on the World Wide Web at ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

1. Functional Aspects

When the present application refers to the function or activity of a endopeptidase, it is meant that the molecule in question has at least the ability to hydrolyze nonterminal peptide linkages in an oligopeptide or polypeptide. A synonym for "endopeptidase" is "endoprotease" and the term "proteinase" includes endopeptidases. Determination of which molecules possess this activity and what level of activity there is may be achieved using assays familiar to those of skill in the art, and include those described in the Examples. Christensen et al, 1995a and Christensen et al, 1995b describe methods that can readily be employed to evaluated functional changes, and these references are specifically incorporated by reference.

2. Peptide Mimetics

Another embodiment for the preparation of polypeptides according to the invention is the use of peptide mimetics. Mimetics are peptide-containing molecules that mimic elements of protein secondary structure. See e.g., Johnson (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of an endopeptidase, such as its specificity, but with altered and even improved characteristics, including, but not limited to, improved enzyme kinetics, stability, or addition of other activities or specificities.

3. Fusion Proteins

A specialized kind of insertional variant is the fusion protein, which is an example of a chimeric polypeptide. This molecule generally has all or a substantial portion of a naturally-occurring polypeptide, linked at the N- or C-terminus, to all or a portion of a second polypeptide. For example, fusions typically employ leader sequences from other species to permit the recombinant expression of a protein in a heterologous host. Another useful fusion includes the addition of a region that facilitates purification. Inclusion of a cleavage site at or near the fusion junction will facilitate removal of the extraneous polypeptide after purification. Other useful fusions include linking of functional domains.

4. Protein Purification

It may be desirable to purify endopeptidases such as PepO2 or PepO3, or variants thereof. The invention covers addition of one or more endopeptidases in contemplated methods or as a food additive composition. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

B. Nucleotides Encoding Endopeptidases

The present invention concerns polynucleotides, isolatable from cells, that are free from total genomic DNA and that are capable of expressing all or part of a protein or polypeptide or that are complementary to all or part of such a polynucleotide. The polynucleotide may encode a peptide or polypeptide containing all or part of a endopeptidase amino acid sequence or may encode a peptide or polypeptide having all or part of the amino acid sequence of other polypeptides that can be used to reduce bitterness of food products, particularly cheese. The polynucleotide may be RNA or DNA.

As used in this application, the term "endopeptidase polynucleotide" refers to a endopeptidase-encoding nucleic acid molecule that has been isolated free of total genomic nucleic acid. A "PepO2 polynucleotide" refers to a nucleic acid molecule that has been isolated free of total genomic DNA and that has the sequence of all or part of a PepO2-encoding nucleic acid sequence. Similarly, a "PepO3 polynucleotide" refers to a nucleic acid molecule that has been isolated free of total genomic DNA and that has the sequence of all or part of a PepO3-encoding nucleic acid sequence. A "PepF polynucleotide" refers to a nucleic acid molecule that has been isolated free of total genomic DNA and that has the sequence of all or part of a PepF-encoding nucleic acid sequence. A "PepE2 polynucleotide" refers to a nucleic acid molecule that has been isolated free of total genomic DNA and that has the sequence of all or part of a PepE2-encoding nucleic acid sequence.

A nucleic acid encoding all or part of a native or modified polypeptide may contain a contiguous nucleic acid sequence encoding all or a portion of such a polypeptide of the following lengths, or be at least or of at most the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2395, 2500, 3000, 3500, 4000, 4500, 5000, 5500, 6000, 6500, 7000, 7500, 8000, 9000, 10000, or more contiguous nucleotides, nucleosides, or base pairs of SEQ ID NO:1, SEQ ID NO:3, SEQ ID NO:25, SEQ ID NO:26, SEQ ID NO:27, SEQ ID NO:28, SEQ ID NO:29, SEQ ID NO:31, and/or SEQ ID NO:33, as well as any other nucleic acid used as part of the invention.

The present invention concerns nucleic acids capable of hybridizing to SEQ ID NO:1, SEQ ID NO:3, SEQ ID NOs: 25-29, SEQ ID NO:31, and/or SEQ ID NO:33. Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In particular embodiments, the invention concerns isolated nucleic acid segments and recombinant vectors incorporating nucleic acid sequences that encode a wild-type, altered, or mutant endopeptidases. Thus, an isolated nucleic acid segment or vector containing a nucleic acid segment may encode, for example, PepO2 or PepO3, which can cleave bitter peptides. The term "recombinant" may be used in conjunction with a polypeptide or the name of a specific polypeptide, and this generally refers to a polypeptide produced from a nucleic acid molecule that has been manipulated in vitro or that is the replicated product of such a molecule.

In other embodiments, the invention concerns isolated nucleic acid segments and recombinant vectors incorporating nucleic acid sequences that encode a polypeptide or peptide that includes within its amino acid sequence a contiguous amino acid sequence in accordance with, or essentially corresponding to the polypeptide.

The nucleic acid segments used in the present invention, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length polypeptide from any source or encode a truncated version of the polypeptide, for example a truncated endopeptidase polypeptide, such that the transcript of the coding region represents the truncated version. The truncated transcript may then be translated into a truncated protein. Alternatively, a nucleic acid sequence may encode a full-length polypeptide sequence with additional heterologous coding sequences, for example to allow for purification of the polypeptide, transport, secretion, post-translational modification, or for benefits such as secretion or efficacy. As discussed above, a tag or other heterologous polypeptide may be added to the modified polypeptide-encoding sequence, wherein "heterologous" refers to a polypeptide that is not the same as the modified polypeptide.

1. Vectors

Native and modified polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (2001) and Ausubel et al., 1996, both incorporated herein by reference. In addition to encoding a modified polypeptide, a vector may encode non-modified polypeptide sequences such as a tag or targetting molecule. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

There are a number of ways in which expression vectors may be introduced into cells. In certain embodiments of the invention, the expression vector comprises a virus or engineered vector derived from a viral genome. Viral vectors that are specifically contemplated for use with prokaryotic cells are bacteriophage.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

In certain embodiments, an *Lb. helveticus* promoter can be used to express peptidases of the invention. The promoter may be heterologous. In some embodiments, the promoter is a pepO3 promoter or a pepN promoter.

A promoter may be one naturally associated with a gene or sequence, as may be obtained by isolating the 5' non-coding sequences located upstream of the coding segment. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Promoters of specific use are those that may promote transcription in a lactic-acid utilizing or producing bacteria, such as those described in U.S. Pat. No. 6,140,078, which is specifically incorporated by reference.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, inducible, and/or useful under the appropriate conditions to direct high level expression of the introduced DNA segment, such as is advantageous in the large-scale production of recombinant proteins and/or peptides. The promoter may be heterologous or endogenous.

It is specifically contemplated that nucleic acid sequences of interest may be expressed in fungus and in lactococci bacteria, such as *Lc. Lactis*, a commonly used cheese starter. Thus, promoters that can direct expression in these organisms are specifically contemplated. Such promoters include the pepO3 promoter discussed herein, which can be used in lactococci.

b. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

e. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

f. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, ampicillin, GPT, zeocin and histidinol are useful selectable markers. In addition to markers conferring a phenotype that allows for the discrimination of transformants based on the implementation of conditions, other types of markers including screenable markers such as lacZ, whose basis is colorimetric analysis, are also contemplated. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid, such as a modified protein-encoding sequence, is transferred or introduced into the host cell. A transformed cell includes the primary subject cell and its progeny.

Host cells may be derived from prokaryotes or eukaryotes, including bacteria cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5$\alpha$, JM109, and KC8, as well as a number of commercially available bacterial hosts such as SURE® Competent Cells and SOLOPACK™ Gold Cells (STRATAGENE®, La Jolla, Calif.). Bacteria can also be used for large-scale production. In some embodiments, a prokaryotic cells is *Bacillus subtilis* or *Streptococcus lividans*.

Alternatively, bacterial cells such as *E. coli* LE392 could be used as host cells for phage viruses. In other embodiments, bacteria used as a starter culture or as an additive to a starter culture serve as host cells for vectors or plasmids encoding all or part of an endopeptidase, such as PEPO2 and/or PEPO3.

Cells for the commercial production of polypeptides are also contemplated. In addition to mammalian cells, yeast, fungi and bacterial cells have been used. See Benyx, 2004. Yeast include but are not limited to methylotrophic yeast such as *Pichia pastoris* and *Pichia methanolica*. Fungi can be used, particularly filamentous fungi. In certain embodiments, a fungus such as *Chrysosporium lucknowense* (C1), *Apergillus niger*, and *Trichoderma reesei* can be employed as a host cell. Also contemplated are *Penicillium roqueforti, Penicillium candidum, Geotrichum candidum, Torula kefir* and *Saccharomyces kefir*. These applications are well known to those of skill in the art and are described in the literature, for example, in the Handbook of Fungal Biotechnology (Arora et al., 2003) and Punt et al., 2002, which are specifically incorporated by reference. Moreover, thermofilic fungi can be employed: *Zygomycetes; Absidia corymbifera; Mortierella turficola; M. wolfi; Mucor miehei; M. pusillus; Rhizomucor* sp.; *Rhizopus arrhizus; R. cohnii; R. microsporus; Ascomycetes; Allescheria terrestris; Byssochlamys verrucosa; Chaetomium britannicum; C. thermophile; C. thermophile* var. *coprophile; C. thermophile* var. *dissitum; C. virginicum; Emericella nidulans; Hansenula polymorpha; Myriococcum albomyces; Sphaerospora saccata; Talaromyces byssochlamydoides; T.*

*emersonii; T. leycettanus; T. thermophilus; Thermoascus aurantiacus; T. crustaceus; Thielavia australiensis; T. sepedonium; T. thermophila; Basidiomycetes; Coprinus delicatulus; Mycelia Sterila; Burgoa-Papulaspora; Papulaspora thermophila; Deuteromycetes; Acremonium albamensis; Acrophialophora fusispora; Aspergillus candidus; A. fumigatus; Botrytis* sp. (=*Sphaerospora saccata*); *Calcarisporium thermophile; Cephalosporium* sp. (=*Allescheria terrestris*); *Cephalosporium* sp. (=*Thielavia australiensis*); *Geotrichum* sp. A; *Humicola grisea* var. *thermoidea; H. insolens; H. lanuginosa; H. stellata; Malbranchea pulchella* var. *sulfurea; Nodulisporium cylindroconium* (*Tritirachium* sp. A); *Paecilomyces crustaceus* (=*Thermoascus*); *P. puntonii; P. variotii; Paecilomyces* sp. (=*Byssochlamys verrucosa*); *Paecilomyces* sp. (=*Talaromyces byssochlamydoides*); *Penicillium duponti* (=*Talaromyces thermophilus*); *P. emersonii* (=*Talaromyces*); *P. leycettanum* (=*Talaromyces*); *P. piceum; P. argillaceum; Ptychogaster* sp. (*Sporotrichum pulverulentum*); *Scolecobasidium* sp. A (=*Diplorhinotrichum gallopavum*); *Sporotrichum thermophile* (=*Thielavia*); *S. pulverulentum; Stilbella thermophila; Thermomyces ibadanesis; Torula thermophila; Torulopsis candida; Tritirachium* sp. A (=*Nodulisporium cylindroconium*). The choice of a species, and within a species the choice of a strain or variety, which will accomplish the desired result and will produce endopeptidases at acceptable yields and having adequate thermal stability and activity, is a process of systematic testing and assay procedures. Once a satisfactory species and a satisfactory strain or variety of that species have been provided, it will provide a suitable continuing source of the organism for the production of lactase in yields and of qualities desired.

Other examples for expression of endopeptidases of the invention and the use of starter cultures can be found in U.S. Pat. Nos. 6,548,089, 6,335,040, 6,127,142, and 5,888,966, which are hereby incorporated by reference for this information, as well as embodiments regarding formulations and other cheesemaking processes.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac®2.0 from Invitrogen® and BacPack™ Baculovirus Expression System From Clontech®.

In addition to the disclosed expression systems of the invention, other examples of expression systems include Stratagene®'S Complete Control™ Inducible Mammalian Expression System, which involves a synthetic ecdysone-inducible receptor, or its pET Expression System, an *E. coli* expression system.

4. Methods of Nucleic Acid Transfer

Suitable methods for nucleic acid delivery to effect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

II. Methods of Producing Cheese

Methods of the invention involve using endopeptidases to reduce bitterness. In specific embodiments, methods concern using endopeptidases in the production of cheese, which can become bitter during the aging process.

The production of cheese involves a number of steps, which may include, but are not limited to, one or more of the following steps (whose order may be altered): warming milk; pasteurizing or homogenizing milk; coagulating milk to produce curds and whey, typically through the exposure of milk to a coagulating agent such as acid or a coagulating enzyme—which is accomplished by adding a starter culture to milk; adjusting temperature of milk with starter culture; adding salt; introducing an additive to milk during curd formation, such as calcium chloride or an antimycotic agent; discarding whey; cutting or breaking curd; cooking curd; draining or dipping curd; knitting curds; salting curds; pressing curds; and, ripening or curing or aging cheese at a particular temperature and humidity level for a particular amount of time. Moreover, in particular embodiments, methods of the invention involve traditional or well known cheese-making steps but also include steps and compositions involving endopeptidases of the invention. Steps concerning endopeptidases may involve introduction of the enzymes batchwise, e.g., in a tank with stirring, or the introduction may be continuous, e.g., a series of stirred tank reactors.

Methods of cheesemaking are well known to those of skill in the art. Such methods include those described in the following patents, which are hereby incorporated by reference: U.S. Pat. Nos. 6,572,901; 6,558,716; 6,551,635; 6,548,089; 6,485,762; 6,475,538; 6,468,570; 6,465,033; 6,458,394; 6,455,092; 6,443,379; 6,416,797; 6,413,568; 6,410,076; 6,401,604; 6,399,121; 6,335,040; 6,297,042; 6,270,823; 6,258,390; 6,242,036; 6,183,804; 6,140,078; 6,139,889; 6,120,809; 6,103,277; 6,026,740; 5,988052; 5.948,459; 5,853,786; 5,688,542; 5,643,621; 5,635,228; 5,554,398; 5,547,691; 5,505,979; 5,462,755; 5,429,829; 5,395,631; 5,356,639; 5,106,631.

Production of the following cheeses is specifically contemplated, though the invention is not limited to their production: Abbaye de Belloc, Abbaye du Mont des Cats, Abertam, Abondance, Ackawi, Acorn, Adelost, Affidelice au Chablis, Afuega'l Pitu, Airag, Airedale, Aisy Cendre, Allgauer Emmentaler, Alverca, Ambert, American Cheese, Ami du Chambertin, Anejo Enchilado, Anneau du Vic-Bilh, Anthoriro, Appenzell, Aragon, Ardi Gasna, Ardrahan, Armenian String, Aromes au Gene de Marc, Asadero, Asiago, Aubisque Pyrenees, Autun, Avaxtskyr, Baby Swiss, Babybel, Baguette Laonnaise, Bakers, Baladi, Balaton, Bandal, Banon, Barry's Bay Cheddar, Basing, Basket Cheese, Bath Cheese, Bavarian Bergkase, Baylough, Beaufort, Beauvoorde, Beenleigh Blue, Beer Cheese, Bel Paese, Bergader, Bergere Bleue, Berkswell, Beyaz Peynir, Bierkase, Bishop Kennedy, Blarney, Bleu d'Auvergne, Bleu de Gex, Bleu de Laqueuille, Bleu de Septmoncel, Bleu Des Causses, Blue, Blue Castello, Blue Rathgore, Blue Vein (Australian), Blue Vein Cheeses, Bocconcini, Bocconcini (Australian), Boeren Leidenkaas, Bonchester, Bosworth, Bougon, Boule Du Roves, Boulette d'Avesnes, Boursault, Boursin, Bouyssou, Bra, Braudostur, Breakfast Cheese, Brebis du Lavort, Brebis du Lochois, Brebis du Puyfaucon, Bresse Bleu, Brick, Brie, Brie de Meaux, Brie de Melun, Brillat-Savarin, Brin, Brin d'Amour, Brin d'Amour, Brinza (Burduf Brinza), Briquette de Brebis, Briquette du Forez, Broccio, Broccio Demi-Affine, Brousse du Rove, Bruder Basil, Brusselae Kaas (Fromage de Bruxelles), Bryndza, Buchette d'Anjou, Buffalo, Burgos, Butte, Butterkase, Button (Innes), Buxton Blue, Cabecou, Caboc, Cabrales, Cachaille, Caciocavallo, Caciotta, Caerphilly, Cairnsmore, Calenzana, Cambazola, Camembert de Normandie, Canadian Cheddar, Canestrato, Cantal, Caprice des Dieux, Capricorn, Goat, Capriole Banon, Carre de l'Est, Casciotta di Urbino, Cashel Blue, Castellano, Castelleno, Castelmagno, Castelo Branco, Castigliano, Cathelain, Celtic Promise, Cendre d'Olivet, Cerney, Chabichou, Chabichou du Poitou, Chabis de Gatine, Chaource, Charolais, Chaumes, Cheddar, Cheshire, Chevres, Chevrotin des Aravis, Chontaleno, Civray, Coeur de Camembert au Calvados, Coeur de Chevre, Colby, Cold Pack, Comte, Coolea, Cooleney, Coquetdale, Corleggy, Cornish Pepper, Cotherstone, Cotija, Cottage Cheese, Cottage Cheese (Australian), Cougar Gold, Coulommiers, Coverdale, Crayeux de Roncq, Cream Cheese, Cream Havarti, Crema Agria, Crema Mexicana, Creme Fraiche, Crescenza, Croghan, Crottin de Chavignol, Crottin du Chavignol, Crowdie, Crowley, Cuajada, Curd, Cure Nantais, Curworthy, Cwmtawe Pecorino, Cypress Grove Chevre, Danablu (Danish Blue), Danbo, Danish Fontina, Daralagjazsky, Dauphin, Delice des Fiouves, Denhany Dorset Drum, Derby, Dessertnyj Belyj, Devon Blue, Devon Garland, Dolcelatte, Doolin, Doppelrhamstufel, Dorset Blue Vinney, Double Gloucester, Double Worcester, Dreux a la Feuille, Dry Jack, Duddleswell, Dunbarra, Dunlop, Dunsyre Blue, Duroblando, Durrus, Dutch Mimolette (Commissiekaas), Edam, Edelpilz, Emental Grand Cru, Emlett, Emmental, Epoisses de Bourgogne, Esbareich, Esrom, Etorki, Evansdale Farmhouse Brie, Evora De L'Alentejo, Exmoor Blue, Explorateur, Feta, Feta (Australian), Figue, Filetta, Fin-de-Siecle, Finlandia Swiss, Finn, Fiore Sardo, Fleur du Maquis, Flor de Guia, Flower Marie, Folded, Folded cheese with mint, Fondant de Brebis, Fontainebleau, Fontal, Fontina Val D'Aosta, Fougerus, Four Herb Gouda, Fourme d'Ambert, Fourme de Haute Loire, Fourme de Montbrison, Fresh Jack, Fresh Mozzarella, Fresh Ricotta, Fresh Truffles, Fribourgeois, Friesekaas, Friesian, Friesla, Frinault, Fromage a Raclette, Fromage Corse, Fromage de Montagne de Savoie, Fromage Frais, Fruit Cream Cheese, Frying Cheese, Fynbo, Gabriel, Galette du Paludier, Galette Lyonnaise, Galloway Goat's Milk Gems, Gammelost, Gaperon a l'Ail, Garrotxa, Gastanberra, Geitost, Gippsland Blue, Gjetost, Gloucester, Golden Cross, Gorgonzola, Gornyaltajski, Gospel Green, Gouda, Goutu, Gowrie, Grabetto, Graddost, Grafton Village Cheddar, Grana, Grana Padano, Grand Vatel, Grataron d'Areches, Gratte-Paille, Graviera, Greuilh, Greve, Gris de Lille, Gruyere, Gubbeen, Guerbigny, Halloumi, Halloumy (Australian), Haloumi-Style Cheese, Harbourne Blue, Havarti, Heidi Gruyere, Hereford Hop, Herrgardsost, Herriot Farmhouse, Herve, Hipi Iti, Hubbardston Blue Cow, Hushallsost, Iberico, Idaho Goatster, Idiazabal, Il Boschetto al Tartufo, Ile d'Yeu, Isle of Mull, Jarlsberg, Jermi Tortes, Jibneh Arabieh, Jindi Brie, Jubilee Blue, Juustoleipa, Kadchgall, Kaseri, Kashta, Kefalotyri, Kenafa, Kernhem, Kervella Affine, Kikorangi, King Island Cape Wickham Brie, King River Gold, Klosterkaese, Knockalara, Kugelkase, L'Aveyronnais, L'Ecir de l'Aubrac, La Taupiniere, La Vache Qui Rit, Laguiole, Lairobell, Lajta, Lanark Blue, Lancashire, Langres, Lappi, Laruns, Lavistown, Le Brin, Le Fium Orbo, Le Lacandou, Le Roule, Leafield, Lebbene, Leerdammer, Leicester, Leyden, Limburger, Lincolnshire Poacher, Lingot Saint Bousquet d'Orb, Liptauer, Little Rydings, Livarot, Llanboidy, Llanglofan Farmhouse, Loch Arthur Farmhouse, Loddiswell Avondale, Longhorn, Lou Palou, Lou Pevre, Lyonnais, Maasdam, Macconais, Mahoe Aged Gouda, Mahon, Malvern, Mamirolle, Manchego, Manouri, Manur, Marble Cheddar, Marbled Cheeses, Maredsous, Margotin, Maribo, Maroilles, Mascares, Mascarpone, Mascarpone (Australian), Mascarpone Torta, Matocq, Maytag Blue, Meira, Menallack Farmhouse, Menonita, Meredith Blue, Mesost, Metton (Cancoillotte), Meyer Vintage Gouda, Mihalic Peynir, Milleens, Mimolette, Mine-Gabhar, Mini Baby Bells, Mixte, Molbo, Monastery Cheeses, Mondseer, Mont D'or Lyonnais, Montasio, Monterey Jack, Monterey Jack Dry, Morbier, Morbier Cru de Montagne, Mothais a la Feuille, Mozzarella, Mozzarella (Australian), Mozzarella di Bufala, Mozzarella Fresh, in water, Mozzarella Rolls, Munster, Murol, Mycella, Myzithra, Naboulsi, Nantais, Neufchatel, Neufchatel (Australian), Niolo, Nokkelost, Northumberland, Oaxaca, Olde York, Olivet au Foin, Olivet Bleu, Olivet Cendre, Orkney Extra Mature Cheddar, Orla, Oschtjepka, Ossau Fermier, Ossau-Iraty, Oszczypek, Oxford Blue, P'tit Berrichon, Palet de Babligny, Paneer, Panela, Pannerone, Pant ys Gawn, Parmesan (Parmigiano), Parmigiano Reggiano, Pas de l'Escalette, Passendale, Pasteurized Processed, Pate de Fromage, Patefine Fort, Pave d'Affinois, Pave D'Auge, Pave de Chirac, Pave du Berry, Pecorino, Pecorino in Walnut Leaves, Pecorino Romano, Peekskill Pyramid, Pelardon des Cevennes, Pelardon des Corbieres, Penamellera, Penbryn, Pencarreg, Perail de Brebis, Petit Morin, Petit Pardou, Petit-Suisse, Picodon de Chevre, Picos de Europa, Piora, Pithtviers au Foin, Plateau de Herve, Plymouth Cheese, Podhalanski, Poivre d'Ane, Polkolbin, Pont l'Eveque, Port Nicholson, Port-Salut, Postel, Pouligny-Saint-Pierre, Pourly, Prastost, Pressato, Prince-Jean, Processed Cheddar, Provolone, Provolone (Australian), Pyengana Cheddar, Pyramide, Quark, Quark (Australian), Quartirolo Lombardo, Quatre-Vents, Quercy Petit, Queso Blanco, Queso Blanco con Frutas—Pina y Mango, Queso de Murcia, Queso del Montsec, Queso del Tietar, Queso Fresco, Queso Fresco (Adobera), Queso Iberico, Queso Jalapeno, Queso Majorero, Queso Media Luna, Queso Para Frier, Queso Quesadilla, Rabacal, Raclette, Ragusano, Raschera, Reblochon, Red Leicester, Regal de la Dombes, Reggianito, Remedou, Requeson, Richelieu, Ricotta, Ricotta (Australian), Ricotta Salata, Ridder, Rigotte, Rocamadour, Rollot, Romano, Romans Part Dieu, Roncal, Roquefort, Roule, Rouleau De Beaulieu, Royalp Tilsit, Rubens, Rustinu, Saaland Pfarr, Saanenkaese, Saga, Sage Derby, Sainte Maure, Saint-Marcellin, Saint-Nectaire, Saint-Paulin, Salers, Samso, San Simon, Sancerre, Sap Sago, Sardo, Sardo Egyptian, Sbrinz, Scamorza, Schabzieger, Schloss, Selles sur Cher, Selva, Serat, Seriously Strong Cheddar, Serra da Estrela, Sharpam, Shelburne Cheddar, Shropshire Blue, Siraz, Sirene, Smoked Gouda, Somerset Brie, Sonoma Jack, Sottocenare al Tartufo, Soumaintrain, Sourire Lozerien, Spenwood, Sraffordshire Organic, St. Agur Blue Cheese, Stilton, Stinking Bishop, String, Sussex Slipcote, Sveciaost, Swaledale, Sweet Style Swiss, Swiss Syrian (Armenian String), Tala, Taleggio, Tamie, Tasmania Highland Chevre Log, Taupiniere, Teifi, Telemea, Testouri, Tete de Moine, Tetilla, Texas Goat Cheese, Tibet, Tillamook Cheddar, Tilsit, Timboon Brie, Toma, Tomme Brulee, Tomme d'Abondance, Tomme de Chevre, Tomme de Romans, Tomme de Savoie, Tomme des Chouans, Tommes, Torta del Casar, Toscanello, Touree de L'Aubier, Tourmalet, Trappe (Veritable), Trois Comes De Vendee, Tronchon, Trou du Cru, Truffe, Tupi, Turunmaa, Tymsboro, Tyn Grug, Tyning, Ubriaco, Ulloa, Vacherin-Fribourgeois, Valencay, Vasterbottenost, Venaco, Vendomois, Vieux Corse, Vignotte, Vulscombe, Waimata Farmhouse Blue, Washed Rind Cheese (Australian), Waterloo, Weichkaese, Wellington, Wensleydale, White Stilton, Whitestone Farmhouse, Wigmore, Woodside Cabecou, Xanadu, Xynotyro, Yarg Cornish, Yarra Valley Pyramid, Yorkshire Blue, Zamorano, Zanetti Grana Padano, Zanetti Parmigiano Reggiano.

III. Formulations for Food Additives

Formulations for food additives are well known to those of skill in the art. The additives of the invention may be formulated as a liquid or solid pellet, powder, spray, or tablet capsule.

The use of a proteinaceous composition in a liquid composition is well know. Compositions can include glycerol, including 5, 10, 15, 20, 25, 30, 35, 40, 45, 50, 55, 60, 65, 70, 75, 80, 85, or 90% or more glycerol (v/v). Compositions may also include stabilizers or carrier proteins, such as albumin, or preservatives.

Various other additives which are conventionally added to enzyme food supplement compositions, such as preservatives and the like, may be utilized. U.S. Pat. Nos. 5,387,422, 6,020,324 and 6,299,896 discuss food additive formulations and are specifically incorporated by reference.

The compositions disclosed herein may be delivered via oral administration to a person, and as such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The phrase "pharmacologically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

III. Formulations for Cleaning Solutions and Formulations

Formulations for cleaning compositions are well known to those of skill in the art. Such formulations may be solid or liquid, and can more specifically be a solid, pellet, powder, or spray. Examples of such formulations and other components of such compositions can be found, for example, in U.S. Pat. Nos. 6,686,324, 6,475,290, 6,066,610, 5,776,351, 5,593,598, 5,469,880, 5,234,268, 5,020,917, 4,739,906, 4,063,893, 4,017,410, and 4,001,133, which are specifically incorporated by reference.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Hydrolysis of Casein Derived Peptides by *L. Helveticus* Peptidase Deletion Mutants Indicates Presence of Previously Undetected Endopeptidase A. Growth in AA Defined Media and Defined Media with Peptide Supplements To examine effects of peptidase mutations on growth in media requiring hydrolysis of exogenous peptides, growth of *L. helveticus* and the peptidase deletion mutants (Table 1) were determined in defined media prepared with either $\alpha_{s1}$-CN(f1-9) or β-CN(f193-209) as the sole source of several essential amino acids (AA). Growth in media not requiring hydrolysis of exogenous peptides to obtain AA was determined in defined media (Christensen, 2000). The defined media is not minimal and is comprised of all free AA as the sole nitrogen source (including the non-essential Ala, Asn, Gln, Gly, Cys and Ser).

The defined media supplemented with $\alpha_{s1}$-CN(f1-9) was prepared with all the components of complete defined media except the essential AA contained within this peptide (Arg, His, Ile, Lys, and Pro) (Table 1). Likewise, the defined media supplemented with β-CN(f193-209) was prepared with all the components of complete defined media except the essential AA contained within this peptide (Arg, Ile, Leu, Phe, Pro, Tyr, and Val). Inoculations were prepared from cultures propagated in MRS at 42° C. to late exponential phase. Cells were washed and resuspended in 0.85% NaCl to the original volume, defined media was inoculated at about $10^6$ cell/ml, and cultures were incubated at 42° C. for 18 hours.

There were no discernable differences in growth for any of the strains in AA defined media or peptide supplemented media (all strains $OD_{600}$ about 2.4-2.8, final pH~3.6). The lack of growth deficiencies of single peptidase deletion mutant strains (ΔpepC, ΔpepE, ΔpepN, ΔpepO, or ΔpepX) in defined peptide media indicates that the target peptidases are not normally involved in the hydrolysis of these peptides and/or the essential AA is liberated efficiently via an alternative pathway of hydrolysis in the absence of a given peptidase.

Complete hydrolysis of the peptide substrates is not necessarily required in order for *L. helveticus* to grow in the described defined peptide media. Some of the AA essential to *L. helveticus* occur only once in $\alpha_{s1}$-CN(f1-9) (Arg & Ile) and β-CN(f193-209) (Tyr, Leu, Arg, & Phe) and therefore must be liberated for growth in the defined media (Table 2). However, there are two residues of each of the remaining essential AAs per peptide in $\alpha_{s1}$-CN(f1-9). In β-CN(f193-209), there are multiple residues per peptide for Pro (four), Val (three), and Ile (two).

TABLE 1

Bacterial Strains

| Strain | Relevant feature(s) | Source or reference |
|---|---|---|
| CNRZ32 | Wild type; auxotrophic for all AA except Ala, Asn, Cys, Gln, Gly, and Ser. | Laboratory strain |
| JLS241 | ΔpepC derivative of CNRZ32 | (Christensen, 2000) |
| JLS242 | ΔpepN derivative of CNRZ32 | (Christensen, 2000) |
| JLS243 | ΔpepX derivative of CNRZ32 | (Christensen, 2000) |
| JLS233 | ΔpepE derivative of CNRZ32 | (Fenster and Steele, 2000) |
| JLS232 | ΔpepO derivative of CNRZ32 | (Chen and Steele, 1998) |

B. Hydrolysis of Peptides by De-energized Whole Cells

With respect to the growth analysis of the CFE derived peptides, the possibility that the substrates undergo initial hydrolysis by a cell envelope proteinase (CEP) prior to transport of the resulting peptides was also investigated. De-energized whole cell suspensions were prepared and incubated with the peptides under the same conditions described for CFE reactions and the reaction supernatants were analyzed by RP-HPLC (see methods below). No evidence of extracellular hydrolysis was found from extended time reactions (120 min) of the peptides with whole cells. Although this result was not expected, it suggests that extracellular hydrolysis prior to transport is not necessary for these peptides. There is a precedent for other multiply AA auxotrophic LAB to transport even larger peptides via the oligopeptide transport system (Opp) than reported for homologues in bacteria with fewer AA auxotrophies (Payne, 1968; Perego et al., 1991). Kinetic analysis of Opp from *Lactococcus* indicates that peptides from four to at least eighteen residues can be transported with little specificity for particular AA side chains (Detmers et al., 1998). Therefore, it is a formal possibility the *L. helveticus* is capable of transporting $\alpha_{s1}$-CN(f1-9) and β-CN (f193-209) without prior hydrolysis.

C. Hydrolysis of $\alpha_{s1}$-CN(f1-9) and β-CN(f193-209) with CFE of *L. helveticus* and Peptidase Mutants The peptides $\alpha_{s1}$-CN(f1-9) and β-CN(f193-209) were synthesized and purified at the Utah State University Biotechnology Center. Cell free extracts (CFE) were prepared as described previously (Christensen, 2000). The protein concentration of the CFE and bovine serum albumin standards was determined using a bicinchoninic acid assay kit (Sigma, St. Louis, Mo.) (Smith et al., 1985).

Peptide hydrolysis reactions with *L. helveticus* CFE were performed in 50 μl total volumes. Each sample contained 45 μl of CFE or appropriate dilution to 0.95-1.05 mg/ml protein. The reactions commenced with the addition of the peptide substrate and were incubated at 37° C. Initial substrate concentrations in the reaction samples were 5.0 μg/l for $\alpha_{s1}$-CN(f1-9), β-CN(f193-209), and β-CN(f193-209-n-butyl amide). Incubation times of 40 min were determined to result in hydrolysis products of relatively even distribution and approximately 25-30% (by peak area) of the original peptide substrates remained. Reactions were stopped by addition of 200 μl of 40% (v/v) MeCN. Sample stability was determined to be >12 hr at room temperature.

Hydrolysis samples were separated and collected from RP-HPLC as described in Chen et al. (Chen et al., 2002). The mass of RP-HPLC separated peptide fractions were determined using a Perkin Elmer API 365 triple quadrupole electrospray ionization mass spectrometer (ESIMS) or a Bruker Reflex II for matrix-assisted laser desorption/ionization time-of-flight mass spectrometry (MALDI-TOF-MS). Peptides that could not be positively identified by mass alone were analyzed by ESIMS/MS to measure fragments of the parent peptide. ESIMS was performed at the Biotechnology Center and MALDI-TOF-MS was performed and the Chemistry Instrument Center, both at the University of Wisconsin—Madison.

The reactions of $\alpha_{s1}$-CN(f1-9) or β-CN(f193-209) with CFE of *L. helveticus* wild type and the peptidase deletion mutants were investigated to assess hydrolytic differences due to the absence of a given peptidase. The rate of depletion of $\alpha_{S1}$-CN(f1-9) and the accumulation of the primary hydrolysis product, $\alpha_{S1}$-CN(f1-7), was indistinguishable for all six strains. However, the remaining peaks accumulated from for hydrolysis by ΔpepN or ΔpepX strains were different from each other and different from wild type (as well as ΔpepC, ΔpepO, and ΔpepE strains; see FIG. 1).

The chromatograms for reactions of β-CN(f193-209) with CFE from wild type, ΔpepC, ΔpepO, ΔpepE, and ΔpepX strains were indistinguishable in terms of the rate of hydrolysis and the accumulation of the all detectable peptides (represented by WT in FIG. 1). However, the chromatogram peak profiles from hydrolysis with the ΔpepN strain were distinctly different. The most notable differences in the reaction with the ΔpepN strain were the decreased rate of hydrolysis of the initial substrate and the increased accumulation of peptide β-CN(f193-206).

Several other unique peptides accumulated in the absence of PepN activity. For the hydrolysis reactions of $\alpha_{S1}$-CN(f1-9), these peptides corresponded to a decreased ability to liberate Lys[3] from $\alpha_{S1}$-CN(f3-9) (FIG. 1). For the hydrolysis of β-CN(f193-209), these peptides corresponded to a decreased ability to liberate Tyr[193], Val[197], and Leu198 from derived peptides. The results for liberation of Lys and Leu residues are consistent with the reported AA specificities of PepN for AA-ρNA substrates (Christensen et al., 1999). The activities measured for liberation of Tyr and Val from dipeptide substrates is routinely reported to be relatively low (Niven et al., 1995). However, an evaluation of activity of purified lactococcal PepN for a tryptic digest of β-CN also indicated the ability of this peptidase to liberate Tyr from β-CN(f193-202) and Val from β-CN(f170-176), as well as peptides containing Glu at the N-terminus (Tan et al., 1993).

The absence of PepX activity from CFE resulted in the accumulation of $\alpha_{S1}$-CN(f1-5) and $\alpha_{S1}$-CN(f4-7), both peptides having an Xaa-Pro N-terminus (FIG. 1). This is also consistent with the known substrate specificity of PepX (Christensen, 1999).

Surprisingly, no differences were detected for hydrolysis of either of the peptides with CFE from the endopeptidase deletion mutants, JLS232 (ΔpepO) and JLS233 (ΔpepE), relative to wild type. The chromatograms for hydrolysis reactions of $\alpha_{S1}$-CN(f1-9) by all six strains were indistinguishable with respect to the rate of hydrolysis of $\alpha_{S1}$-CN(f1-9) and the accumulation of the primary product, $\alpha_{S1}$-CN(f1-7), indicating that none of the deleted peptidases is responsible for the hydrolysis of the Lys[7]-His[8] peptide bond. In addition, the fractions analyzed from hydrolysis reactions of β-CN(f193-209) by all six strains contained several peptides with Pro[204] or Pro[206] at the C-terminus (FIG. 1). The hydrolysis results indicate that PepE and PepO either 1) do not have significant specificity for $\alpha_{S1}$-CN(f1-9) or β-CN(f193-209) or derived peptides, 2) are not expressed significantly under the growth conditions used, or 3) the peptides that are substrates for these enzymes did not accumulate to a sufficient level to be detected in our investigation. Since the deletion of PepE and PepO did not affect the rate of formation of these peptides, these results indicated the hydrolysis was due to an as yet unidentified endopeptidase and/or carboxypeptidase.

D. Hydrolysis of the Carboxy-terminal Protected Peptide β-CN(f193-209-n-butyl amide)

To determine whether the carboxy-terminal hydrolysis of β-CN(f193-209) resulted from endopeptidase activity, hydrolysis products of the carboxyl protected substrate β-CN (f193-209-n-butyl amide) were identified. Synthesis and purification of β-CN(f193-209-n-butyl amide) was done at the University of Wisconsin Biotechnology Center. In order to reduce the extent of hydrolysis of peptides from aminopeptidase activity, hydrolysis reactions with β-CN(f193-209) and β-CN(f193-209-n-butyl amide) were performed with CFE prepared from JLS242 (ΔpepN). The predominant peptide formed from hydrolysis of both β-CN(f193-209) and β-CN (f193-209-n-butyl amide) was identified as β-CN(f193-206), indicating the role of an endopeptidase in formation of peptides with Pro[206] at the C-terminus.

E. Hydrolysis of Peptides at Low pH/High Ionic Strength

To evaluate hydrolysis of peptides under the pH and ionic conditions associated with ripening Cheddar cheese, reactions of *L. helveticus* wild type CFE with $\alpha_{S1}$-CN(f1-9) or β-CN(f193-209) were performed at pH 5.1 in 120 mM MES buffer/0.68 M NaCl (4% NaCl).

Hydrolysis reactions with CFE were also performed at pH 6.5 (as described above) for direct chromatographic comparison. The CFE were preincubated (5 min) in the designated buffers before substrate addition. Following addition of substrate, samples were incubated for 20, 40 and 60 min in order to evaluate hydrolysis over time. A comparative evaluation of chromatograms for each reaction condition (pH 6.5 vs. pH 5.1/0.68 M NaCl) for $\alpha_{S1}$-CN(f1-9) at a given reaction time revealed no differences in the hydrolysis of the initial substrate and accumulation of the primary hydrolysis product, $\alpha_{S1}$-CN(f1-7). In subtle contrast, the chromatograms for reactions with β-CN(f193-209) indicate a slight increase in the rate of hydrolysis of the initial substrate, but no significant difference in the subsequent hydrolysis of the primary product, β-CN(f194-209). The activity of an unidentified endopeptidase at pH 5.1 and 0.68 M NaCl indicates this enzyme may be important for initiating the hydrolysis of $\alpha_{S1}$-CN(f1-9), β-CN(f193-209), and other Pro containing peptides.

Example 2

Identification and Characterization of PepO2

A. Materials and Methods

1. Bacterial Strains, Plasmid and Media

*Lb. helveticus* CNRZ32 (Khalid and Marth, 1990) and its derivatives were grown in MRS broth (Difco Laboratories, Detroit, Mich.; DeMan et al., 1960) at 37° C. *Lc. lactis* LM0230 was propagated at 30° C. in M17-glucose broth (Difco Laboratories; Terzaghi and Sandine, 1975). *Escherichia coli* DH5α (Gibco-BRL Life Technologies Inc., Gaithersburg, Md., USA) and derivatives were grown in LB broth (Sambrook et al., 2001) at 37° C. with aeration. Agar plates were prepared by adding 1.5% (wt/vol) granulated agar (Difco Laboratories) to liquid media. Erythromycin (Sigma Chemical Co., St. Louis, Mo) at 500 μg/ml was added to liquid media or agar plates to select for pJDC9 (Chen and Morrison, 1988) in *E. coli.*

2. Screening of *Lb. helveticus* CNRZ32 Genomic Library

A previously constructed genomic library of *Lb. helveticus* CNRZ32 in *E. coli* DH5α (Nowakowski et al., 1993) was screened for endopeptidase activity using an amino-terminal blocked chromogenic substrate, N-acetyl-β-CN(f203-209)-ρ-nitroanilide (NA) (SynPep Co., Dublin, Calif.); this substrate is based on the C-terminal amino acid sequence of *Bos taurus* β-CN. Pooled cultures (10 isolates/pool) were grown overnight in LB broth containing erythromycin. Cells were pelleted at 13,000×g for 1 min at room temperature, washed and suspended in 10 mM Bis-Tris, pH 6.5 (Sigma). Cell-free extracts (CFEs) from *E. coli* were obtained by vortexing the samples with glass beads, alternating with cooling on ice, 1 minute each, repeated 2 times, and cell debris was removed by centrifugation for 1 min at 13,000×g. CFEs obtained from mid-log cultures of *Lb. helveticus* CNRZ32 and *E. coli* DH5α (pJDC9) were used as positive and negative controls, respectively. The presence or absence of endopeptidase activity was determined by adding 100 μl of CFE to 395 μl of 10 mM Bis-Tris (pH 6.5) containing 1 mM N-acetyl-β-CN(f203-209)-ρNA. The appearance of an intense yellow color (resulting from release of ρNA) within 15 min was a positive indication of endopeptidase activity. In the coupled-reaction, 20 μl of CFE of *E. coli* DH5α containing aminopeptidase N activity (pJDC9::pepN) was used. All assays were conducted in duplicate.

3. Plasmid Isolation and Cloning

Plasmid isolation from *E. coli* was performed as described by Sambrook et al. (2001). Restriction enzymes and T4 DNA ligase were purchased from Gibco-BRL and used as recommended by the manufacturer. Electroporation of *E. coli* was performed using a Gene Pulser (Bio-Rad Laboratories, Richmond, Calif.) as recommended by the manufacturer.

4. DNA Sequencing and Sequence Analysis

All primers were synthesized by GIBCO-BRL Custom Primers (Grand Island, N.Y.). Polymerase chain reaction (PCR) and DNA sequencing reactions were performed in a Perkin-Elmer model 480 thermal cycler (The Perkin-Elmer Corp., Norwalk, Conn.). DNA sequencing reactions were conducted using the Prism™ Ready Reaction DyeDeoxy™ Terminator Cycle Sequencing Kit (Applied Biosystems, Inc., Foster City, Calif.). DNA templates were purified with a Qiagen Inc. (Hilden, Germany) PCR purification kit. Sequencing was initially performed with M13/M13R primers (GIBCO-BRL). As the known sequenced progressed, new primers were designed accordingly. Additional primers were designed using the Affinity program supplied by Ransom Hill Bioscience, Inc. (Ramona, Calif.). DNA sequence determination was conducted by the Nucleic Acid and Protein Facility of the University of Wisconsin-Madison Biotechnology Center, using an ABI model 370/3 automated sequencer. Sequences were analyzed using the GCG sequence analysis package (Genetics Computer Group, Inc., Madison, Wis.). Protein homology searches were performed using the BLAST network service (Altschul et al., 1990). All reported DNA sequence data was confirmed by sequencing both DNA strands from at least two independent PCR products.

5. mRNA Analysis

Transcription of the PepO2 gene was investigated utilizing an 810-bp internal PepO2 fragment (nucleotide 607 to 1416) amplified and the PCR product and labeled with digoxigenin (Genius™ system, Boehringer Mannheim GmbH, Mannheim, Germany) for Northern hybridization. The primers used for probe amplification were YC-2290 (5'GATGCGATTGCACTCG) (SEQ ID NO:25) and YC-2000 (5'GATAGCGGCAGGGAAG) (SEQ ID NO:26). Total RNA was isolated using the RNeasy™ kit (Qiagen). RNA molecular weight markers, solutions and reagents used in Northern hybridization and chemiluminescent detection were purchased from Boehringer Mannheim. Northern hybridizations were performed following the procedure supplied by the manufacturer. Mapping of the 5' end of the PepO2 transcript was accomplished using 5' end rapid amplification of cDNA (5'RACE) kit (version 2.0; GIBCO-BRL). The gene specific primers used for 5'RACE were YC-2340 (5'GTTTTCGGTTTGCTTTTG) (SEQ ID NO:27), YC-2600 (5'CGGCATCTCTTTTGGC) (SEQ ID NO:28), and YC-2840 (5'GGACGATCGGCAGGG) (SEQ ID NO:29). First-strand cDNA synthesis was performed with primer YC-2340. Nested amplification of first-strand cDNA was carried out with primer YC-2600 and the anchor primer supplied with the 5'RACE kit. Sequencing reactions were conducted with primer YC-2840 using the nested amplification product as the template.

6. Synthesis of Peptide Substrates

The peptides $\alpha_{S1}$-CN(f1-9) and β-CN(f193-209) were synthesized at the Utah State University Biotechnology Center. The synthesized peptides were subsequently purified by collection of appropriate fractions from preparatory RP-HPLC. The peptides were analyzed by mass spectrometry (MS) and confirmed by Edman degradation in an Applied Biosystems Model 477B protein sequencer (Foster City, Calif.). The peptides were lyophilized and stored at −80° C. Stock solutions were prepared in sterile $ddH_2O$ and also stored at −80° C.

7. Peptide Hydrolysis Reactions

Peptide hydrolysis reactions were performed essentially as described in Example 1. A 10 μl aliquot of CFE (0.95-1.05 mg/ml protein) was diluted in a total reaction volume of 500 μl of 0.1 M Bis-Tris buffer (pH 6.5). The reactions were initiated by the addition of the substrate and were incubated at 37° C. for a minimum of 30 minutes. Initial substrate concentrations in the reaction samples were 0.2 μg/μl for both β-CN (f193-209) and $\alpha_{s1}$-CN(f1-9). Reactions were stopped by immediately freezing at −20° C.

8. Peptide Separation and Identification

Samples were injected onto a 20 μl loop using a Gilson Model 231 sample injector equipped with a Model 401 dilutor module containing a 1:1 $ddH_2O$:MeCN wash (Gilson Medical Electronics, France). The peptides were separated using a 250×2 mm Phenomenex Columbus C18 column (5μ, 100 Å) (Torrance, Calif.) preceded by a Brownlee RP-18 precolumn. The mobile phase flow rate and gradient was controlled with a Hitachi L-6200A pump (Hitachi Instruments, San Jose, Calif.). Mobile phases were continuously degassed by a slow helium sparge. Peptides were detected with a Hitachi L-4500A diode-array detector in low absorbance mode. Data was collected using the Hitachi Chromatography Data Station Software with a wavelength range of 200-300 nm with a 4 nm spectral bandwidth and 3200 msec spectral interval.

Mobile phase A (MP-A) consisted of $ddH_2O$:MeCN (99:1) with 0.1% TFA and mobile phase B (MP-B) was $ddH_2O$: MeCN (20:80) with 0.05% TFA. The separation and elution of $\alpha_{S1}$-CN(f1-9) hydrolysis samples was accomplished with the following gradient: 1-16% MP-B over 0-20 min at 0.25 ml/min, 90% MP-B at 20-22 min at 0.25 ml/min, 90%-1% over 22-25 min at 0.25 ml/min. The separation and elution of β-CN(f193-209) hydrolysis samples was accomplished with the following gradient with respect to MP-B: 4-60% over 0-40 min at 0.25 ml/min, 60-98% over 40-41 min at 0.25 ml/min, 98% from 41-45 min at 0.25-0.50 ml/min, 98%-4% over 45-47 min at 0.50-0.25 ml/min. The pump back pressure was ~1400 psi at $T_0$ and remained below 1600 psi for the duration of the gradients. Samples being separated for fraction collection were monitored in real time. Fractions were collected manually taking into account a predetermined time for the peptide to travel from the detector flow cell to the capture point.

The mass of RP-HPLC separated peptide fractions were determined using a triple quadrupole mass spectrometer (Micromass Quattro II) with an electrospray ionization sources at the Utah State University Biotechnology Center. To identify the hydrolysis products, the masses were compared to calculated molecular weight of peptides and/or amino acids derived from β-CN(f193-209) and $\alpha_{s1}$-CN(f1-9).

9. Nucleotide Sequence Accession Number

The sequence for PepO2 has been submitted to GenBank and assigned accession no. AF321529 (SEQ ID NOs:1 and 2).

B. Results

1. Screening of the Genomic Library

Prior to screening the *Lb. helveticus* genomic library, a number of preliminary tests were conducted. CFEs of *Lb. helveticus* CNRZ32 and *E. coli* DH5α were examined for endopeptidase activities capable of hydrolyzing Ac-β-CN (f203-209)-ρNA. CFE from *Lb. helveticus* CNRZ32 wild-type resulted in an intense yellow color (Abs410>0.30) within 15 min, while *E. coli* DH5α CFEs resulted in only a very light yellow color (Abs410<0.025) after 10 h. To determine if any of the previously identified *Lb. helveticus* proteolytic enzymes were required for hydrolysis of β-CN(f203-209), CFEs prepared from several peptidase mutants were examined for their ability to hydrolyze Ac-β-CN(f203-209)-ρNA (Table 2). Aminopeptidase N (PepN) was found to be required for the release of ρNA from Ac-β-CN(f203-209)-ρNA. However, no hydrolysis of Ac-β-CN(f203-209)-ρNA was observed by CFEs prepared from *E. coli* DH5α expressing *Lb. helveticus* PepN (JLS242; Christensen 2000).

Together, these results indicate that PepN is required, but not sufficient, for ρNA release from Ac-β-CN(f203-209)-ρNA. Therefore, the genomic library screen was performed using a coupled enzyme reaction with PepN.

A genomic library of *Lb. helveticus* CNRZ32 in *E. coli* DH5α was screened for endopeptidase activities with Ac-β-CN(f203-209)-ρNA. Two isolates of the 1880 isolates screened had activity in a coupled reaction with PepN. Restriction endonuclease profiles of the two isolates were visually indistinguishable. One plasmid, designated pSUW99, was selected for further analysis.

TABLE 2

Ability of *Lactobacillus helveticus* CNRZ32 and its peptidase-deficient derivatives to hydrolyze N-acetyl-β-casein(f203-209)-ρ-nitroanilide

| Strains | Relevant features | Activity[a] | Reference |
|---|---|---|---|
| CNRZ32 | Wild type | + | Khalid et al., 1990 |
| JLS232 | pepO⁻ derivative of CNRZ32 | + | Chen et al., 1998 |
| JLS233 | pepE⁻ derivative of CNRZ32 | + | unpublished |
| JLS251 | prtH⁻ derivative of CNRZ32 | + | Pederson et al., 1999 |
| JLS242 | pepN⁻ derivative of CNRZ32 | − | Example 1 |
| JLS241 | pepC⁻ derivative of CNRZ32 | + | Example 1 |
| JLS243 | pepX⁻ derivative of CNRZ32 | + | Example 1 |

[a]Enzyme activity was determined with 1.0 mM of substrate at 37° C. for 30 min. A reaction was considered positive (+) if an absorbance of more than 0.025 at 410 nm was observed.

2. Sequencing of the Endopeptidase Clone

Restriction mapping of pSUW99 revealed a 6.0-kb insert. Two 3.0-kb SstI fragments and two PstI fragments of 2.0-kb and 4.0-kb were obtained when digested with restriction endonucleases SstI and PstI, respectively. Subclones containing individual SstI fragments or PstI fragments in pJDC9 were examined for endopeptidase activity with Ac-β-CN (f203-209)-ρNA. Activity was only detected in strains containing one of the 3.0-kb SstI fragments, suggesting that the gene was present on this SstI fragment and contained a PstI site.

The complete nucleotide sequence of the 3.0-kb SstI fragment encoding endopeptidase activity was determined (SEQ ID NO:1), and an open reading frame (ORF) of 1947-bp identified (SEQ ID NO:2). This ORF could encode a polypeptide of 649 amino acids with deduced mass of 71.4 kDa. Protein sequence homology searches using current BLAST databases revealed high amino acid sequence similarity between the deduced amino acid sequence and other LAB PepO-type endopeptidases (Chavagnat et al., 2000; Froeliger et al., 1999; Hellendoorn et al., 1999; Mierau et al., 1993; Tynkkynen et al., 1993). This protein has 56% identity and 72% similarity to *Lb. helveticus* CNRZ32 endopeptidase PepO (Chen and Steele, 1998); therefore, this gene was designated PepO2. The *Lb. helveticus* PepO2 has 42% identity and 59% similarity to *Lc. Lactis*PepO (Mierau et al., 1993; Tynkkynen et al., 1993), 41% identity and 61% similarity to *Lc. lactis* PepO2 (Hellendoom et al., 1999), 38% identity and 57% similarity to the *Streptococcus therinophilus* PepO (Chavagnat et al., 2000), and 36% identity and 53% similarity to the *Lb. rhamnosus* PepO (Christensson et al., 2002). Significant similarity to mammalian metallopeptidases, including endothelin-converting enzyme (45% similarity) and enkephalinase (neutral endopeptidase, NEP; 43% similarity) was also observed. The sequence motif His-Glu -Xxx-Xxx-His (SEQ ID NO:34), characteristic of many zinc-dependent metalloproteases was also identified in PepO2 between residues 497 and 501 (HEISH (SEQ ID NO:35)). The start codon of the ORF is preceded by a putative ribosome binding site (AAGGAG; nucleotides −8 to −13) and putative promoter −10 (TATGAT; nucleotides −32 to −37) and −35 (TTTTCA; nucleotides −56 to −61) sequences (Shine and Dalgarno, 1974). An inverted repeat (nucleotides 1967 to 1979 and 2000 to 2012) was observed in the 3' noncoding region and may function as rho-independent transcriptional terminator with a ΔG [25°C.]=−21 kcal (Tinoco et al., 1973). No signal sequence was detected using a hydrophilicity plot constructed as described by Kyte and Doolittle (1982).

3. mRNA Analysis

Northern hybridization using total RNA from an exponential culture of *Lb. helveticus* CNRZ32 resulted in the detection of a transcript with a size of 2.1-kb (data not shown). This size corresponds to the size of the PepO2 ORF, and indicates that PepO2 is monocistronic. The transcriptional start site for PepO2 promoter was mapped 26-bp upstream of the PepO2 start codon by 5' RACE.

4. Substrate Specificity of PepO2

To determine if PepO2 substrate specificity is similar to that of previously described endopeptidases from *Lb. helveticus* CNRZ32, the ability of CFE from *E. coli* DH5α expressing PepO2 to hydrolyze N-benzoyl-Phe-Val-Arg-ρNA, N-benzoyl-Pro-Phe-Arg-ρNA and N-benzoyl-Val-Gly-Arg-ρNA was examined. These substrates had been utilized previously to identify and differentiate PepO and PepE in a genomic library of *Lb. helveticus* constructed in *E. coli* DH5α (Chen and Steele, 1998; Fenster et al., 1997). Derivatives of *E. coli* DH5α expressing PepO hydrolyzed N-benzoyl-Pro-Phe-Arg-ρNA and N-benzoyl-Val-Gly-Arg-ρNA, while derivatives of *E. coli* DH5α expressing PepE hydrolyzed N-benzoyl-Phe-Val-Arg-ρNA and N-benzoyl-Pro-Phe-Arg-ρNA. Hydrolysis of these substrates by PepO2, with or without PepN, was not observed. Additionally, hydrolysis of Ac-β-CN(f203-209)-ρNA by CFEs of *E. coli* DH5α Expressing *Lb. helveticus* PepO or PepE in coupled assays with PepN was not observed. These results indicated that PepO2 substrate specificity is distinct from PepO and PepE. CFE from *E. coli* DH5α expressing *Lb. helveticus* PepC or PepX were also examined in a coupled reaction with PepO2 (in place of PepN); the results indicated that only the combined activity of PepN and PepO2 was capable of releasing ρNA from Ac-β-CN(f 203-209)-ρNA.

Figure 2B:
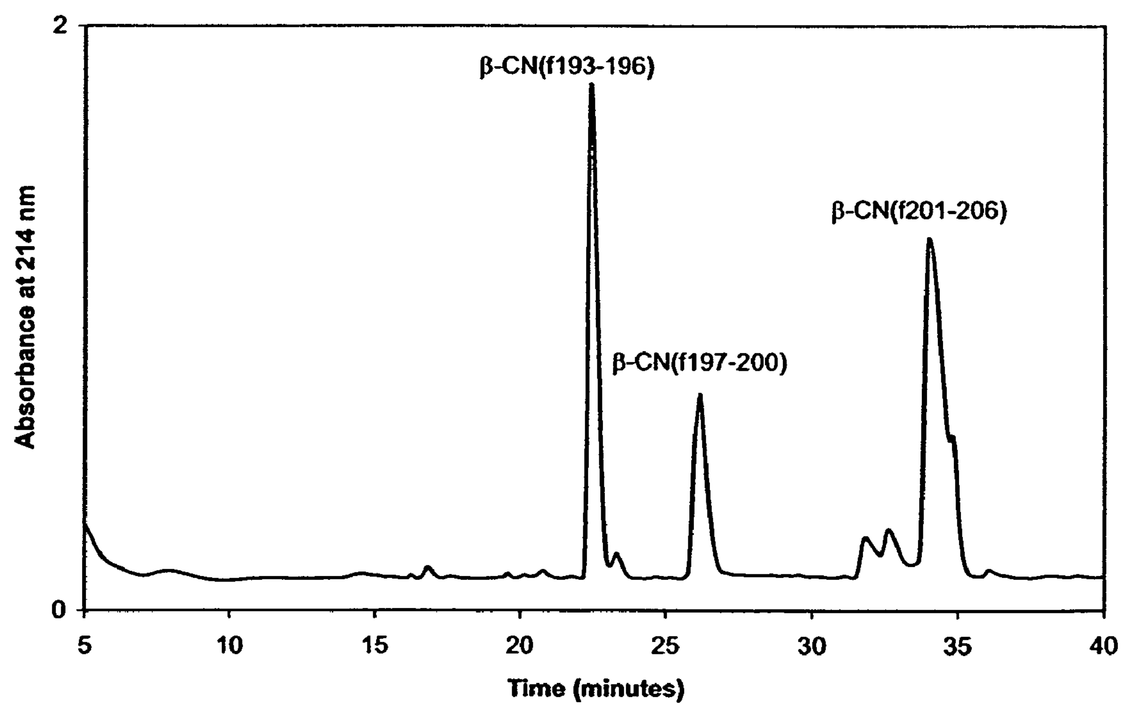
Figure 3:
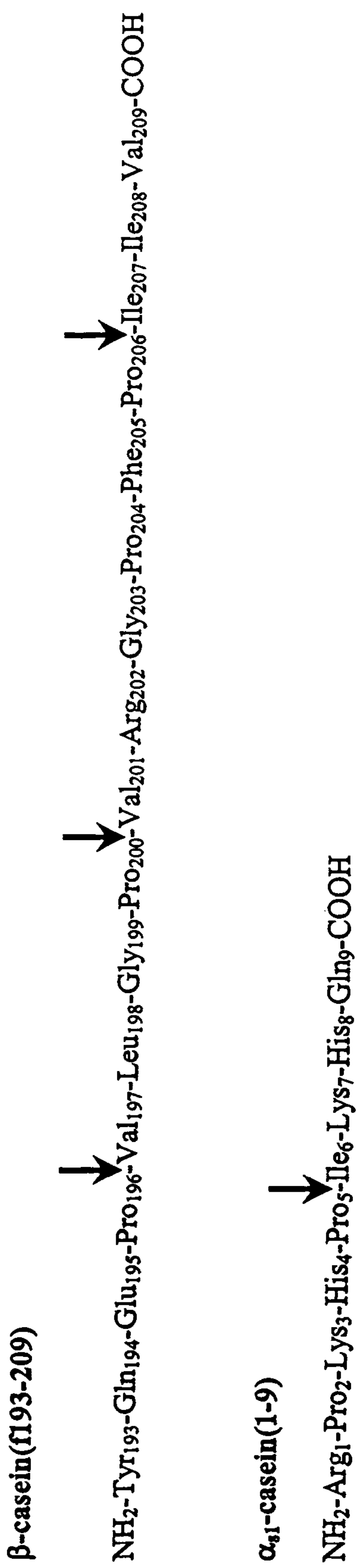
FIG. 3. Specificity of PepO2 towards substrates $\alpha_{s1}$-CN (f1-9) and β-CN(f193-209). Converging arrows represent the bonds that were hydrolyzed by cell-free extracts of *Escherichia coli* DH5α (pSUW99), expressing PepO2 from *Lactobacillus helveticus*, as determined by mass spectrometry and calculated molecular mass of peptides derived from both substrates.

To examine hydrolysis of the model casein-derived bitter peptides, β-CN(f193-209) and $\alpha_{s1}$-CN(f1-9) by PepO2, RP-HPLC was performed to separate and collect peptide hydrolysis products. No significant hydrolysis of either substrate was detected with CFEs from *E. coli* DH5α (pJDC9). However, significant hydrolysis of both β-CN(f193-209) and $\alpha_{s1}$-CN(f1-9) was detected with CFEs from *E. coli* DH5α (pSUW99) (FIG. 2). The predominant peptide fractions were collected and analyzed. PepO2 was determined to hydrolyze β-CN(f193-209) at bonds $Pro_{196}$-$Val_{197}$, $Pro_{200}$-$Val_{201}$, and $Pro_{206}$-$Ile_{207}$. Hydrolysis of $\alpha_{s1}$-CN(f1-9) was observed at $Pro_5$-$Ile_6$ bond (FIG. 3).

Example 3:

Identification and Characterization of PepO3

A draft-quality genome sequence for *L. helveticus* CNRZ32 was obtained and screened for genes encoding additional proteolytic enzymes. As is shown in Table 3, that effort revealed the CNRZ32 genome includes 8 ORFs encoding 3 known and 5 putative endopeptidases. The diversity of endopeptidases in CNRZ32 is of considerable interest because these enzymes play a key role in the hydrolysis of bitter peptides in bacterial-ripened cheeses, and high debittering activity is a known attribute of this strain (Bartels et al., 1987). For this reason, endopeptidases were selected as the first targets for our functional genomics studies in CNRZ32. Since glycopeptides are not known to make any contribution to bitter flavor defect in cheese, efforts were directed toward the other 3 novel CNRZ32 endopeptidase genes: pepE2, pepF, and PepO3.

*Lactobacillus helveticus* CNRZ32 pepE2, pepF, and PepO3 genes were isolated by PCR using primers designed from the genome sequence with added Bam HI and Kpn I linkers. The amplicons were purified, cut with each restriction endonuclease, then ligated into Bam HI and Kpn I double-digested pJDC9 (Chen and Morrison, 1988) and transformed into *Escherichia coli* DH5a. Assays for endopeptidase activity in transformants. Cell-free extract (CFE) from *E. coli* transformants containing CNRZ32 pepE2, pepF, and PepO3 genes was prepared and assayed for endopeptidase activity against chromogenic substrates in coupled assays with *L. helveticus* CNRZ32 PepN essentially as described by Chen et al. (2003). *E. coli* transformants containing CNRZ32 PepO2 (see Example 2) were included as a positive control. Hydrolysis of bitter peptides. *E. coli* CFE were incubated with the bitter peptides b-CN (f193-209) (1 mg/mL) or aS1-CN (1-9) (10 mg/mL) under simulated cheese conditions (pH 5.0-5.2, 4% NaCl, 10° C.) as described in Examples 1 and 2. Once again, *E. coli* transformants containing CNRZ32 PepO2 (see Example 2) were included as a positive control. Reactions were stopped by addition of equal volume of 10% TFA, then the remaining substrate concentration was determined by RP-HPLC. Enzyme activity was expressed as a function of the change in substrate concentration over time. Finally, peptide products from β-CN (f193-209) or a 1-CN (1-9) hydrolysis were isolated by RP-HPLC and identified by mass spectrometry at the University of Wisconsin Biotechnology Center as described above.

Three putative genes in the CNRZ32 draft genomic sequence were studied. PepO3, pepF and pepE2 appeared to encode novel endopeptidases and thus might contribute to debittering activity of this strain. BLAST searches with deduced products from these genes revealed strong amino acid identity to known endopeptidases from CNRZ32 and other LAB (Table 4). As shown in Table 4, PepO3 and PepF activities were detected in *E. coli* transformants, but no activity was recorded in CFE from the culture transformed with pepE2. CFEs from transformed *E. coli* were also tested for the ability to hydrolyze, under simulated cheese ripening conditions (pH 5.0-5.2, 4% NaCl, 10° C.), the known bitter peptides β-CN (f193-209) and αS1-CN (f1-9).

Figure 4A:
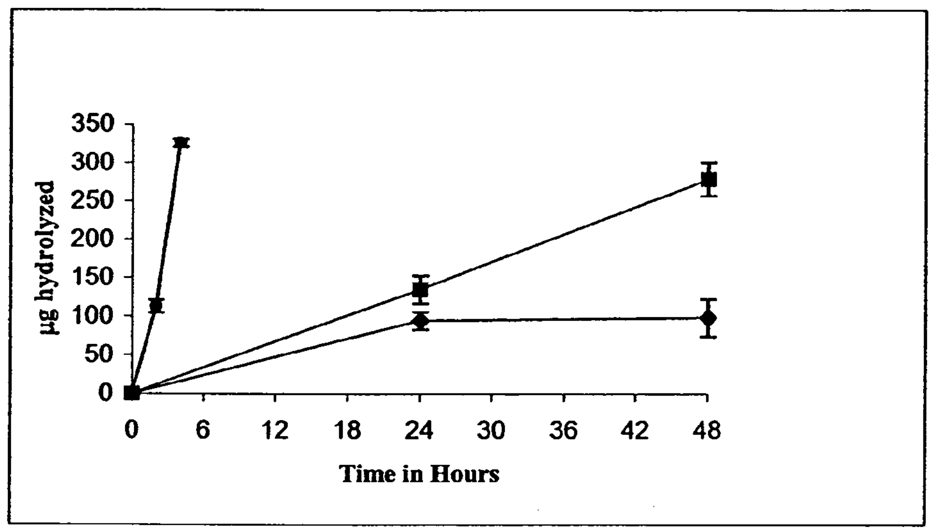
FIG. 4A-B. Rate of $\alpha_{s1}$-CN [f1-9] (FIG. 4A) or β-CN [f193-209] (FIG. 4B) hydrolysis under cheese ripening conditions by CFE from *E. coli* transformants expressing *L. helveticus* CNRZ32 endopeptidases PepO2 (circles), PepO3 (squares), and PepF (triangles). Diamonds show the level of background endopeptidase activity in CFE from untransformed *E. coli* DH5α controls.
Figure 4B:
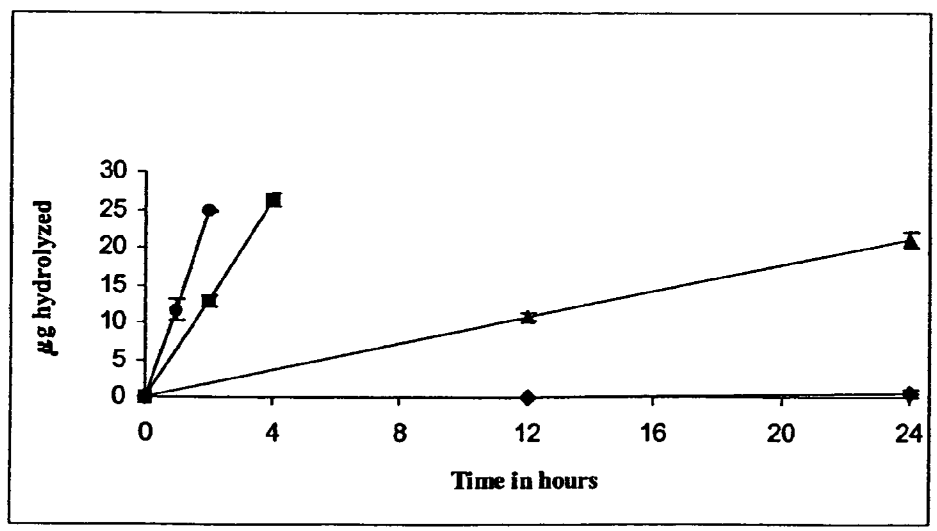
Figure 5:
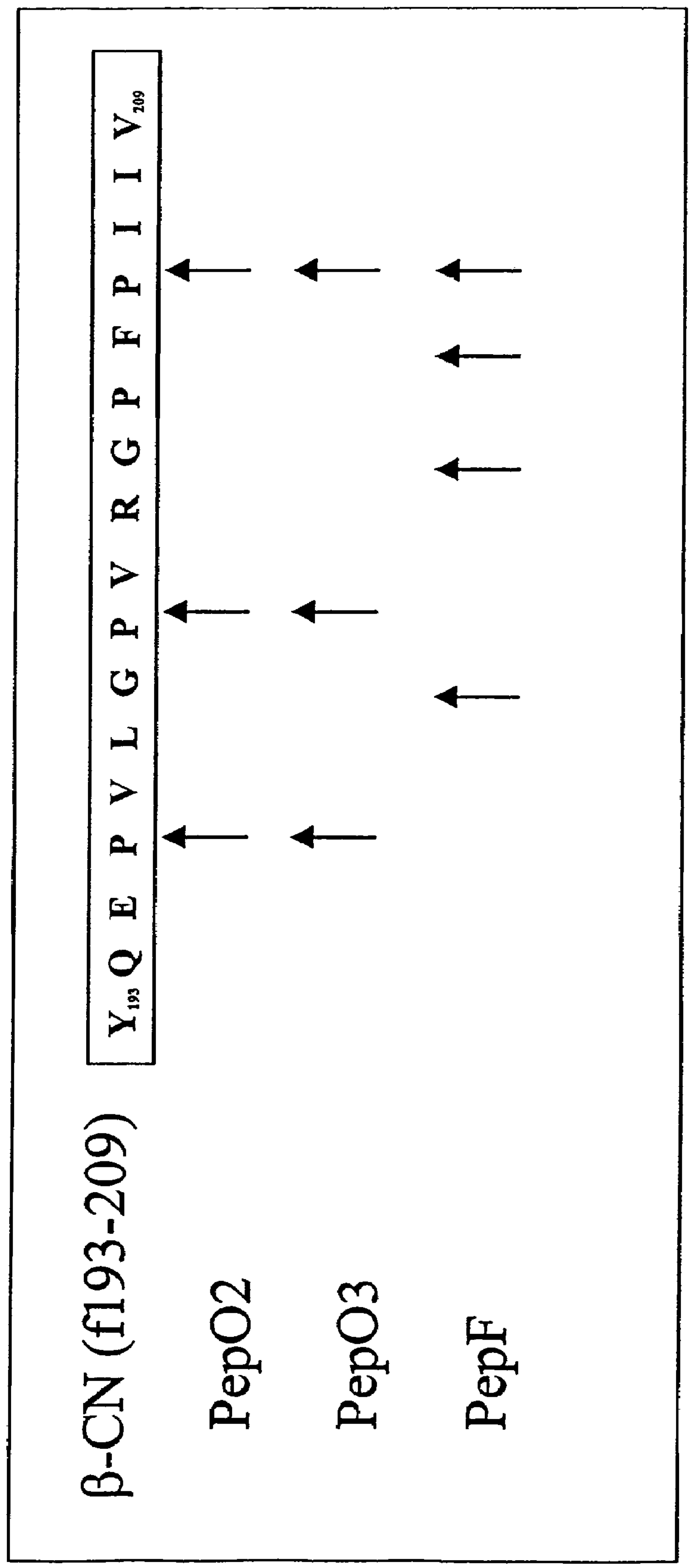
FIG. 5. Specificity of *Lb. helveticus* CNRZ32 endopeptidases toward β-CN(f193-209) (SEQ ID NO:12) under simulated cheese ripening conditions (pH 5.0-5.2, 4% NaCl, 10° C.).

As shown in FIG. 4, PepO3 and PepF each cleaved β-CN (f193-209), and PepO3 also hydrolyzed αS1-CN (f1-9). However, specific activity determinations showed both enzymes had significantly lower activity toward these peptides than PepO2 (Table 5). No hydrolysis of either peptide was detected after incubation with CFE from *E. coli* transformed with pepE2. Identification of peptide products in reaction mixtures by RP-HPLC and mass spectrometry showed PepO3 was a post-proline endopeptidase that hydrolyzed bonds Pro(206)-Ile(207), Pro(196)-Val(197), and Pro(200)-Val(201) in β-CN (f193-209) (FIG. 5). As shown in FIG. 5, PepF also displayed post-proline specificity at Pro(204)-Phe (205) and Pro(206)-Ile(207), but this enzyme also hydrolyzed β-CN (f193-209) at the X-Gly bonds Lys(198)-Gly(199) and Arg(202)-Gly(203). Specificity of PepO3 toward αS1-CN (f1-9) appears to be limited to hydrolysis of the Pro(5)-Ile(6) bond.

*L. helveticus* CNRZ32 endopeptidase PepO3 is a functional paralog to the post-prolyl endopeptidase PepO2. This enzyme displays a specificity toward the known bitter peptides β-CN (f193-209) and αS1-CN (f1-9) that is indistinguishable from that seen with PepO2. While the CNRZ32 endopeptidase PepF also displayed post-prolyl specificity, this enzyme was also able to hydrolyze X-Gly bonds β-CN (f193-209), where X=hydrophilic, charged residues.

TABLE 3

*Lactobacillus helveticus* CNRZ32 genes encoding known or putative endopeptidases

| Gene | Contig. | Known (Reference) or Predicted Product |
|---|---|---|
| pepE | 003-B | Thiol-dependent endopeptidase (Fenster et al., 1997). |
| pepE2 | 048 | PepE paralog; 53% identical to CNRZ32 endopeptidase PepE. |
| pepF | 104-A | PepF ortholog; 53% identical to *Lactococcus lactis* endopeptidase PepF |
| pepO | 026-C | Endopeptidase O ortholog (Chen and Steele, 1998). |
| PepO2 | 007-A | Post-prolyl endopeptidase (Chen et al., 2003). |
| PepO3 | 077-A | PepO/PepO2 paralog; 62% identical to CNRZ32 endopeptidases PepO and PepO2 |
| gcp | 002-B | Gcp ortholog; 63% identical to predicted O-sialoglycoprotein |
| ydiC | 002-B | glycoprotein endopeptidase ortholog; 37% identical to predicted glycoprotein endopeptidase from *Lactobacillus plantarum* |

TABLE 4

Substrate specificities of *Lactobacillus helveticus* CNRZ32 endopeptidases cloned in *Escherichia coli* DH5a

| Substrate | PepO2 | PepO3 | PepF |
|---|---|---|---|
| N-Benzoyl Pro-Phe-Arg-ρNA (w/o PepN) | − | − | + |
| N-Benzoyl Pro-Phe-Arg-ρNA | + | + | + |
| N-Benzoyl Phe-Val-Arg-ρNA | + | + | + |
| N-Succinyl Ala-Ala-Pro-Phe-ρNA | + | + | + |
| N-Succinyl Ala-Ala-Ala-Val-Ala-ρNA | + | + | + |

[a]Coupled assays using *E. coli* CFE from transformants expressing *Lb. helveticus* CNRZ32 aminopeptidase PepN; + = OD410 > 0.030 within 15 min at 37° C. in HEPES (pH 7.0).

TABLE 5

Specific activity of *Lactobacillus helveticus* CNRZ32 endopeptidases toward β-CN (f193-209) and $\alpha_{S1}$-CN (f1-9)[1]

| | Substrate | |
|---|---|---|
| Enzyme | β-CN (f193-209) | $\alpha_{S1}$-CN (f1-9) |
| PepO2 | 2.9 × 102 (11) | 1.9 × 103 (57) |
| PepO3 | 88 (2.7) | 79 (8.6) |
| PepF | 14 (1.3) | — |
| None[2] | 0.3 (0.2) | 28 (6.6) |

[1]nmoles substrate hydrolyzed/h/mg protein (±SE). Assays were performed using CFE from *E. coli* DH5α transformed with CNRZ32 PepO2, PepO3, or pepF genes.
[2]Assay performed using CFE from untransformed *E. coli* DH5α.

Example 4

Continued Identification and Characterization of PepO3 and Other Endopeptidase Genes A. Materials and Methods 1. Bacterial Strains, and Plasmid Strains and plasmids used in this study are presented in Table 6. *E. coli* DH5α (Gibco-BRL Life Technologies Inc., Gaithersberg, Md.) and derivatives were grown in Luria-Bertani (Sambrook et al., 1989) medium at 37° C. with aeration. *Lc. lactis* was grown at 30° C. without aeration in M17 (Difco, Detroit, Mich.) supplemented with 0.5% (w/v) glucose (G-M17), or lactose (L-M17). *Lb. helveticus* CNRZ32 was grown in MRS broth (Difco, Detroit, Mich.; 12) at 37° C. without aeration. Agar plates were prepared by adding 1.5% (wt/vol) granulated agar (Difco, Detroit, Mich.) to liquid media with or without antibiotic. To select for *E. coli* strains carrying pBluescript II SK (+) (Stratagene, La Jolla, Calif.) and its derivatives, ampicillin (Sigma, St. Louis, Mo.) was added to media to a final concentration of 100 μg/ml. Erythromycin (Em; Sigma) was added to liquid media or agar plates to select for pJDC9, pTRKH2 and their derivatives in *E. coli* and *Lc. lactis* at 500 μg/ml and 5 μg/ml, respectively. Bacteria were maintained as frozen stocks in liquid media containing 12% glycerol at −80° C.

2. Molecular Biology Techniques

DNA cloning and plasmid isolation techniques were performed according to Sambrook et al. Restriction and modifying enzymes were used according to the manufacturer's procedures (Invitrogen, Carlsbad, Calif.). Transformation of *E. coli* was performed with a Gene Pulser following the manufacturer's recommended instructions (Bio-Rad Laboratories, Richmond, Calif.). For transformation of *Lc. lactis*, the procedure of Holo and Nes (1989) was utilized. *Lb. helveticus* CNRZ32 chromosomal DNA was isolated as described by Marmur (1961). Lactococcal plasmid DNA was isolated from 50 mL culture using a modified alkaline lysis method (Sambrook et al., 1989) with an addition of lysozyme (30 mg/ml) to the resuspension buffer. For all large scale plasmid DNA extractions, final purification of DNA was conducted using mini-columns from a QiaQuick PCR-Purification kit (Qiagen, Valencia, Calif.), and DNA was dissolved in a final volume of 30-50 μL. For isolation of DNA from gels, the Qiaquick Gel Extraction kit (Qiagen) was used.

3. DNA Amplification Via PCR

The DNA primers listed in Table 7 were synthesized by Invitrogen. Amplification reactions were typically performed using Taq DNA polymerase; for high fidelity reactions, Platinum Pfx DNA polymerase (Invitrogen) was utilized. The PCR cycling conditions for amplification of DNA normally included 95° C. for 5 min, followed by 25-30 cycles of 94° C. for 30 s, 50-60° C. for 30 s, and 72° C. for 1 min per kb of the fragment amplified followed by a single cycle of 72° C. for 7 min. "Direct Colony" PCR was used to screen transformants; the fragment of interest was amplified directly from the colonies without the initial DNA template isolation. A plastic sterile pipette tip was used to pick colonies from plates and cells were mixed with 20 μL of standard PCR reaction mix containing Taq DNA polymerase (Invitrogen). To lyse the cells prior to standard cycling conditions, samples were heated to 98° C. for 10 min.

4. DNA Sequencing and Sequence Analysis

DNA sequencing was conducted with sequence-specific primers synthesized by Invitrogen (Table 7). Sequencing reactions were performed using the ABI Big Dye Reaction mix (Applied Biosystems, Foster City, Calif.), and a Perkin Elmer model 480 thermal cycler (Perkin Elmer Corp., Norwalk, Conn.). Sequence analysis was done on an ABI 377XL DNA sequencer by the Nucleic Acid and Protein facility of the University of Wisconsin Biotechnology Center (Madison, Wis.). The sequences were assembled and analyzed using Lasergene (DNASTAR Inc., Madison, Wis.) sequence analysis software.

5. Cloning of *Lb. helveticus* CNRZ32 Endopeptidases

DNA and protein analyses of the draft sequence using online BLAST search engines (on the World Wide Web at ncbi.nlm.nih.gov/BLAST/) detected several new putative endopeptidases (Table 8). *Lb. helveticus* CNRZ32 pepE2, pepF, and pepO3 genes were identified in the draft quality genome sequence of *Lb. helveticus* CNRZ32 (Table 8). Sequence specific primers were designed (Table 7) with added Bam HI and Kpn I linkers to amplify fragments including the ribosome binding site, promoter regions, coding sequence and inverted repeats present within 300-400 bp downstream of the coding sequence. The respective genes were amplified from the total genomic DNA of *Lb. helveticus* CNRZ32 using Platinum Pfx DNA polymerase (Invitrogen, Carlsbad, Calif.). The resulting amplicons were purified, digested with BamHI and KpnI and ligated to similarly double-digested pJDC9 (Chen et al., 1987) and transformed into *E. coli* DH5α. *Lb. helveticus* pepE (Fenster et al., 1997) was amplified with its native promoter from the total DNA template of *Lb. helveticus* CNRZ32 using Platinum Pfx DNA polymerase and gene specific primers (Table 7) with SmaI and XbaI linkers. The resulting amplicon of ~2.0 kb was digested with SmaI and XbaI and ligated to similarly digested pJDC9. Putative transformants were screened using gene specific primers by Direct Colony PCR. Restriction digest analysis and sequencing of the gene were performed to confirm the presence of the endopeptidase genes in pJDC9. Colonies that gave positive amplicons of expected size carried the clones of pepO3, pepF and pepE2 and pepE and were designated pSUW650, pSUW651, pSUW652 and pSUW653, respectively (Table 6). All cloned fragments were sequenced and found to be identical to the *Lb. helveticus* CNRZ32 genome sequence of the respective genes.

6. Construction of PpepO3 Translational Fusion Plasmids

The promoter region of pepO3 (GenBank accession number, AF019410, which is hereby incorporated by reference) was amplified from pSUW650 using Platinum Pfx DNA polymerase (Invitrogen, Carlsbad, Calif.) and gene specific primers, KpnI-$P_{pepO3}$—For, BamHI-$P_{pepO3}$—Rev, (Table 2). The amplified promoter fragment of pepO3 was digested using BamHI and KpnI, and ligated to similarly digested pBluescript II SK(+) (Stratagene, La Jolla, Calif.) to generate translational fusion plasmid pSUW660. The ligation mixture was electroporated into *E. coli* DH5α, and blue-white screening by α-complementation using IPTG and X-Gal (Invitrogen, Carlsbad, Calif.) was employed to screen for putative transformants. Direct Colony PCR using the above primers, restriction digest analysis and sequencing confirmed the presence of the promoter fragment of pepO3 in pSUW660.

7. Cloning of *Lb. helveticus* CNRZ32 Endopeptidases as $P_{pepO3}$ Translational Fusions The ORF of *Lb. helveticus* CNRZ32 pepO2 starting with the second codon and with transcription terminators was amplified from pSUWL29 (Table 6) via PCR using Platinum Pfx polymerase and primers, BamHI PepO2-ORF-For and XbaI PepO2-ORF-Rev (Table 7). Similarly, the ORF of *Lb. helveticus* CNRZ32 pepE and pepF starting with the second codon and with transcription terminators was amplified from genomic DNA of *Lb. helveticus* CNRZ32 via PCR using Platinum Pfx polymerase and primers, BamHI PepE-ORF-For and XbaI PepE-ORF-Rev; BamHI PepF-ORF-For and SacI PepF-ORF-Rev, respectively (Table 7). The ORFs of pepO2 and pepE were digested with BamHI and XbaI and ligated to similarly digested pSUW660 to generate pSUW661 and pSUW662, respectively (Table 6). The ORF of pepF was digested with BamHI and SacI and ligated to similarly digested pSUW660 to generate pSUW663. Ligation mixtures carrying pSUW661, pSUW662 and pSUW663 were transformed into *E. coli* ABLE C (Stratagene, La Jolla, Calif.). Putative transformants of *E. coli* ABLE C carrying pSUW661, pSUW662, and pSUW663 were screened for presence of genes pepO2, pepE and pepF, respectively via Direct Colony PCR using gene specific primers that amplified their respective ORFs. Positive endopeptidase activity confirmed the expression of the peptidases in *E. coli* ABLE C.

8. Cloning of *Lb. helveticus* CNRZ32 Endopeptidases into *Lc. lactis* Using pTRKH2

*Lb. helveticus* CNRZ32 pepO3 gene along with its promoter was cleaved from pSUW650 (Table 6) using BamHI and SacI sites and ligated to similarly digested pTRKH2 to generate pSUW664. *Lb. helveticus* CNRZ32 $P_{pepO3}$:pepO2 and $P_{pepO3}$:pepE were cleaved from pSUW661 and pSUW662, respectively, using PvuII and XbaI sites and ligated to SmaI and XbaI digested pTRKH2 to generate pSUW665 and pSUW666, respectively. *Lb. helveticus* CNRZ32 $P_{pepO3}$:pepF was cleaved from pSUW663 using PvuII and SacI and ligated to SmaI and SacI digested pTRKH2 to generate pSUW667. Ligation mixtures were electroporated into *Lc. lactis* LM0230 competent cells and transformants were isolated from LM17+Em plates after 48 hours of anaerobic incubation. Putative transformants were screened for the presence of constructs using Direct Colony PCR with primers specific to the promoter of pepO3. However, several attempts to ligate $P_{pepO3}$:pepF to pTRKH2 followed by direct transformation into *Lc. lactis* LM0230 were unsuccessful. Positive endopeptidase activity confirmed the expression of the peptidases PepO2, PepO3 and PepE in *Lc. lactis* LM0230.

9. Cell-free Extract (CFE) Preparation

Cultures were grown to late log phase ($Abs_{600\ nm}$ ~2.0) and CFEs were prepared in 50 mM 2-(N-Morpholino)ethanesulfonic acid (MES) buffer (5.0 pH). Cells were broken by vortexing with 300 mg of glass beads for 3 min using a Turbomix attachment to Vortex Gene2 (Scientific Industries, NY). CFEs from *E. coli* expressing CNRZ32 pepE, pepE2, pepF, and pepO3 translational fusion genes were assayed for endopeptidase activity against chromogenic substrates as described by Chen et al. (1987). Protein concentration of the CFEs were determined using Protein Assay Kit I from Bio-Rad and bovine serum albumin as the protein standard.

10. Preparation of CCS

CCS was prepared as described by Morris et al. (1988) using custom made molds designed by Hassan. (2001). Briefly, 850 g of a three-week-old Cheddar cheese was grated and mixed with an equal quantity of sea sand. The sea sand-cheese mixture was placed in custom made molds and squeezed using a Carver manual hydraulic press model no. 3912 (Fred S. Carver, Inc., Summit, N.J.). Pressure was gradually increased up to 10,000 psi and held at that pressure for ~3 h. The CCS and cheese liquid fat were collected and kept at 4° C. for 2 hours. This storage temperature allowed the expressed fat to solidify as the upper layer, which was removed using a spatula. Residual fat was removed by centrifugation at 1380×g for 10 minutes using an induction drive centrifuge model J2-21M (Beckman Coulter). Additionally, CCS was filtered using a 1.6 μm glass microfiber filter (Whatman International Ltd., England). The CCS was filtered sterilized by sequential passages through 0.45μ, and 0.22μ cellulose nitrate filters (Nalgene Filtration Products, Rochester, N.Y.) and stored at −80° C. For peptide hydrolysis, CCS was prepared as described above, boiled for 5 min at 100° C., extracted with equal volumes of 100% ethyl ether, vacuum dried using a Savant Speed Vac (SC 210A; Global Medical Instrumentation, Inc., Albertville, Minn.) resuspended in MES buffer, pH 5.0 (50 mM) buffer and concentrated 2× times to yield an effective reaction system.

11. Synthesis of Peptide Substrates

The peptides β-CN (f193-209), $\alpha_{S1}$-CN (f1-9), $\alpha_{S1}$-CN (f1-13), and $\alpha_{S1}$-CN (f1-16), and $\alpha_{S1}$-CN (f1-6) were synthesized at the University of Wisconsin Biotechnology Center. The synthesized peptides were subsequently purified by collection of appropriate fractions from preparatory RP-HPLC. The peptides were analyzed by mass spectrometry (MS) using a Bruker Reflex II for matrix-assisted laser desorption/ionization time of flight (MALDI-TOF). The peptides were lyophilized and stored at −80° C. Stock solutions were prepared in sterile double distilled water and also stored at −80° C.

12. Peptide Hydrolysis Reactions

Peptide hydrolysis reactions with *E. coli* and *Lc. lactis* CFE were performed in 50 μL total volume. Each sample contained 10 μL of CFE (~2.0 mg/mL protein), 10 μL of peptide and 30 μL of buffer. The buffer used for single peptide reaction and defined peptide mix was 120 mM MES (pH 5.1)/0.68 M NaCl (4% NaCl). CCS concentrate with a final pH of 5.2 and the 4% salt concentration was used for the cheese model system. The reactions were initiated by the addition of the substrate and the samples were incubated at 10° C. for predetermined times. Initial substrate concentrations in the reaction samples were 1 mg/mL for β-CN (f193-209) and 10 mg/mL for $\alpha_{S1}$-CN (f1-9). In the defined peptide mix reactions, peptides $\alpha_{S1}$-CN (f1-13), and $\alpha_{S1}$-CN (f1-16), and $\alpha_{S1}$-CN (f1-6) were present at 5, 2.5 and 1 mg/ml concentrations, respectively. Reactions were stopped by addition of trifluoroacetic acid (TFA) to a 5% final concentration, samples were frozen at −20° C. until analysis.

13. Peptide Separation and Identification of Hydrolysis Products

Peptides were separated by RP-HPLC on a HP1100 series (Agilent Technologies, Palo Alto, Calif.) system, using solvent A (0.1% TFA in HPLC grade water) and solvent B (0.085% TFA, 80% acetonitrile, 20% HPLC grade water). The samples were analyzed on a AllTech Ultima $C_{18}$ column (250×2.1 mm, 5 micron particle size, 100 Å pore size; Alltech Associates Inc., Deerfield, Ill.). The initial condition was 10% B, and a linear gradient from 10% to 60% was generated over 35 min for separation of β-CN (f193-209), the defined peptide mix and CCS samples. A linear gradient from 10-20% was generated over 15 min for separation of $\alpha_{S1}$-CN (f1-9) at a flow rate of 0.25 ml/min at 25° C. The eluted peaks were detected by absorbance at 214 nm using a photodiode array detector spectrometer (HP1100 series). Before injection, samples inactivated with TFA were thawed at room temperature and centrifuged (14,000×g for 5 min at 25° C.); 20 μl of the supernatant were directly injected into the column using a HP1100 series autosampler equipped with a dilutor module containing a water:acetonitrile wash solution (1:1; Agilent Technologies, Palo Alto, Calif.). Substrate concentration was determined by peak area. Substrate was hydrolyzed to ~10-20% and reaction rates were verified to be in the linear range when calculating slope for specific activity determinations. Specific activity was calculated as nmoles hr-1 mg-1 protein and reported values are corrected by subtracting the mean values obtained in the control treatments. In case of $\alpha_{S1}$-CN (f1-9) hydrolysis, average specific activity was calculated since the initial lag phase was included in the calculation.

The masses of RP-HPLC separated peptide fractions were determined by using a triple quadruple mass spectrometer (Micromass Quattro II, Micromass Ltd. Manchester, UK) with electrospray ionization sources at the University of Wisconsin Biotechnology Center. To identify the hydrolysis products, the masses were compared to calculated molecular masses of peptides and/or aminoacids derived from β-CN (f193-209) and $\alpha_{S1}$-CN (f1-9). Sample preparation and identification of CCS peptides using tandem mass spectrometry was performed at the University of Wisconsin Biotechnology Center. Data dependent MS/MS switching on Q-TOF was done using MassLynx software. Raw data was analyzed using MASCOT (Matrix Science Ltd., London, UK) and Spectrum Mill (Agilent Technologies) software allowing for oxidized methionine and phospho tyrosine and serine modifications. SWISS PROT database search was used for peptide search.

14. Statistical Analysis

The rates of hydrolysis of the peptides were compared as a function of time and calculated the specific activities in nmoles of peptide hydrolyzed per hour per mg protein. Results reported are mean values ± standard deviation of three independent trials, corrected by subtracting the values obtained in the control treatments. Values are reported as significantly different when a P-value of $\leqq 0.05$ was obtained using Student's t test. A single factor ANOVA was performed and the least significant differences were calculated (SAS User's Guide: Statistics, 1985) for separation of means for individual peptidases within single peptide peptide reactions, the defined mixture of cheese-derived peptides, and in CCS.

15. Nucleotide Sequence Accession Number

The nucleotide sequence of pepO3, pepF and pepE2 have been deposited in the GenBank database under accession numbers AY355128, AY365129 and AY365130, respectively.

B. Results

1. Sequence Analysis

The ORF of pepO3 was 1929 bp encoding a polypeptide of 643 amino acid residues with a deduced mass of 71.4 kDa (accession number AY355128). PepO3 was 62% identical to PepO2 and PepO in *Lb. helveticus* CNRZ32 (accession numbers AF321529 and AF019410, respectively) and 78% identical to a hypothetical protein in *Lb. gasseri* (protein accession number ZP_00045894.1). The pepF ORF was 1794 bp encoding a polypeptide of 598 amino acid residues with a deduced mass of 66.4 kDa (AY365129). PepF has 52%, and 46% identity to previously characterized PepF proteins from *Lb. plantarum* (protein accession number NP_785715.1) and *Lc. lactis* (accession number A55485), respectively. It has 75% identity to a hypothetical protein from *Lb. gasseri* (protein accession number ZP_00046654.1). The pepE2 ORF was $^{1311}$ bp encoding a polypeptide of 437 amino acid residues with a deduced mass of 48.5 kDa (accession number AY365130). PepE2 has 52% identity to previously characterized PepE protein from *Lb. helveticus* CNRZ32 (accession number AAB52540) and 80% identity to a hypothetical protein from *Lb. gasseri* (protein accession number ZP_00047232.1). The ORFs of pepO3 and pepF contain the sequence HEISH and HETGH, which is characteristic of the HEXXH-motif present in zinc metallopeptidases (Barret et al., 1998). The amino acid residues important for substrate binding and catalysis by cysteine proteinases of prokaryotic and eukaryotic origin are conserved in PepE2 (Fenster et al., 1997).

2. Identification of Peptides from CCS

The peptide/protein summary of CCS generated by Spectrum Mill (Agilent Technologies, Foster City, Calif.) and MASCOT (Matrix Science Ltd., London UK) identified peptides and phosphopeptides mostly from $\alpha_{S1}$- and β-CN. The majority of the peptides identified from β-CN were from premature β-CN, β-CN (f60-81) and β-CN (f107-118). β-CN (f193-209) was not identified. The peptides identified from $\alpha_{S1}$-CN were $\alpha_{S1}$-CN (f1-9), $\alpha_{S1}$-CN (f1-13), $\alpha_{S1}$-CN (f1-16), $\alpha_{S1}$-CN (f1-17), $\alpha_{s1}$-CN (f24-41) and $\alpha_{S1}$-CN (f24-39).

3. Peptide Hydrolysis and Specificity Using *E. coli* CFE

CFE of *E. coli* derivatives expressing PepO2, and PepO3 had significantly greater activity than the control with both β-CN (f193-209) and $\alpha_{S1}$-CN (f1-9), with highest activity detected with PepO2 (Table 9). PepF activity was detected with β-CN (f193-209) but not with $\alpha_{S1}$-CN (f1-9). PepO, PepE and PepE2 activities were not observed with either peptide.

Figure 6:
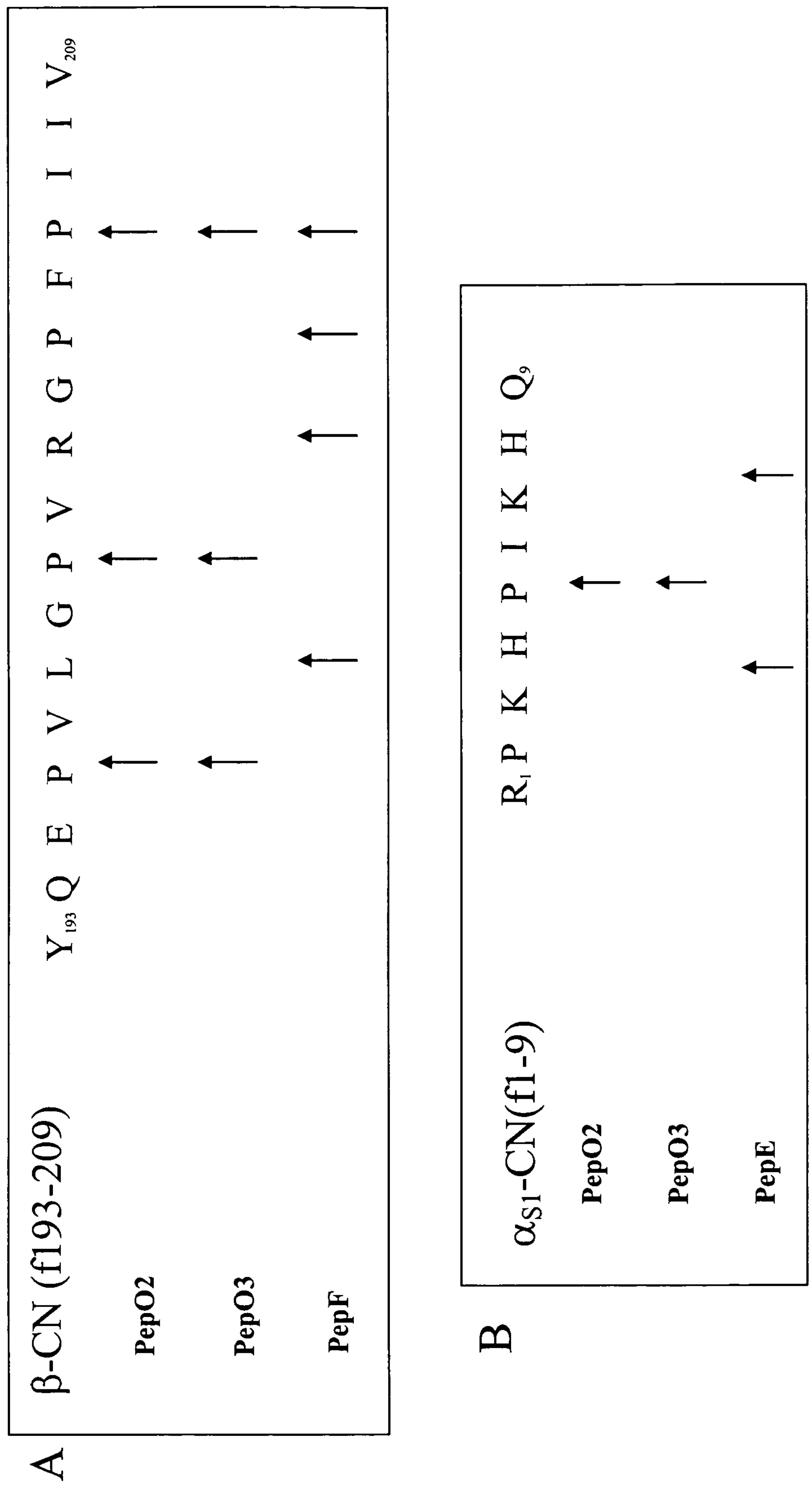
FIG. 6. Specificity of *Lactobacillus helveticus* CNRZ32 endopeptidases toward β-casein (f193-209) (SEQ ID NO:12) and $\alpha_{S1}$-casein (f1-9) (SEQ ID NO:5) under cheese ripening conditions (pH 5.0-5.2, 4% NaCl, 10° C.).

The hydrolysis specificities of PepO2, PepO3, PepE and PepF with β-CN (f193-209) and $\alpha_{S1}$-CN (f1-9), are presented in FIG. 6. PepO3 was determined to be a post-proline endopeptidase, similar to PepO2, capable of hydrolyzing bonds $Pro_{(206)}$-$Ile_{(207)}$, $Pro_{(196)}$-$Val_{(197)}$, and $Pro_{(200)}$-$Val_{(201)}$ and bonds $Pro_{(5)}$-$Ile_{(6)}$ of β-CN(f193-209) and $\alpha_{S1}$-CN (f1-9), respectively (FIG. 6). PepF also hydrolyzed post-proline bonds $Pro_{(204)}$-$Phe_{(205)}$ and $Pro_{(206)}$-$Ile_{(207)}$ but additionally hydrolyzed X-Gly bonds, $Lys_{(198)}$-$Gly_{(199)}$, and $Arg_{(202)}$-$Gly_{(203)}$ of β-CN(f193-209), and PepE hydrolyzed $\alpha_{S1}$-CN (f1-9) at bonds $Lys_{(3)}$-$His_{(4)}$ and $Lys_{(7)}$-$His_{(8)}$.

4. Peptide Hydrolysis Using *Lc. lactis* CFE

Figure 7:
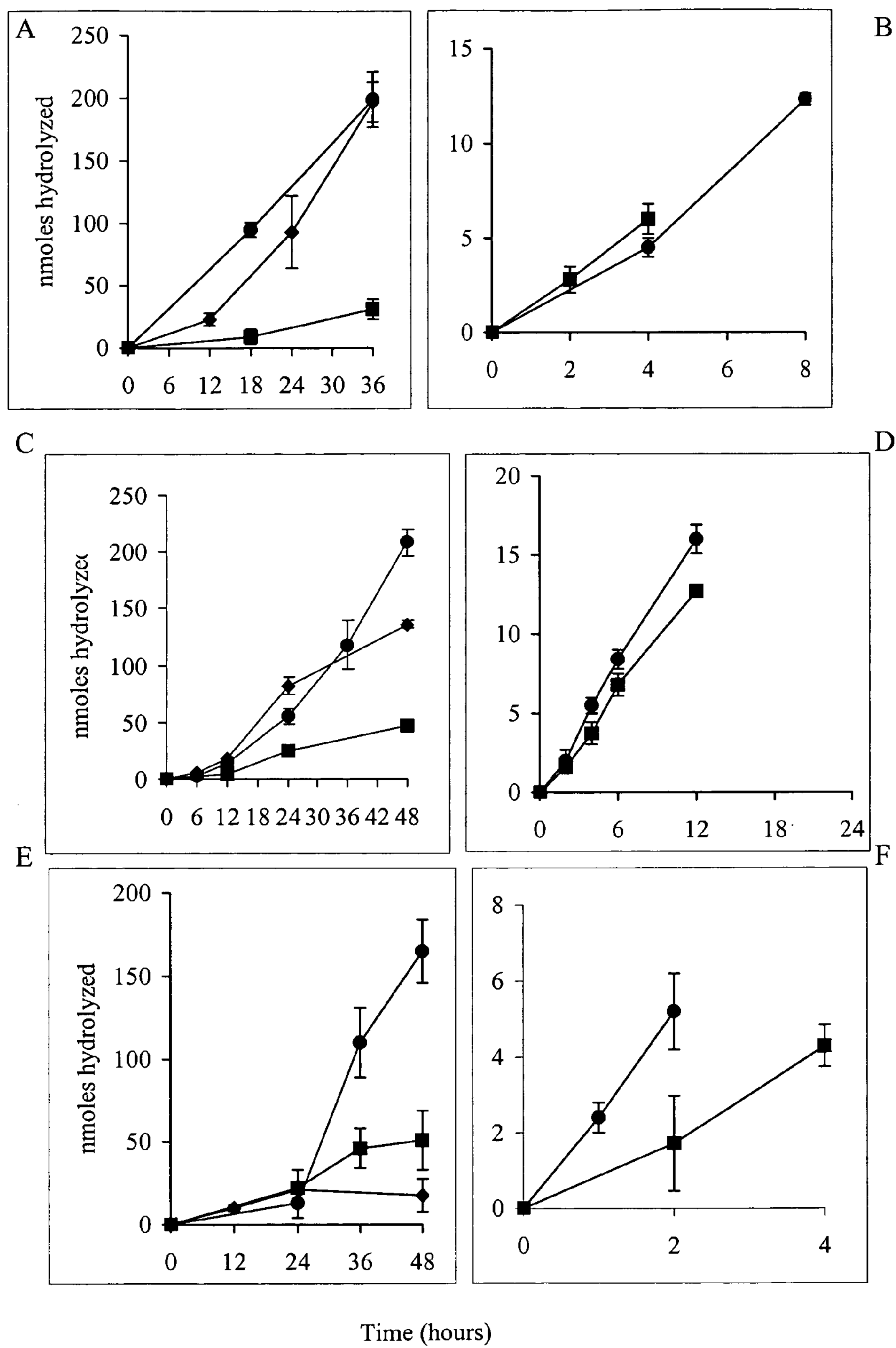
FIG. 7. Rate of β-casein (f193-209) (right panel) and $\alpha_{s1}$-casein (f1-9) (left panel) hydrolysis at pH 5.0-5.2, 4% NaCl at 10° C. in single peptide system (A, B), defined peptide mix system (C, D), and in Cheddar cheese serum (E, F) by cell-free extract from *Lactococcus lactis* LM0230 derivatives expressing *Lactobacillus helveticus* CNRZ32 endopeptidases PepO2 (circles), PepO3 (squares), and PepE (diamonds). Values are corrected by subtracting the values obtained in the control treatments. Error bars represent one standard error of the mean (n=3).
Figure 8:
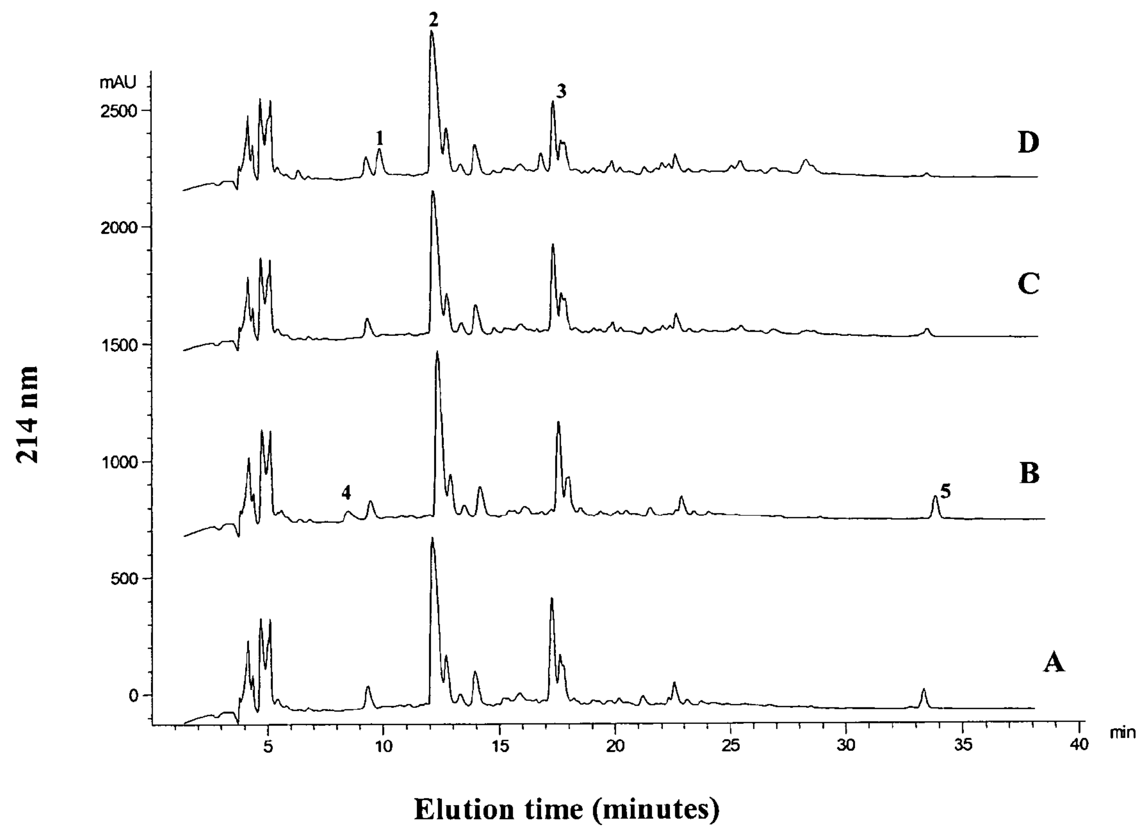
FIG. 8. RP-HPLC chromatograms of the products from the hydrolysis of peptides in Cheddar cheese serum (CCS) spiked with $\alpha_{s1}$-casein (f1-9) and β-casein (f193-209) at 10 mg/mL and 1 mg/mL, respectively. Incubations for 12 h with cell free extract of *Lactococcus lactis* LM0230 control (A) and its derivatives expressing *Lactobacillus helveticus* CNRZ32 PepE (B); PepO3 (C); PepO2 (D) in CCS at 4% NaCl and at pH 5.2 and 10° C. Peptides identified in the chromatograms include peak 1, $\alpha_{s1}$-casein (f1-5); peak 2, $\alpha_{s1}$-casein (f1-9); peak 3, $\alpha_{s1}$-casein (f1-13); peak 4, $\alpha_{s1}$-casein (f4-9); and peak 5, β-casein (f193-209).

The time course of hydrolysis for $\alpha_{S1}$-CN (f1-9) in single peptide, defined peptide mix and CCS exhibited a slower initial rate (lag phase), which increased after 12 h of incubation until 48 hours with CFE of LM0230 expressing PepO2, PepO3 and PepE (f1-9) (FIG. 7). A lag phase was not observed when lower concentrations (1 mg/ml) of $\alpha_{S1}$-CN (f1-9) were used, suggesting that substrate inhibition maybe occurring at higher concentrations. LM0230 derivatives expressing PepO2 and PepO3 under the control of the pepO3 promoter hydrolyzed both β-CN (f193-209) and $\alpha_{S1}$-CN (f1-9) at a significantly greater rate than the controls in all three systems (FIG. 7, Table 10). The peptide β-CN (f193-209) was hydrolyzed completely within 12 hours when spiked CCS was incubated with CFE of strains expressing PepO2 or PepO3 (FIG. 8). The activity of PepO2 with β-CN (f193-209) was 2-fold higher in CCS than alone or in the defined peptide mix (Table 10). The activity of PepO2 with $\alpha_{S1}$-CN (1-9) was reduced in CCS and the defined peptide mix, when compared to activity observed on $\alpha_{S1}$-CN (1-9) alone (Table 11).

Figure 9:
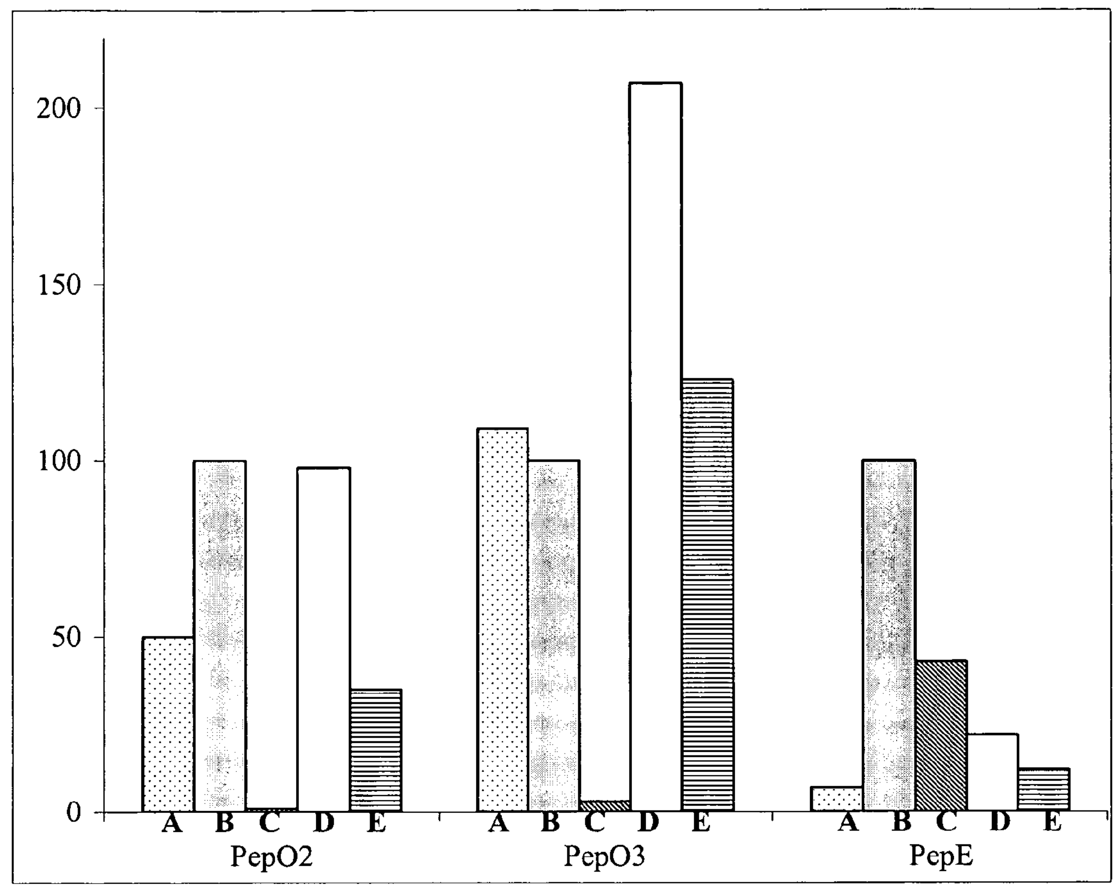
FIG. 9. Relative activity of *Lactococcus* lactis LM0230 derivatives expressing *Lactobacillus helveticus* CNRZ32 PepO2, PepO3 and PepE towards peptides in the defined peptide mix, at pH 5.0-5.2, 4% NaCl, and 10° C. (A) β-casein (f193-209); (B) $\alpha_{s1}$-casein (f1-9); (C) $\alpha_{s1}$-casein (f1-6); (D) $\alpha_{s1}$-casein (f1-13); and (E) $\alpha_{s1}$-casein (f1-16). Values are corrected by subtracting the values obtained in the control treatments. Activity with $\alpha_{s1}$-casein (f1-9) was arbitrarily set to 100%.

LM0230 derivatives expressing PepE hydrolyzed $\alpha_{S1}$-CN (f1-9) at a significantly greater rate than control in single peptide and defined peptide mix systems (FIG. 7, Table 11). In CCS, its activity was significantly inhibited although the expected hydrolysis products were seen in the RP-HPLC chromatogram (FIG. 8, Table 11). There was also higher background activity detected in the CFE of control strain of *Lc. lactis* LM0230 for peptides $\alpha_{S1}$-CN (f1-9) and β-CN (f193-209) in CCS than in single peptide reactions or in the defined peptide mix; however, the peptide profile of control strain was similar to that observed at time zero (FIG. 8). Relative activity towards the other peptides in the defined peptide mix was also calculated, with activity towards $\alpha_{S1}$-CN (f1-9) taken as 100% (FIG. 9). Each peptidase hydrolyzed the different peptides at different rates. For e.g., amongst the $\alpha_{S1}$-CN derived peptides, PepE had highest activity towards $\alpha_{S1}$-CN (f1-9) and $\alpha_{S1}$-CN (f1-6); PepO2 had highest activity towards peptides $\alpha_{S1}$-CN (f1-9), and $\alpha_{S1}$-CN (f1-13), and PepO3 had highest activity towards $\alpha_{S1}$-CN (f1-13) (FIG. 9).

TABLE 6

List of bacterial strains and plasmids

| Strain or plasmid | Relevant characteristics | Source or reference |
|---|---|---|
| *Escherichia coli* | | |
| DH5α | *E. coli* strain with high efficiency cloning, enables α-complementation | Bethesda Research Lab |
| ABLE C | *E. coli* cloning strain reduces copy number of ColE1 based vectors by 4 fold | Strategene, La Jolla, CA |
| *Lactobacillus helveticus* | | |
| CNRZ32 | Wild type | Laboratory strain |
| *Lactococcus lactis* | | |
| LM0230 | Plasmid free | Efstathiou and Mckay, 1976 |
| pTRKH2 | $Em^r$ lacZ; 6.9 kb | O'Sullivan and Klaenhammer, 1993 |
| pJDC9 | $Em^r$ lacZ; 6.85 kb | Chen and Morrison, 1987 |
| pTRKH-N | 3.8 kb SmaI-SalI fragment containing Lb. helveticus CNRZ32 ligated into pTRKH2; $Em^r$; 11 kb pepN | Christensen, 1995 |
| pBlueskript II $SK^+$ | f1 origin in +/− orientation, $Amp^r$ lacZ; 2.96 kb | Strategene, Inc. |
| pSUWL29 | 3.0 kb PstI fragment containing CNRZ32 pepO2 ligated into pJDC9; ~9.0 kb | Chen, 2001 |
| pSUW650 | 2.6 kb BamHI-KpnI fragment containing pepO3 ligated into pJDC9 | This study |
| pSUW651 | 2.5 kb BamHI-KpnI fragment containing pepF ligated into pJDC9 | This study |
| pSUW652 | 2.1 kb BamHI-KpnI fragment containing pepE2 ligated into pJDC9 | This study |
| pSUW653 | 2.0 kb SmaI-XbaI fragment containing pepE ligated into pJDC9 | This study |
| pSUW660 | 0.2 kb KpnI-BamHI fragment containing CNRZ32 $P_{pepO3}$ ligated into pBlueskript II $SK^+$ | This study |
| pSUW661 | 2.4 kb BamHI-XbaI ORF containing CNRZ32 pepO2 ligated into pSUW660 | This study |
| pSUW662 | 1.7 kb BamHI-XbaI ORF containing CNRZ32 pepE ligated into pSUW660 | This study |
| pSUW663 | 2.5 kb BamHI-SacI ORF containing CNRZ32 pepF ligated into pSUW660 | This study |
| pSUW664 | 2.6 kb PCR fragment containing CNRZ32 pepO3 from pSUW650 ligated into pTRKH2 | This study |
| pSUW665 | 2.6 kb PvuII-XbaI fragment containing CNRZ32 pepO2 from pSUW661 ligated into pTRKH2 | This study |
| pSUW666 | 1.9 kb PvuII-XbaI fragment containing CNRZ32 pepE from pSUW662 ligated into pTRKH2 | This study |

TABLE 6-continued

List of bacterial strains and plasmids

| Strain or plasmid | Relevant characteristics | Source or reference |
|---|---|---|
| pSUW667 | 2.9 kb PvuII-SacI fragment containing CNRZ32 pepF from pSUW663 ligated into pTRKH2 | This study |

TABLE 7

List of sequence specific primers[1].

| Primer name | Description or purpose | Sequence, 5'-3' |
|---|---|---|
| PepO3-For-BamHI | forward; amplification of pepO3 | CGGGATCCTTTTGACTTTGGGTGAAT (SEQ ID NO:36) |
| PepF-For-BamHI | forward; amplification of pepF | CGGGATCCCTTAAGGGAGTTCGGAG (SEQ ID NO:37) |
| PepE2-For-BamHI | forward; amplification of pepE2 | CGGGATCCTATAACAAGAACGCTAAGAA (SEQ ID NO:38) |
| PepE-For-SmaI | forward; amplification of pepE | TCCCCCGGGATTAGATTAAGCAAG (SEQ ID NO:39) |
| PepO3-Rev-KpnI | reverse; amplification of pepO3 | GGGGTACCACGAGAAGTGGTTAGTTGA (SEQ ID NO:40) |
| PepF-Rev-KpnI | reverse; amplification of pepF | GGGGTACCTTGGAGGAATTCATCTTTAG (SEQ ID NO:41) |
| PepE2-Rev-KpnI | reverse; amplification of pepE2 | GGGGTACCCAGATAATGGCAAATGATA (SEQ ID NO:42) |
| PepE-Rev-XbaI | reverse; amplification of pepE | GCTCTAGAGAAATTCGCCCTGGTC (SEQ ID NO:43) |
| KpnI $P_{pepO3}$-For | forward; amplification of $P_{pepO3}$ | GGGGTACCGACTTTGGGTGAATC (SEQ ID NO:44) |
| BamHI $P_{pepO3}$-Rev | reverse; amplification of $P_{pepO3}$ | CGGGATCCCATTTTATTATTCAAAGAGAA (SEQ ID NO:45) |
| BamHI PepF-ORF-For | forward; amplification of pepF ORF | CGGGATCCCCAACAAGAAGCGAAGTC (SEQ ID NO:46) |
| SacI PepF-ORF-Rev | reverse; amplification of pepF ORF | GCTGGAGCTCGTCAGCTTTTTGTATGG (SEQ ID NO:47) |

TABLE 7-continued

List of sequence specific primers[1].

| Primer name | Description or purpose | Sequence, 5'-3' |
|---|---|---|
| BamHI PepO2-ORF-For | forward; amplification of pepO2 ORF | CGCGGATCCAATTTAGCAAAAATC (SEQ ID NO:48) |
| XbaI PepO2-ORF-Rev | reverse; amplification of pepO2 ORF | GCTCTAGATCAATTATATAACTGATAC (SEQ ID NO:49) |
| BamHI PepE-ORF-For | forward; amplification of pepE ORF | CGGGATCCGAATTAACTGTGCAGG (SEQ ID NO:50) |
| XbaI PepE-ORF-Rev | reverse; amplification of pepE ORF | GCTCTAGAGAAATTCGCCCTGGTC (SEQ ID NO:51) |

[1]The restriction sites flanking each primer is underlined and the name of the site is included in the primer name

TABLE 8

*Lactobacillus helveticus* CNRZ32 genes encoding known or putative endopeptidases.

| Gene | Known (reference) or predicted product |
|---|---|
| pepE | Thiol-dependent endopeptidase |
| pepE2 | PepE paralog; 53% identical to CNRZ32 endopeptidase PepE |
| pepF | PepF ortholog; 53% identical to *Lactococcus lactis* endopeptidase PepF |
| pepO | Endopeptidase O ortholog |
| pepO2 | Post-prolyl endopeptidase |
| pepO3 | PepO/PepO2 paralog; 62% identical to CNRZ32 endopeptidases PepO and PepO2 |
| gcp | Gcp ortholog; 63% identical to predicted O-sialoglycoprotein endopeptidase Gcp from *Lactobacillus plantarum* |
| ydiC | glycoprotein endopeptidase ortholog; 37% identical to predicted glycoprotein endopeptidase from *Lactobacillus plantarum* |

TABLE 9

Specific activity of cell free extract of *Escherichia coli* DH5α expressing *Lactobacillus helveticus* CNRZ32 endopeptidases toward β-casein (f193-209) and $\alpha_{S1}$-casein (f1-9)[1].

| Strain | $\alpha_{S1}$-casein (f1-9) | β-casein (f193-209) |
|---|---|---|
| DH5α (pSUWL29) | 3700 (19)$^a$ | 290 (19)$^a$ |
| DH5α (pSUW650) | 85 (21)$^b$ | 88 (5.0)$^b$ |
| DH5α (pSUW51) | N. D | N. D |
| DH5α (pSUW651) | N. D | 14 (3.0)$^c$ |
| DH5α (pSUW652) | N. D | N. D |
| DH5α (pSUW653) | N. D | N. D |

[1]nmoles substrate hydrolyzed/h/mg protein (±SD). Values were corrected by subtracting the mean values obtained in the control treatments from CFE of *Escherichia coli* DH5α(pJDC9). Means (±SD) with different letters are statistically different within a column at $\alpha \leqq 0.05$.
[2]Assays were performed at cheese ripening conditions (pH 5.0-5.2, 4% NaCl, 10° C.) using CFE from *Escherichia coli* DH5α (pJDC9) transformed with CNRZ32 pepO2 (pSUWL29), pepO3 (pSUW650), pepO (pSUW51), pepF (pSUW651) pepE2 (pSUW652), or pepE (pSUW653).
N. D = Not detected

TABLE 10

Specific activity[1] of cell-free extract of *Lactococcus lactis* LM0230 expressing *Lactobacillus helveticus* CNRZ32 endopeptidases toward β-casein (f193-209) as an individual peptide, in the defined peptide mix, and in Cheddar cheese serum.

| Peptidase2 | Single peptide reaction | Defined peptide mix | Cheddar cheese serum |
|---|---|---|---|
| PepO2 | 64 (1.5)$^{a, B}$ | 42 (10)$^{a, B}$ | 120 (32)$^{a, A}$ |
| PepO3 | 81 (7.0)$^{a, A}$ | 40 (6.0)$^{a, B}$ | 61 (23)$^{b, A}$ |
| PepE | N. D | N. D | N. D |

[1]nmoles substrate hydrolyzed/h/mg protein (±SD). Values were corrected by subtracting the mean values obtained in the control treatments. Means (±SD) with different lower case letters within a column and with different upper case letters within a row, respectively, are statistically different at $\alpha \leqq 0.05$.
N. D = Not detected

TABLE 11

Specific activity[1] of cell-free extract of *Lactococcus lactis* LM0230 expressing *Lactobacillus helveticus* CNRZ32 endopeptidases toward $\alpha_{S1}$-casein (f1-9) as an individual peptide, in the defined peptide mix and in Cheddar cheese serum.

| Peptidase2 | Individual peptide reaction | Defined peptide mix | Cheddar cheese serum |
|---|---|---|---|
| PepO2 | 240 (10)$^{a, A}$ | 84 (20)$^{b, C}$ | 150 (40)$^{a, B}$ |
| PepO3 | 41 (19)$^{b, A}$ | 38 (9.0)$^{c, A}$ | 63 (25)$^{b, A}$ |
| PepE | 190 (14)$^{a, A}$ | 120 (7)$^{a, B}$ | 31 (17)$^{c, C}$ |

[1]nmoles substrate hydrolyzed/h/mg protein (±SD). Values were corrected by subtracting the mean values obtained in the control treatments. Means (±SD) with different lower case letters within a column and with different upper case letters within a row, respectively, are statistically different at $\alpha \leqq 0.05$.
[2]Assays were performed under cheese ripening conditions, pH 5.0-5.2, 4% NaCl, at 10° C.; using cell free extract from *Lactococcus lactis* LM0230 derivatives expressing CNRZ32 PepO2, PepO3 and PepE.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

U.S. Pat. No. 4,683,202
U.S. Pat. No. 4,684,611
U.S. Pat. No. 4,879,236
U.S. Pat. No. 4,952,500
U.S. Pat. No. 5,106,631
U.S. Pat. No. 5,302,523
U.S. Pat. No. 5,322,783
U.S. Pat. No. 5,356,639
U.S. Pat. No. 5,384,253
U.S. Pat. No. 5,387,422

U.S. Pat. No. 5,395,631
U.S. Pat. No. 5,429,829
U.S. Pat. No. 5,462,755
U.S. Pat. No. 5,464,765
U.S. Pat. No. 5,505,979
U.S. Pat. No. 5,538,877
U.S. Pat. No. 5,538,880
U.S. Pat. No. 5,547,691
U.S. Pat. No. 5,550,318
U.S. Pat. No. 5,554,398
U.S. Pat. No. 5,563,055
U.S. Pat. No. 5,580,579
U.S. Pat. No. 5,580,859
U.S. Pat. No. 5,589,466
U.S. Pat. No. 5,591,616
U.S. Pat. No. 5,610,042
U.S. Pat. No. 5,635,228
U.S. Pat. No. 5,641,515
U.S. Pat. No. 5,643,621
U.S. Pat. No. 5,656,610
U.S. Pat. No. 5,688,542
U.S. Pat. No. 5,702,932
U.S. Pat. No. 5,736,524
U.S. Pat. No. 5,780,448
U.S. Pat. No. 5,789,215
U.S. Pat. No. 5,792,451
U.S. Pat. No. 5,853,786
U.S. Pat. No. 5,871,986
U.S. Pat. No. 5,888,966
U.S. Pat. No. 5,928,906
U.S. Pat. No. 5,945,100
U.S. Pat. No. 5,948,459
U.S. Pat. No. 5,981,274
U.S. Pat. No. 5,988,052
U.S. Pat. No. 5,994,624
U.S. Pat. No. 6,020,324
U.S. Pat. No. 6,026,740
U.S. Pat. No. 6,103,277
U.S. Pat. No. 6,120,809
U.S. Pat. No. 6,127,142
U.S. Pat. No. 6,139,889
U.S. Pat. No. 6,140,078
U.S. Pat. No. 6,183,804
U.S. Pat. No. 6,242,036
U.S. Pat. No. 6,258,390
U.S. Pat. No. 6,270,823
U.S. Pat. No. 6,297,042
U.S. Pat. No. 6,299,896
U.S. Pat. No. 6,335,040
U.S. Pat. No. 6,335,040
U.S. Pat. No. 6,399,121
U.S. Pat. No. 6,401,604
U.S. Pat. No. 6,410,076
U.S. Pat. No. 6,413,568
U.S. Pat. No. 6,416,797
U.S. Pat. No. 6,443,379
U.S. Pat. No. 6,455,092
U.S. Pat. No. 6,458,394
U.S. Pat. No. 6,465,033
U.S. Pat. No. 6,468,570
U.S. Pat. No. 6,475,538
U.S. Pat. No. 6,485,762
U.S. Pat. No. 6,548,089
U.S. Pat. No. 6,548,089
U.S. Pat. No. 6,551,635
U.S. Pat. No. 6,558,716
U.S. Pat. No. 6,572,901

Altschul et al., *J. Mol. Biol.,* 215:403-410, 1990.
Arora et al., Handbook of Fungal Biotechnology (Marcel Dekker), 2003.
Ausubel et al., In: *Current Protocols in Molecular Biology*, John, Wiley & Sons, Inc, New York, 1996.
Bartels et al., *Milchwissenschaft,* 42:139-144, 1987b.
Bartels et al., *Milchwissenschaft,* 42:83-88, 1987a.
Benyx, Protein Expression Technologies: Current Status and Future Trends (Horizon Bioscience), 2004.
Broadbent et al., *Appl. Environ. Microbiol.,* 68:1778-1785, 2002.
Broadbent et al., *J. Dairy Sci.,* 81:327-337, 1998.
Carbonelli et al., *FEMS Microbiol. Lett.,* 177(1):75-82, 1999.
Chavagnat et al., *FEMS Microbiol. Lett.,* 191:79-85, 2000.
Chen and Morrison, *Gene,* 64:155-164, 1988.
Chen and Okayama, *Mol. Cell Biol.,* 7(8):2745-2752, 1987.
Chen and Steele, *Appl. Environ. Microbiol.,* 64:3411-3415, 1998.
Chen et al., *Appl. Environ. Microbiol.,* 2002.
Chen et al., *Appl. Environ. Microbiol.,* 64:3411-3415, 1998.
Chen et al., *Appl. Environ. Microbiol.,* 69:1276-1282, 2003.
Christensen et al., *Antonie van Leeuwenhoek,* 76:217-246, 1999.
Christensen et al., *Appl Environ Microbiol.,* 69(2):1283-1286, 2003.
Christensen et al., *Gene,* 164:89-93, 1995b.
Christensen et al., *Intl. Dairy J,* 5:367-369, 1995a.
Christensen, In: Peptidases of *Lactobacillus helveticus*: role in physiology and casein hydrolysis, University of Wisconsin-Madison, 2000.
Christensson et al., *Appl. Environ. Microbiol.,* 68:254-262, 2002.
Cocea, *Biotechniques,* 23(5):814-816, 1997.
DeMan et al., *J. Appl. Bacteriol.,* 23:130-135, 1960.
Detmers et al., *Biochem.,* 37:16671-16679, 1998.
Efstathiou and Mckay, *J. Bacteriol.,* 130:257-265, 1976.
Exterkate and Alting, *Int. Dairy J.,* 5:15-28, 1995.
Fechheimer et al., *Proc. Natl. Acad. Sci. USA,* 84:8463-8467, 1987.
Fenster and Steele, J. Appl. Microbiol., 88(4):572-583, 2000.
Fenster et al., *J. Bacteriol.,* 179:2529-2533, 1997.
Fraley et al., *Proc. Natl. Acad. Sci. USA,* 76:3348-3352, 1979.
Froeliger et al., *Infect. Immun.,* 67:5206-5214, 1999.
Gomez et al., *Milchwissenschaft,* 51:315-319, 1996.
Gopal, *Mol. Cell. Biol.,* 5:1188-1190, 1985.
Graham and Van Der Eb, *Virology,* 52:456-467, 1973.
Harland and Weintraub, *J. Cell Biol.,* 101(3):1094-1099, 1985.
Hassan et al., *Int. J. Food Microbiol.,* 64(1-2):199-203, 2001.
Hellendoom et al., University of Groningen, Kerklaan 30, Haren 9751 NN, Netherlands, 1999.
Holo and Nes, *Appl. Environ. Microbiol.,* 55:3119-3123, 1989.
Hwang et al. *Crit. Rev. Ther. Drug Carrier Syst.,* 15(3):243-284, 1998.
Inouye and Inouye, *Nucleic Acids Res.,* 13:3101-3109, 1985.
Johnson et al., In: *Biotechnology And Pharmacy*, Pezzuto et al. (Eds.), Chapman and Hall, NY, 1993.
Kaeppler et al., *Plant Cell Reports,* 9:415-418, 1990.
Kaminogawa et al., *J. Food Sci.,* 51:1253-1264, 1986.
Kaneda et al., *Science,* 243:375-378, 1989.
Kato et al, *J. Biol. Chem.,* 266:3361-3364, 1991.
Khalid and Marth, *Appl. Environ. Microbiol.,* 56:381-388, 1990.
Khalid et al., *J. Dairy Sci.,* 74:29-45, 1991.

Kok and De Vos, In: *Genetics and biotechnology of lactic acid bacteria*, Glasson and de Vos (Eds.), Blackie Academic and Professional, Glasgow, 1994.
Kunji et al., *Antonie van Leeuwenhoek,* 70:187-221, 1996.
Kyte and Doolittle, *J. Mol. Biol.,* 157:105-132, 1982.
Lee et al., *J. Dairy Sci.,* 79:1521-1528, 1996.
Lemieux and Simard, *Lait.,* 71:599-636, 1991.
Levenson et al., *Hum. Gene Ther.,* 9(8):1233-1236, 1998.
Madkor et al., *J. Dairy Sci.,* 83:1684-1691, 2000.
Mathiowitz et al., *Nature,* 386(6623):410-414, 1997.
Mierau et al., *J. Bacteriol.,* 175:2087-2096, 1993.
Monnet et al., *J. Biol. Chem.,* 269:32070-32073, 1994.
Mulholland, In: *Microbiology and biochemistry of cheese and fermented milk*, Law (Ed.), Blackie Academic and Profesiional, Glasgow, 1997.
Nardi et al., *J. Bacteriol.,* 179:4164-4171, 1997.
Nicolau and Sene, *Biochim. Biophys. Acta,* 721:185-190, 1982.
Nicolau et al., *Methods Enzymol.,* 149:157-176, 1987.
Niven et al., *Appl. Microbiol. Biotech.,* 44:100-105, 1995.
Nowakowski et al., *Appl. Microbiol. Biotechnol.,* 39:204-210, 1993.
O'Sullivan and Klaenhammer, *Gene,* 137:227-231, 1993.
Omirulleh et al., *Plant Mol. Biol.,* 21(3):415-28, 1993.
Payne, *J. Biol. Chem.,* 243:3395-3403, 1968.
PCT Appl. WO 94/09699
PCT Appl. WO 95/06128
Pederson et al., *J. Bacteriol.,* 181:4592-7, 1999.
Perego et al., *Mol. Microbiol.,* 5:173-85, 1991.
Potrykus et al., *Mol. Gen. Genet.,* 199:183-188, 1985.
Pritchard and Coolbear, *FEMS Microbiol. Rev.,* 12:179-206, 1993.
Punt et al., *Trends Biotechnol.,* 20(5):200-6, 2002.
Rippe et al., *Mol. Cell Biol.,* 10:689-695, 1990.
Sambrook et al., Cold Spring Harbor Laboratory, old Spring Harbor, N.Y., 2001.
Sambrook et al., In: *Molecular cloning*, Cold Spring Harbor Laboratory Press, Cold Spring Harbor, N.Y., 1989.
SAS User's Guide: Statistics, Version 5$^{th}$ Ed., SAS Inst. Inc., Cary, N.C., 1985.
Schuppan et al., *Science* 297:2218-2220, 2002.
Shine and Dalgamo, *Proc. Natl. Acad. Sci. USA,* 71:1342-1346, 1974.
Smith et al., *Anal. Biochem.,* 150:76-85, 1985.
Tan et al., *Appl. Environ. Microbiol.,* 59:1430-1436, 1993.
Terzaghi and Sandine, *Appl. Microbiol.,* 29:807-813, 1975.
Tinoco et al., *Nature* (*London*) *New Biol.,* 246:40-41, 1973.
Tynkkynen et al., *J. Bacteriol.,* 175:7523-7532, 1993.
Vader et al., *J Exp Med.* 195(5):643-649, 2002.
Wong et al., *Gene,* 10:87-94, 1980.

What is claimed is:

1. An isolated Endopeptidase polypeptide comprising an amino acid sequence with at least 90% identity to SEQ ID NO:4.

2. The isolated Endopeptidase polypeptide of claim 1, comprising an amino acid sequence with at least 95% identity to SEQ ID NO:4.

3. The isolated polypeptide of claim 2, comprising the amino acid sequence of SEQ ID NO:4.

4. A food additive composition comprising an isolated PepO3 polypeptide comprising the amino acid sequence of SEQ ID NO:4, wherein the composition is a liquid, pellet, or powder.

5. The food additive composition of claim 4, further comprising an isolated PepN polypeptide.

6. The food additive composition of claim 4, further comprising an isolated PepO2 polypeptide having the amino acid sequence of SEQ ID NO:2.

* * * * *